United States Patent
Olender et al.

(10) Patent No.: US 11,122,981 B2
(45) Date of Patent: Sep. 21, 2021

(54) ARTERIAL WALL CHARACTERIZATION IN OPTICAL COHERENCE TOMOGRAPHY IMAGING

(71) Applicant: MASSACHUSETTS INSTITUTE OF TECHNOLOGY, Cambridge, MA (US)

(72) Inventors: Max Louis Olender, Cambridge, MA (US); Lambros Athanasiou, Medford, MA (US); Elazer R. Edelman, Brookline, MA (US)

(73) Assignee: MASSACHUSEHIS INSTITUTE OF TECHNOLOGY, Cambridge, MA (US)

( * ) Notice: Subject to any disclaimer, the term of this patent is extended or adjusted under 35 U.S.C. 154(b) by 33 days.

(21) Appl. No.: 16/415,430

(22) Filed: May 17, 2019

(65) Prior Publication Data
US 2020/0359911 A1    Nov. 19, 2020

(51) Int. Cl.
G06K 9/00    (2006.01)
A61B 5/02    (2006.01)
A61B 5/00    (2006.01)
A61B 8/12    (2006.01)
G01B 9/02    (2006.01)

(52) U.S. Cl.
CPC ........ *A61B 5/02007* (2013.01); *A61B 5/0035* (2013.01); *A61B 5/0066* (2013.01); *A61B 5/0084* (2013.01); *A61B 5/6852* (2013.01); *A61B 8/12* (2013.01); *G01B 9/02091* (2013.01)

(58) Field of Classification Search
CPC . A61B 5/02007; A61B 5/6852; A61B 5/0066; A61B 5/0035; A61B 5/0084; A61B 8/12; G01B 9/02091
See application file for complete search history.

(56) References Cited

U.S. PATENT DOCUMENTS

2017/0076014 A1 * 3/2017 Bressloff ................ A61B 6/504

OTHER PUBLICATIONS

Abdolmanafi, Atefeh, et al. "Deep feature learning for automatic tissue classification of coronary artery using optical coherence tomography." Biomedical optics express 8.2 (2017): 1203-1220. (Year: 2017).*
Olender, Max L., et al. "A mechanical approach for smooth surface fitting to delineate vessel walls in optical coherence tomography images." IEEE transactions on medical imaging 38.6 (2018): 1384-1397. (Year: 2018).*

(Continued)

*Primary Examiner* — Randolph I Chu
(74) *Attorney, Agent, or Firm* — Quarles & Brady LLP

(57) ABSTRACT

A method, including: obtaining, by a processor, imaging data from a vessel; detecting, using the processor, an inner wall of the vessel based on the imaging data; identifying, using the processor, a plurality of visible edge portions of an outer wall of the vessel based on the imaging data; fitting, using the processor, a continuous surface model to the plurality of identified visible edge portions of the outer wall; and detecting, using the processor, the outer wall of the vessel based on fitting the continuous surface model to the plurality of identified visible edge portions of the outer wall such that the imaging data has defined therein a wall area between the inner wall and the outer wall of the vessel.

26 Claims, 28 Drawing Sheets
(24 of 28 Drawing Sheet(s) Filed in Color)

(56) References Cited

OTHER PUBLICATIONS

Tearney, G. et al., "Consensus standards for acquisition, measurement, and reporting of intravascular optical coherence tomography studies," Journal of the American College of Cardiology, vol. 59, No. 12, pp. 1058-1072, Mar. 2012.

Tsantis, S., et al., "Automatic vessel lumen segmentation and stent strut detection in intravascular optical coherence tomography," Med Phys 39(1), Jan. 10, 2012, 503-513 (2012).

Ughi, G. J., et al. "Automatic segmentation of in-vivo intra-coronary optical coherence tomography images to assess stent strut apposition and coverage," Int J Cardiovasc Imaging 28(2), Feb. 25, 2011, 229-241 (2012).

Van Soest G., et al., "Atherosclerotic tissue characterization in vivo by optical coherence tomography attenuation imaging," J. Biomed. Opt. 15(1), 11105 (2010).

Vignali, L., et al. "Research and clinical applications of optical coherence tomography in invasive cardiology: a review," Curr Cardiol Rev 10(4), Jun. 5, 2014, 369-376 (2014).

Waller B. "The eccentric coronary atherosclerotic plaque: Morphologic observations and clinical relevance," Clin. Cardiol., vol. 12, No. 1, pp. 14-20, Jan. 1989.

Waller, B. et al. "Anatomy, histology, and pathology of coronary arteries: A review relevant to new interventional and imaging techniques—Part I," Clin. Cardiol., vol. 15, No. 6, pp. 451-457, Jun. 1992.

Weiss V, et al. "Advanced surface fitting techniques," Computer Aided Geometric Design, vol. 19, No. 1, pp. 19-42, Jan. 2002.

Xu, C. Y., et al. "Characterization of atherosclerosis plaques by measuring both backscattering and attenuation coefficients in optical coherence tomography," J. Biomed. Opt. 13(3), 34003 (2008).

Zahnd G, et al., "Contour segmentation of the intima, media, and adventitia layers in intracoronary OCT images: application to fully automatic detection of healthy wall regions," Int. J. CARS, vol. 12, No. 11, pp. 1923-1936, Nov. 2017.

Ahn, C. Y., et al, "Automated Measurement of Stent Strut Coverage in Intravascular Optical Coherence Tomography," J. Korean Phys. Soc. 66(4), 558-570 (2015).

Alfonso F, et al, "Combined use of optical coherence tomography and intravascular ultrasound imaging in patients undergoing coronary interventions for stent thrombosis," Heart, vol. 98, No. 16, pp. 1213-1220, Aug. 2012.

Amidror I, "Scattered data interpolation methods for electronic imaging systems: a survey," J. Electron. Imaging, vol. 11, No. 2, p. 157, Apr. 2002.

Amrute J, et al. "Polymeric endovascular strut and lumen detection algorithm for intracoronary optical coherence tomography images," J. Biomed. Opt 23 3 1-14., Mar. 2018.

Athanasiou, L., et al., "Computational Cardiology," IEEE J. Biomed. Heal. Informatics, 1-1 (2018).

Athanasiou, L.S. et al, "A deep learning approach to classify atherosclerosis using intracoronary optical coherence tomography," in SPIE Medical Imaging, 2019.

Athanasiou, L.S. et al, "Methodology for fully automated segmentation and plaque characterization in intracoronary optical coherence tomography images," J. Biomed. Opt, vol. 19, No. 2, p. 026009, Feb. 2014.

Athanasiou, L.S. et al, "Optical Coherence Tomography: Basic Principles of Image Acquisition," [Intravascular Imaging: Current Applications and Research Developments], IGI Global, 180-194 (2011).

Athanasiou, L.S. et al, "Optimized computeraided segmentation and three-dimensional reconstruction using intracoronary optical coherence tomography,"IEEE J. Biomed. Health Inform, vol. 22, No. 4, pp. 1168-1176, Jul. 2018.

Benjamin E, et al., "Heart disease and stroke statistics—2018 update: A report from the American Heart Association," Circulation, vol. 137, No. 12, pp. e67-e492, Mar. 2018.

Bezerra, H. G., et al., "Intracoronary Optical Coherence Tomography: A Comprehensive Review Clinical and Research Applications," Jacc-Cardiovascular Interv. 2(11), 1035-1046 (2009).

Celi S et al. "In-vivo segmentation and quantification of coronary lesions by optical coherence tomography images for a lesion type definition and stenosis grading," Med. Image Anal, vol. 18, No. 7, pp. 1157-1168, Oct. 2014.

Celi S, et al. "Superficial coronary calcium analysis by OCT: Looking forward an imaging algorithm for an automatic 3D quantification," Int. J. Cardiol, vol. 168, No. 3, pp. 2958-2960, Oct. 2013.

Celi, S., et al. "Multimodality imaging for interventional cardiology." Current pharmaceutical design 23.22 (2017): 3285-3300.

Chiastra C, et al, "Computational replication of the patientspecific stenting procedure for coronary artery bifurcations: From OCT and CT imaging to structural and hemodynamics analyses," J. Biomech, vol. 49, No. 11, pp. 2102-2111, Jul. 2016.

Chiastra C, et al, "Patient-Specific Modeling of Stented Coronary Arteries Reconstructed from Optical Coherence Tomography: Towards a Widespread Clinical Use of Fluid Dynamics Analyses," J. Cardiovasc. Trans. Res, vol. 11, No. 2, pp. 156-172, Apr. 2018.

Chiastra C, et al, "Reconstruction of stented coronary arteries from optical coherence tomography images: feasibility, validation, and repeatability of a segmentation method," PLoS One, vol. In press, No. 6, pp. 1-23, 2017.

Cleveland W, "Robust locally weighted regression and smoothing scatterplots," J. Amer. Statist. Assoc, vol. 74, No. 368, pp. 829-836, Dec. 1979.

Garvin, M. et al. "Automated 3-D intraretinal layer segmentation of macular spectral-domain optical coherence tomography images," IEEE Trans. Med. Imaging, vol. 28, No. 9, pp. 1436-1447, Sep. 2009.

Gessert, N., et al, "Automatic Plaque Detection in IVOCT Pullbacks Using Convolutional Neural Networks," IEEE Trans. Med. Imaging, 1-1 (2018).

Girard, M. A. et al. "Shadow removal and contrast enhancement in optical coherence tomography images of the human optic nerve head," Invest. Ophthalmol. Vis. Sci., vol. 52, No. 10, p. 7738, Sep. 2011.

Gonzalo N, et al., "Second-generation optical coherence tomography in clinical practice. High-speed data acquisition is highly reproducible in patients undergoing percutaneous coronary intervention," Rev. Española Cardiol. (English Ed.), vol. 63, No. 8, pp. 893-903, Jan. 2010.

He, S., et al., "Convolutional neural network based automatic plaque characterization for intracoronary optical coherence tomography images," Med. Imaging 2018 Image Process. 10574, E. D. Angelini and B. A. Landman, Eds., 107, SPIE (2018).

Hong, M. et al. "Intravascular ultrasound assessment of patterns of arterial remodeling in the absence of significant reference segment plaque burden in patients with coronary artery disease," Journal of the American College of Cardiology, vol. 42, No. 5, pp. 806-810, Sep. 2003.

Hou, J., et al. "Comparison of Intensive Versus Moderate Lipid-Lowering Therapy on Fibrous Cap and Atheroma Volume of Coronary Lipid-Rich Plaque Using Serial Optical Coherence Tomography and Intravascular Ultrasound Imaging," Am. J. Cardiol. 117(5), Jan. 19, 2016, 800-806 (2016).

Imola F, et al, "Safety and feasibility of frequency domain optical coherence tomography to guide decision making in percutaneous coronary intervention," EuroIntervention, vol. 6, No. 5, pp. 575-581, Nov. 2010.

Ishikawa, H. et al. (2005). Macular segmentation with optical coherence tomography. Investigative ophthalmology & visual science, 46(6), 2012-2017.

Jang I, et al., "Visualization of coronary atherosclerotic plaques in patients using optical coherence tomography: comparison with intravascular ultrasound," J. Amer. Coll. Cardiol, vol. 39, No. 4, pp. 604-609, Feb. 2002.

Kafieh R, et al, "Intra-retinal layer segmentation of 3D optical coherence tomography using coarse grained diffusion map," Medical Image Analysis, vol. 17, No. 8, pp. 907-928, Dec. 2013.

(56) References Cited

OTHER PUBLICATIONS

Keeve E, et al, "Deformable modeling of facial tissue for craniofacial surgery simulation," Comput. Aided Surg, vol. 3, No. 5, pp. 228-238, Jan. 1998.
Kok A, et al, "Peak cap stress calculations in coronary atherosclerotic plaques with an incomplete necrotic core geometry," Biomed. Eng. Online, vol. 15, No. 1, p. 48, Dec. 2016.
Kolluru, C., et al., "Deep neural networks for A-line-based plaque classification in coronary intravascular optical coherence tomography images," J. Med. Imaging 5(04), 1 (2018).
Konig A. et al, "Virtual histology," Heart, vol. 93, No. 8, pp. 977-982, 2007.
Kubo T, et al. "OCT compared with IVUS in a coronary lesion assessment: The OPUS-CLASS study," JACC Cardiovasc. Imaging, vol. 6, No. 10, pp. 1095-1104, 2013.
Kubo T, et al., "Feasibility of optical coronary tomography in quantitative measurement of coronary arteries with lipid-rich plaque," Circ. J, vol. 79, No. 3, pp. 600-606, 2015.
Maity, A. et al. "A comparative study on approaches to speckle noise reduction in images," in 2015 International Conference on Computational Intelligence and Networks, Jan. 2015, pp. 148-155.
Meseure P et al, "Deformable body simulation with adaptive subdivision and cuttings," Proc. WSCG, vol. 97, pp. 361-370, Feb. 1997.
Mintz, G. et al. "Contribution of inadequate arterial remodeling to the development of focal coronary artery stenoses : An intravascular ultrasound study," Circulation, vol. 95, No. 7, p. 1791-1798, Apr. 1997.
Morlacchi S et al, "Modeling stented coronary arteries: Where we are, where to go," Ann. Biomed. Eng, vol. 41, No. 7, pp. 1428-1444, Jul. 2013.
Nabel E et al, "A tale of coronary artery disease and myocardial infarction," N. Engl. J. Med, vol. 366, No. 1, pp. 54-63, Jan. 2012.
Olender, M. L., et al. "Estimating the internal elastic membrane cross-sectional area of coronary arteries autonomously using optical coherence tomography images," 2017 IEEE EMBS Int. Conf. Biomed. Heal. Informatics, 109-112, IEEE (2017).
Oliveira, Dab, et al. "Coronary calcification identification in optical coherence tomography using convolutional neural networks." Medical Imaging 2018: Biomedical Applications in Molecular, Structural, and Functional Imaging. vol. 10578. International Society for Optics and Photonics, 2018.
Prati F, et al., "Expert review document on methodology, terminology, and clinical applications of optical coherence tomography: Physical principles, methodology of image acquisition, and clinical application for assessment of coronary arteries and atherosclerosis," European Heart Journal, vol. 31, No. 4, pp. 401-415, Feb. 2010.
Sakata K, et al. "Expansion of the clinical application of optical coherence tomography to percutaneous coronary intervention and assessment of the instability of coronary atherosclerosis," Circ. J, vol. 79, No. 3, pp. 513-514, 2015.
Schoenhagen, P. et al. "Extent and direction of arterial remodeling in stable versus unstable coronary syndromes : An intravascular ultrasound study," Circulation, vol. 101, No. 6, p. 598-603, Feb. 2000.
Schumaker LL, "Fitting surfaces to scattered data," Approximation Theory II. Washington, DC, USA: Scientific Research, 1976, pp. 203-268. [Online]. Available: https://apps.dtic.mil/docs/citations/ADA027870.
Sobel I. et al. "A 3×3 isotropic gradient operator for image processing," in Stanford Artificial Project, 1968, pp. 271-272.
Sutskever, I., et al. "On the importance of initialization and momentum in deep learning," Proc. 30th Int. Conf. Mach. Learn. 28(3), S. Dasgupta and D. McAllester, Eds., 1139-1147, PMLR, Atlanta, Georgia, USA (2013).
Tanaka K, "Statistical-mechanical approach to image processing," J. Phys. A. Math. Gen, vol. 35, No. 37, pp. R81-R150, Sep. 2002.
Tang D, et al., "Image-based modeling for better understanding and assessment of atherosclerotic plaque progression and vulnerability: Data, modeling, validation, uncertainty and predictions," J. Biomech, vol. 47, No. 4, pp. 834-846, Mar. 2014.

* cited by examiner

ARTERIAL WALL CHARACTERIZATION IN OPTICAL COHERENCE TOMOGRAPHY IMAGING

STATEMENT REGARDING FEDERALLY SPONSORED RESEARCH

This invention was made with government support under 5R01GM049039-23 awarded by the U.S. National Institutes of Health. The government has certain rights in the invention.

CROSS-REFERENCE TO RELATED APPLICATIONS

N/A.

FIELD OF THE INVENTION

This invention relates generally to automated procedures for identifying structures and classifying tissue types in images, and more particularly to methods and apparatus for automated identification and classification of atherosclerotic plaques in intravascular image data.

BACKGROUND

Coronary artery disease (CAD) is the scourge of modern society, responsible for 1 in every 7 deaths in the United States. Imaging of coronary vessels is a primary step in prognosis and treatment of CAD, and various imaging modalities have been introduced into the clinic. Invasive techniques are the most effective modalities for detecting borders of vessels and the presence of atheromatous plaques as well as characterizing the extent and composition of such plaques. Optical coherence tomography (OCT) utilizes light to perform imaging, leading to remarkable resolution (10-20 µm axially, 20-40 µm laterally) which allows for highly detailed imaging of the near field. However, the use of light (e.g. instead of ultrasound) results in relatively low penetration depth (1-2.5 mm) with strong dependence on tissue optical properties, allowing visual identification of vessel outer border (intima- or plaque-media interface) only in healthy or minimally-diseased vessel segments.

SUMMARY

Exemplary embodiments according to the present disclosure can be provided to delineate arterial wall area (WAR) and/or to classify tissue within the WAR.

In one embodiment, a method, including: obtaining, by a processor, imaging data from a vessel; detecting, using the processor, an inner wall of the vessel based on the imaging data; identifying, using the processor, a plurality of visible edge portions of an outer wall of the vessel based on the imaging data; fitting, using the processor, a continuous surface model to the plurality of identified visible edge portions of the outer wall; and detecting, using the processor, the outer wall of the vessel based on fitting the continuous surface model to the plurality of identified visible edge portions of the outer wall such that the imaging data has defined therein a wall area between the inner wall and the outer wall of the vessel.

In another embodiment, a system, including at least one hardware processor that is programmed to: obtain imaging data from a vessel; detect an inner wall of the vessel based on the imaging data; identify a plurality of visible edge portions of an outer wall of the vessel based on the imaging data; fit a continuous surface model to the plurality of identified visible edge portions of the outer wall; and detect the outer wall of the vessel based on fitting the continuous surface model to the plurality of identified visible edge portions of the outer wall such that the imaging data has defined therein a wall area between the inner wall and the outer wall of the vessel.

In yet another embodiment, a method, including: providing, using a processor, imaging data from a vessel, the imaging data including an identified inner wall of the vessel and an identified outer wall of the vessel such that the imaging data has defined therein a wall area between the inner wall and the outer wall of the vessel; and automatically classifying, using the processor, a tissue type of a portion of the wall area using a trained classification model.

The foregoing and other aspects and advantages of the present disclosure will appear from the following description. In the description, reference is made to the accompanying drawings that form a part hereof, and in which there is shown by way of illustration one or more exemplary versions. These versions do not necessarily represent the full scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing features of this invention, as well as the invention itself, may be more fully understood from the following description of the drawings in which:

FIGS. 3A and 3B show convolution results calculating the weighted mean Sobel output above (FIG. 3A) and below (FIG. 3B) each pixel. Red indicates a positive value (light-to-dark transition); yellow indicates a negative value (dark-to-light). FIG. 3C shows a heat map illustrating the product of the proximal and distal convolutions meeting the imposed signage requirements (light-to-dark transition above and dark-to-light transition below a given pixel). FIG. 3D shows the original flattened image on which the operations were performed.

FIG. 5A shows radial distance between expert annotation and algorithm surface summed over all columns, used as the object function for optimization; FIG. 5B shows sensitivity, specificity, Jaccard Index, Dice Index, $R_{over}$, and $R_{nonover}$; FIG. 5C shows parameter output values ($K_2/K_1$, $K_3/K_1$, $K_4/K_1$, $\alpha/K_1$).

FIG. 7A shows performance metrics (sensitivity, specificity, Jaccard Index, Dice Index, $R_{over}$, and $R_{nonover}$); FIG. 7B shows normalized parameter output values ($K_2/K_1$, $K_3/K_1$, $K_4/K_1$, $\alpha/K_1$).

FIG. 8A shows an error plot showing strong correlation between the two areas ($R^2=0.94$ before smoothing, 0.96 after smoothing; dashed line shows 1-to-1 ratio); FIG. 8B shows a Bland-Altman plot (average: −0.36 mm² before smoothing, −0.20 mm² after smoothing; standard deviation: 0.82 mm² before smoothing, 0.65 mm² after smoothing) which illustrates that there is no substantial systematic error (i.e. error is distributed).

FIG. 11A provides an error plot showing strong correlation between the two areas ($R^2=0.89$; dashed line shows 1-to-1 ratio); FIG. 11B provides a Bland-Altman plot (average: 0.07 mm², standard deviation: 1.25 mm²) which illustrates that no clear systematic error is present.

FIG. 12A shows an error plot showing correlation between the two areas ($R^2$ ranges from 0.79 to 0.82; dashed line shows 1-to-1 ratio); FIG. 12B shows a Bland-Altman plot which illustrates substantial systematic error (error not regularly distributed), with existing interpolation and fit methods systemically underestimating area. Note that these methods less frequently overestimated area in larger vessels (often associated with lower visibility).

FIG. 15A provides an error plot showing exceptional correlation between the two areas ($R^2_{inner}>0.99$, $R^2_{outer}=0.93$; dashed line shows 1-to-1 ratio); FIG. 15B provides a Bland-Altman plot (average: 0.10 & 0.53 mm², standard deviation: 0.14 & 1.02 mm², respectively) which illustrates that no substantial systematic error is present (i.e. error is distributed).

FIG. 16A provides an error plot showing correlation between the two areas delineated by human experts in OCT and IVUS ($R^2_{inner}=0.66$, $R^2_{outer}=0.75$; dashed line shows 1-to-1 ratio); FIG. 16B provides an error plot showing correlation between the areas delineated by the algorithm in OCT and a human expert in IVUS ($R^2_{inner}=0.68$, $R^2_{outer}=0.67$; dashed line shows 1-to-1 ratio); FIG. 16C provides a Bland-Altman plot corresponding to FIG. 16A and showing deviation between the two areas delineated by human experts in OCT and IVUS (average: 0.05 & 0.78 mm², standard deviation: 1.94 & 1.88 mm², respectively), which illustrates minor systematic offset and greater absolute difference in larger vessels; FIG. 16D provides a Bland-Altman plot corresponding to FIG. 16C and showing deviation between the areas delineated by the algorithm in OCT and a human expert in IVUS (average: 0.25 & 0.72 mm², standard deviation: 1.82 & 2.12 mm², respectively), which illustrates minor systematic offset and greater absolute difference in larger vessels.

DETAILED DESCRIPTION OF THE INVENTION

Figure 1:
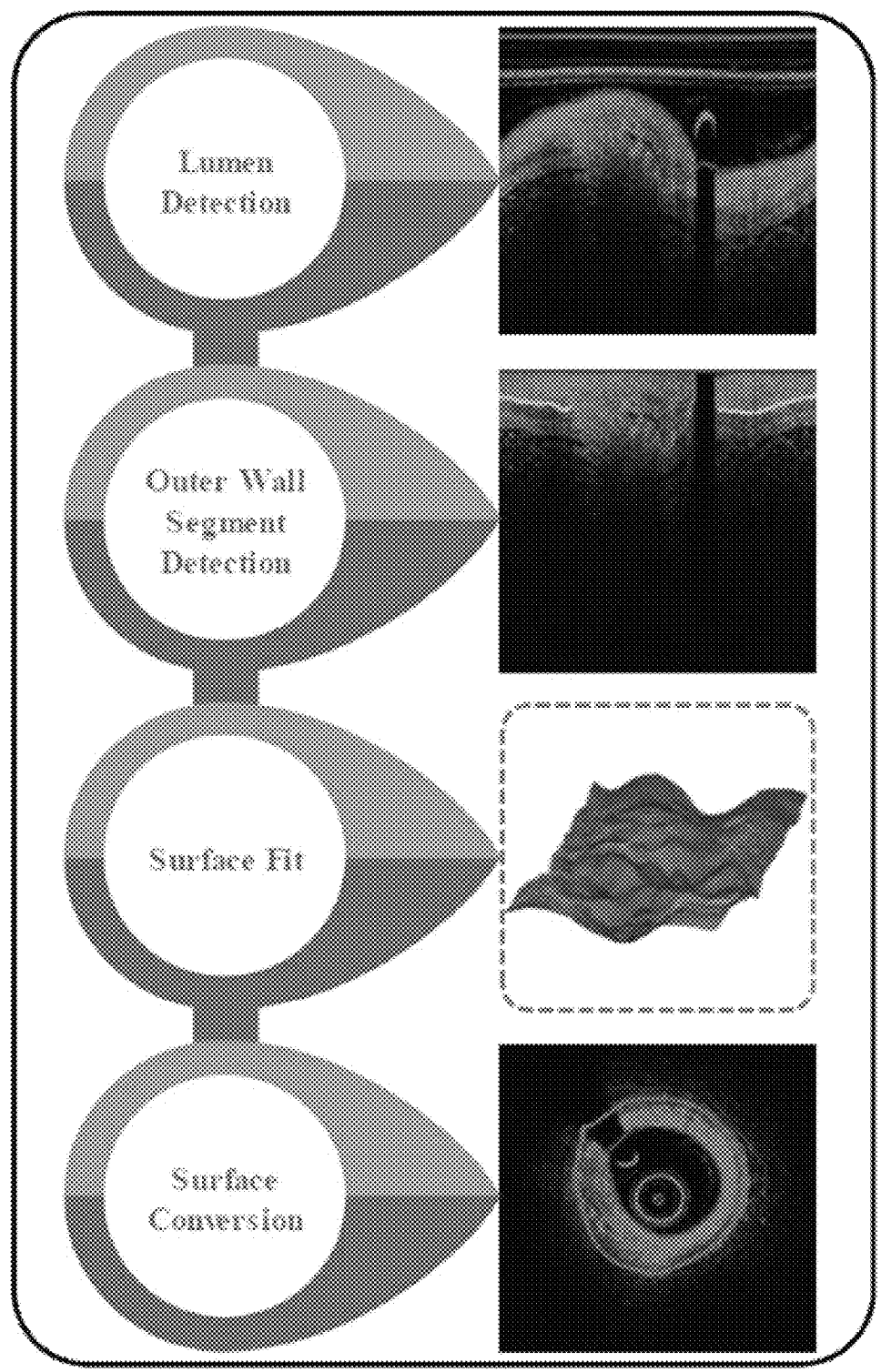
FIG. 1 shows an overview of an exemplary version of wall area (WAR) detection including methodological procedures including lumen detection and smoothing, visible outer border segment detection, surface fit to wall segments, and surface reconstitution with conversion from cylindrical to Cartesian coordinates.

Before any embodiments of the invention are explained in detail, it is to be understood that the invention is not limited in its application to the details of construction and the arrangement of components set forth in the following description or illustrated in the attached drawings. The invention is capable of other embodiments and of being practiced or of being carried out in various ways. Also, it is to be understood that the phraseology and terminology used herein is for the purpose of description and should not be regarded as limiting. For example, the use herein of "including," "comprising," or "having" and variations thereof is meant to encompass the items listed thereafter and equivalents thereof as well as additional items.

Optical coherence tomography (OCT) is a fiber-based intravascular imaging modality that produces high-resolution tomographic images of arterial lumen and vessel wall morphology using interferometry. Manual analysis of the diseased arterial wall is possible but time-consuming and sensitive to inter-observer variability; therefore, machine-learning methods have been developed and implemented to automatically detect and classify mural (vessel wall) composition of atherosclerotic vessels.

Until now, none of the tissue classification methods 1) have been able to characterize the whole arterial wall, and 2) have considered in their analysis the OCT imaging limitations, e.g. shadowed areas. As a result, they cannot present a robust plaque characterization method which provides a color-coded image with the different plaque types of the arterial wall. This limits the extended use of OCT technology in automatic plaque detection; an older imaging technology, intravascular ultrasound imaging (IVUS), and its commercially available virtual histology (VH) analysis software, VH-IVUS, are instead used. VH-IVUS provides color-coded images and the (FDA-approved) software has been used for over a decade even though its robustness is widely questioned.

The superiority of OCT in detecting features that are associated with plaque vulnerability, including the measurement of fibrous cap thickness, which cannot be accurately evaluated by IVUS or by any other intravascular imaging technique, has made it a method of choice in clinical cardiology. Nevertheless the absence of a plaque characterization method similar to VH-IVUS restricts the method from fully replacing IVUS.

Embodiments of the presently-disclosed procedures subdivide the arterial wall into up to six different classes, similarly to data that is produced using VH-IVUS, including one or more of: calcium, lipid tissue, fibrous tissue, mixed tissue, non-pathological tissue or media, and no visible tissue. The procedure may include: 1) defining wall area (WAR) using a lumen and outer border detection algorithm, and 2) automatic characterization of the WAR, e.g. using a convolutional neural network (CNN) algorithm.

To test and validate the procedures, medical experts manually annotated 700 images of diseased coronary arteries from 28 patients, while the non-pathological wall and media was automatically detected based on factors such as the Euclidian distance of the lumen to the outer border of the WAR (the approach implemented in VH-IVUS). Using embodiments of the procedures disclosed herein, an overall classification accuracy of 98.9% was achieved, indicating great promise for clinical translation.

While there have been other attempts at using automated procedures (e.g. neural network based approaches) to identify and classify tissues in interferometric data (e.g. OCT images), these have produced inaccurate results in part because of the lack of clear boundaries defining the vessel walls. In prior attempts, neural networks were not able to distinguish between tissue that was part of a vessel and tissue that was adjacent to but outside of the vessel. For example, fibrous tissue that may be part of a plaque can be difficult for a neural network to distinguish from extravascular tissue. Tissue that is distal to lipid (or other highly-attenuating) tissue may appear dark due to the inability of signal to propagate through the medium and back. Similarly, any tissue that is distal to the proximal surface of a guidewire is cast in a shadow and appears dark due to the inability for signal to penetrate the metal guidewire. In addition the lumen itself appears dark (except for the occasional unintended unflushed blood artifacts). Far-field tissue also appears dark due to the limited penetration depth of OCT. Image data from any of these sources cannot be distinguished in isolation (e.g. by a neural network analyzing individual pixels or patches). As a result, the results of automated classification procedures may be over- or under-inclusive of vessel wall tissues, although certain tissue types (e.g. calcium-containing tissues) tend to have a more definite signature and are less likely to be confused with tissues outside the vessel. Nevertheless, it has been found that the procedure of identifying vessel boundaries prior to performing an automated identification of tissue types greatly and unexpectedly improves the precision of tissue classification, producing a much higher degree of accuracy than has been achieved by others. In various embodiments, identification of wall area, even prior to a classification step, can provide useful information (such as plaque area/burden) that cannot be obtained using other known techniques. In other embodiments, automated WAR delineation may be performed as an initial step prior to manual annotation/segmentation.

Without being limited by theory, automated procedures such as those based on neural networks may have difficulties identifying boundaries and distinguishing between tissues that are part of a vessel wall and those that are not because of the nature of interferometric data, which is collected from within the vessel and as a result can be attenuated and have reduced clarity and quality in the outer vessel regions. The issue of reduced data clarity and quality in the outer vessel regions is particularly acute in the places where there are plaques, arguably where the information is most needed. The presence of a plaque further degrades the data that is collected from the outer vessel regions due to the reduced amount of light that penetrates the plaque, leading to a reduction of image quality further from the center of the vessel. On the other hand, the procedures disclosed herein for delineating the outer vessel boundaries are able to utilize information about the vessel such as the outer boundaries in regions without plaques to identify the WAR, which can then be combined with an automated procedure (e.g. a neural network based procedure) to classify tissue types within the WAR with a high degree of accuracy. The conventional approach of using a single automated procedure to simultaneously identify tissue types as well as vessel boundaries has had only limited success and the present procedures, which employ a two-step process in which vessel wall area is determined first followed by tissue type classification, are demonstrated to produce unexpectedly improved results over the conventional approach.

Wall Area Detection

Automated analysis of vascular imaging techniques is limited by the inability to precisely determine arterial borders. Intravascular optical coherence tomography (OCT) offers unprecedented detail of artery wall structure and composition, but does not provide consistent visibility of the outer border of the vessel due to limited penetration depth. Existing interpolation and surface fitting methods prove insufficient to accurately fill the gaps between the irregularly-spaced and sometimes unreliably-identified visible segments of the vessel outer border. This disclosure describes an intuitive, efficient, and flexible new method of three-dimensional surface fitting and smoothing suitable for this task, which in certain embodiments may be based on fitting a continuous surface model to the data. In some embodiments, an anisotropic linear-elastic mesh is fit to irregularly-spaced and uncertain data points corresponding to visible segments of vessel borders, enabling the fully-automated delineation of the entire inner and outer borders of diseased vessels in OCT images. In a clinical dataset, the presented smooth surface fitting approach had great agreement when compared to human annotations: areas differed by just 11±11% (0.93±0.84 mm$^2$), with a coefficient of determination of 0.89. In various embodiments, overlapping and non-overlapping area ratios were 0.91 and 0.18, respectively, with sensitivity of 90.8 and specificity of 99.0. This spring mesh method of contour fitting significantly outperformed all alternative surface fitting and interpolation approaches tested. The application of this promising method is expected to enhance clinical intervention and translational research using OCT.

Despite certain shortcomings, OCT has been proven to be not just feasible and safe for clinical use but has also been demonstrated to have the capacity to offer insights and detailed information not offered by other imaging modalities. OCT can diagnose CAD, characterize the majority of plaque types with excellent reproducibility, guide coronary interventions such as stent deployment, and assess stents after deployment. Nonetheless, the aforementioned limitation for outer border identification prevents adequate estimation of plaque burden and proper vessel sizing, both being clinically relevant data.

Intravascular optical coherence tomography (OCT) is a catheter-based imaging modality developed over recent decades that has become popular in interventional cardiology. OCT has much higher resolution than other intravascular imaging modalities, like intravascular ultrasound (IVUS): 12-18 microns axially and a lateral resolution of 20-90 microns. OCT calculates the proportion of the light backscattered and absorbed by the vessel tissue and reconstructs two-dimensional (2D) images which represent the cross sections (i.e. tomographic information) of the imaged vessel.

OCT can provide accurate measurements of a lumen of a vessel, assess wall morphology, and allow detection of four different tissue types: calcium (C), lipid tissue (LT), fibrous tissue (FT), and mixed tissue (MT). Moreover, use of OCT enables the detection of features that are associated with plaque vulnerability, including the measurement of fibrous cap thickness, which cannot be accurately evaluated by IVUS or by any other in situ vascular imaging technique. However, the technology has a drawback, namely the limited tissue penetration (maximum depth: 1.5-2.0 mm), which may not allow visualization and assessment of the entire plaque and the media-adventitia border.

The growing evidence of the value of OCT in clinical and research arenas has increased demand to measure plaque burden and content. Yet, it is precisely aspects of the plaque (e.g. lipid pools) that most severely limit penetration, and automatic and accurate approximation of the full vessel outer border is challenging with OCT, especially when only a subset of the feature is visible. While some advances in automated OCT analysis have worked within this constraint to segment and quantify superficial plaques, others have sought to overcome the limitation. A preliminary approach towards automatic delineation of the wall utilized standard filtering and edge-detection methods, coupled with frame-by-frame shape fitting, to approximate the outer border and vessel cross-sectional area. Later work with similar aims performed automatic multi-layer segmentation of the vessel wall using a method akin to work in retinal OCT layer segmentation: a front propagation scheme relying on gray-scale gradient information. However, this approach was limited by validation only in healthy wall regions, where the absence of significant plaque permitted clear visibility of the various layers. The challenge at hand therefore remained unresolved for clinically-relevant applications.

Physiological understanding and constraints can be brought to bear on the problem. Plaque burden follows a continuity inside the vessel and does not change dramatically from frame to frame. Therefore, using a priori knowledge of the structural and geometric constraints of vessel walls and working in 3D space, rather than on a frame-by-frame basis, the limited visibility of the outer vessel wall can be largely overcome. Indeed, the non-visible parts of the outer vessel border can be approximated in the 3D space to estimate the full arterial wall position.

Many methods exist for filling gaps in three-dimensional (3D) information, though most are variations of interpolation or surface fitting, which are limited in flexibility, intuitiveness, ability to incorporate secondary information, and computational efficiency. Interpolation methods construct functions that intersect known data points or positions, and utilize various methods to approximate the values or positions lying between them. Fundamentally, smoothing is limited in interpolation methods, as functions are constrained to pass through available data points, which may themselves be non-smooth and/or unreliable. When the available data may include noise, error, or inaccuracies, or are not reliable, as is the case with the application at hand, surface fitting is generally acknowledged to be preferable to interpolation; scattered data fitting techniques seek to find a reasonably-approximating, ostensibly-smooth surface to represent the underlying data trend. However, the shapes and contours that can be achieved with existing surface fitting techniques are fundamentally constrained—most surfaces must conform, locally or globally, to a polynomial function. This presents a vital limitation, particularly in applications to natural and complex systems which cannot be represented with sufficient fidelity by such simplified expressions. Furthermore, because neither standard interpolation nor surface fitting techniques can incorporate additional inputs from the rich information available in imaging data, resulting approximations are heavily biased when the input data points are not representative of, or equally-distributed from, the underlying data. In the present case of the vessel wall, these techniques are expected to underestimate unknown values of wall position because missing data points (non-visible wall segments) are inherently more likely to have values (radial depths) at the extremes of, or exceeding, those of the available data point values (visible wall segment depths).

The approach described here leverages key benefits of simple mechanical systems. For example, the simplicity and elegance of Hookean linear-elastic spring models lend themselves to unparalleled efficiency because they allow straightforward expression in matrix operations and the associated benefits in solving systems of equations. For this reason, deformable mass-spring tissue models have been implemented instead of finite-element tissue models to realistically simulate interactive surgeries in real time, and a spring surface mesh has been implemented to simulate dynamic organ behavior corresponding to surgical operations with precision and speed. While not applied to image processing, these applications exemplify the efficiency of Hookean linear-elastic springs models where large systems of equations must be constructed and solved to calculate three-dimensional response to external loads. Nevertheless, application of mechanical models to the field of image processing has been very limited. Bayesian statistics and statistical mechanics have been applied to probabilistic image restoration techniques and extended to additional image processing tasks, such as edge detection, image segmentation, motion detection, and image compression. However, more dynamic systems like the one implemented in this work have not been explored.

Disclosed herein are embodiments of a smoothing surface fitting method which overcomes the challenges of existing interpolation and surface fitting methods, and which enables the delineation of the entire inner and outer borders of vessels in OCT images. The new method, which is inspired by intuitive linear-elastic springs common in classical (Newtonian) mechanics, is both efficient in 3D space and conspicuously effective. The uniqueness of this work lies not only in its application—in autonomous delineation of the full outer border of a diseased coronary artery using OCT imaging alone—but also in the approach used to reconstruct and smooth surfaces using incomplete information. The algorithm was rigorously validated in 7 patients (724 frames) through comparison to expert annotations, and its performance was compared to alternative interpolation and surface fitting approaches.

Thus, in various embodiments, interferometric data obtained from a tissue such as a vessel (e.g. a coronary artery) is obtained from a device such as an OCT-based catheter probe. The interferometric data may be a helical scan that is obtained by rotating the probe while it is advanced through the tissue. The data may include a number of A-lines from various points on the tissue and may be processed to provide a series of cross-sections through the tissue. For example, if the tissue is a vessel the cross-sections may be through the center of the lumen of the vessel, which may also referred to herein as a "frame." In various embodiments, the data that is analyzed may include a consecutive series of cross-sections or frames, or there may be gaps (either equally-spaced or variable gaps) between cross-sections. To the extent that the data may not be continuous and may contain one or more gaps between frames, the spacing between frames can be accounted for mathematically when performing the processing steps disclosed herein.

In various embodiments the method may include one or more of the following (FIG. 1): 1) the inner (lumen) border of the vessel is detected in each frame and smoothed as a surface; 2) the image is flattened relative to the lumen and visible edges of the outer wall are identified using image contrast enhancement, 3D filtering, application-specific edge-detection kernels, and region-growing; 3) a continuous surface model such as an anisotropic linear-elastic mesh is fit to the identified edges with applied forces to generate a continuous, smooth surface along the outer border; 4) the results are finally reconstituted to the pre-flattened reference frame and converted to a Cartesian coordinate system. Note that the surface fitting method can be used at least twice; it was used first to smooth the inner border (for which no information was missing but the available information was a bit noisy and not perfectly reliable), and subsequently to both complete and smooth the outer border (when only incomplete, irregularly-spaced, and sometimes unreliable information was available).

A further note of clarification regarding these steps is warranted before one or more exemplary embodiments of the inner and outer border identification is explained in detail. It is to be understood that identifying a plurality of visible edge portions of an outer wall of the vessel need not discriminate exact locations of discrete segments, but may instead in certain embodiments be manifest as a weighted map indicating likelihood of segment location. It is to be further understood that fitting a continuous surface model to the plurality of identified visible edge portions of the outer wall is considered to include, in various embodiments, fitting of standard or unique surface fitting models, multi-dimensional interpolation, max-flow min-cut segmentation, other graph-based methods, shape fitting, and front-propagation schemes utilizing the aforementioned edge (portion) detection. In still other embodiments, fitting a continuous surface model may also be achieved in segments or in piece-wise fashion. What follows is a description of an exemplary embodiment of border identification in which exact locations of candidate edges are identified and fit with a unique surface fitting model, beginning with a general description of the surface fitting model and followed by a description of its implementation.

Spring Mesh Surface Construction

We define, as for any surface fitting approach, a finite set of m known points $P_r \in \mathbb{R}^3$ and tolerances $\epsilon_r \in \mathbb{R}_+$. The desired surface $S \subset \mathbb{R}^3$ approximates the positions of the known (and unknown) points such that $$|S_{P_r} - P_r| \leq \epsilon_r, r \in \{1, \ldots, m\} \tag{1}$$

Given the application to image processing and the constraints of implementation, the assumption is made that known points can be assigned a discretized position at an indexed location. Specifically, described herein is an implementation in a 3D discretized space with q sequential planes $j \in [1;q]$ each containing p columns $i \in [1;p]$, where each position can be assigned an index of (i,j,k).

Figure 2:
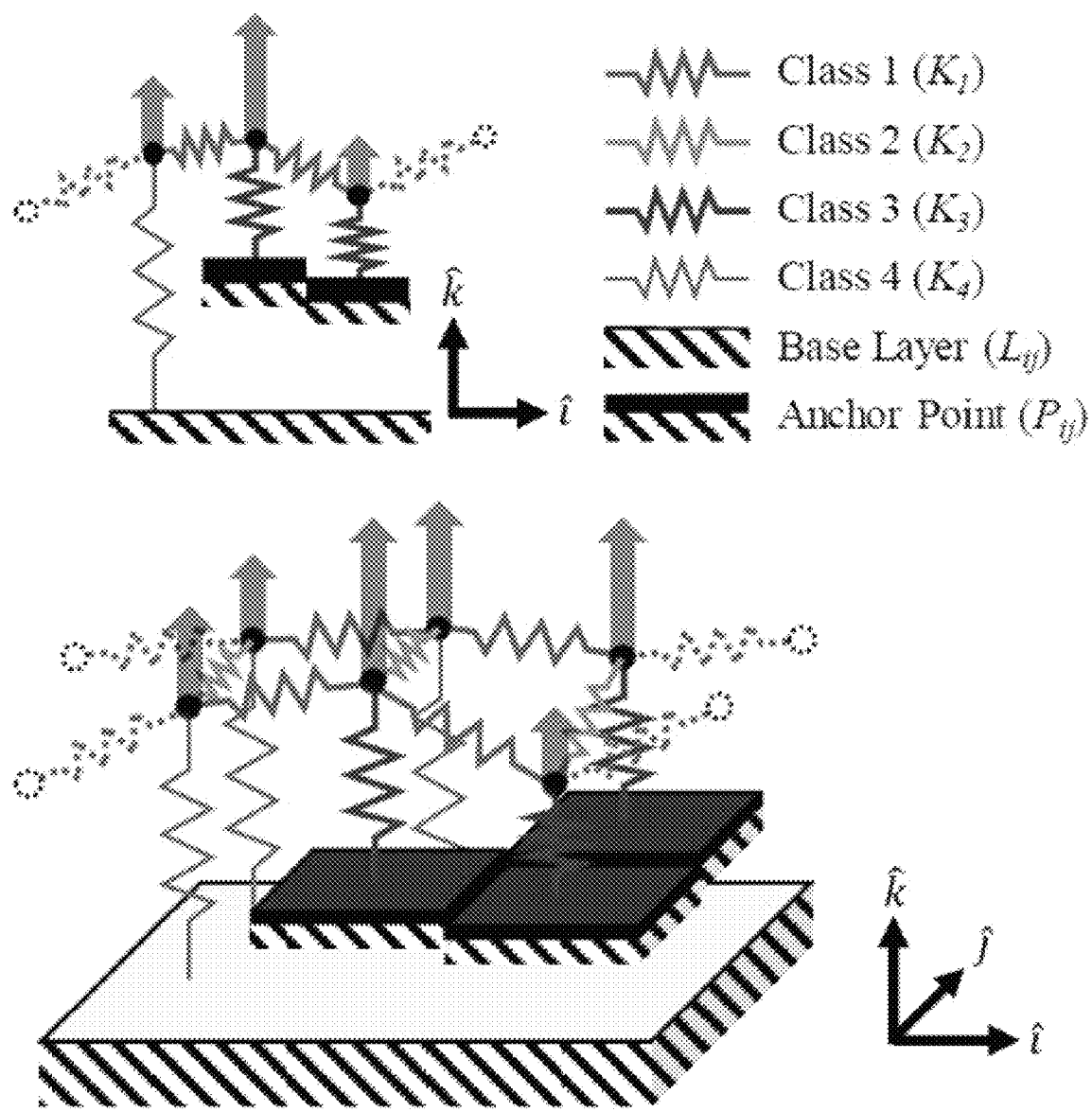
FIG. 2 shows a schematic system structure in two and three dimensions. Spring colors indicate class with different stiffness K: 1) blue ($K_1$); 2) yellow ($K_2$); 3) red ($K_3$); and 4) green ($K_4$). Floating black blocks indicate anchor points ($P_{ij}$) coinciding with known data points intersecting the column. A light gray base layer is visible along the bottom (shown here as constant height, $I_{ij}$=I). Semi-transparent gray arrows indicate forces applied to each node ($F_{ij}$).
Figure 3A:
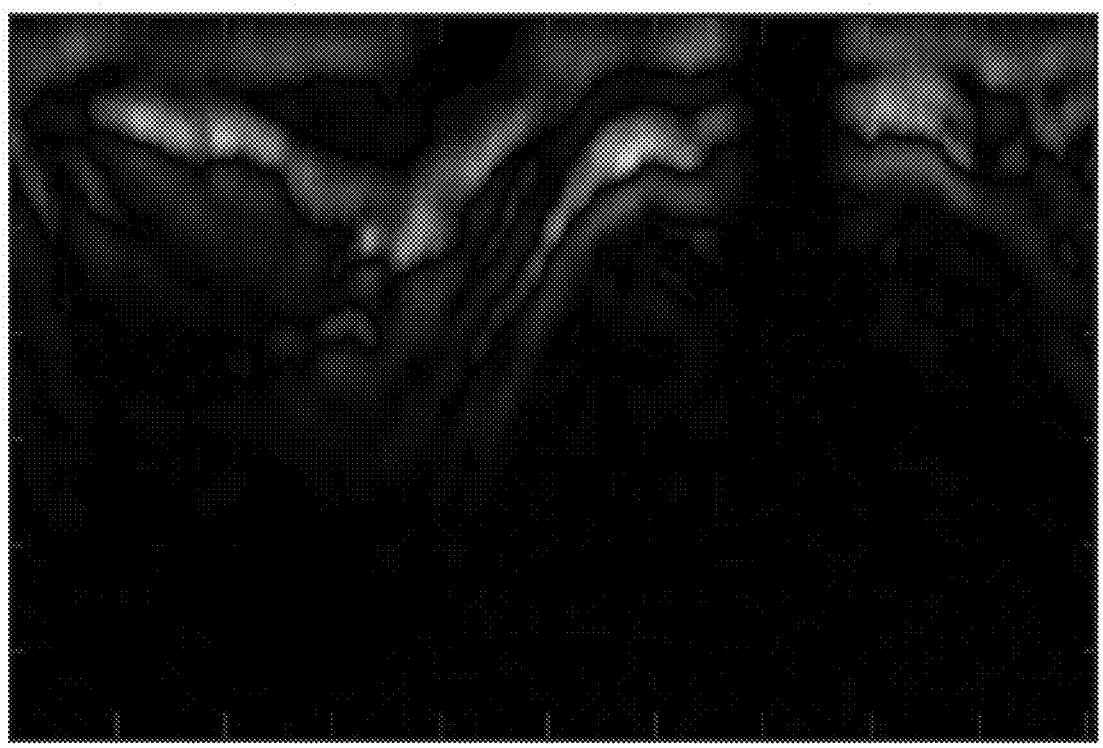
FIGS. 3A-3D show results of identifying the edge contours corresponding to the outer border.
Figure 3B:
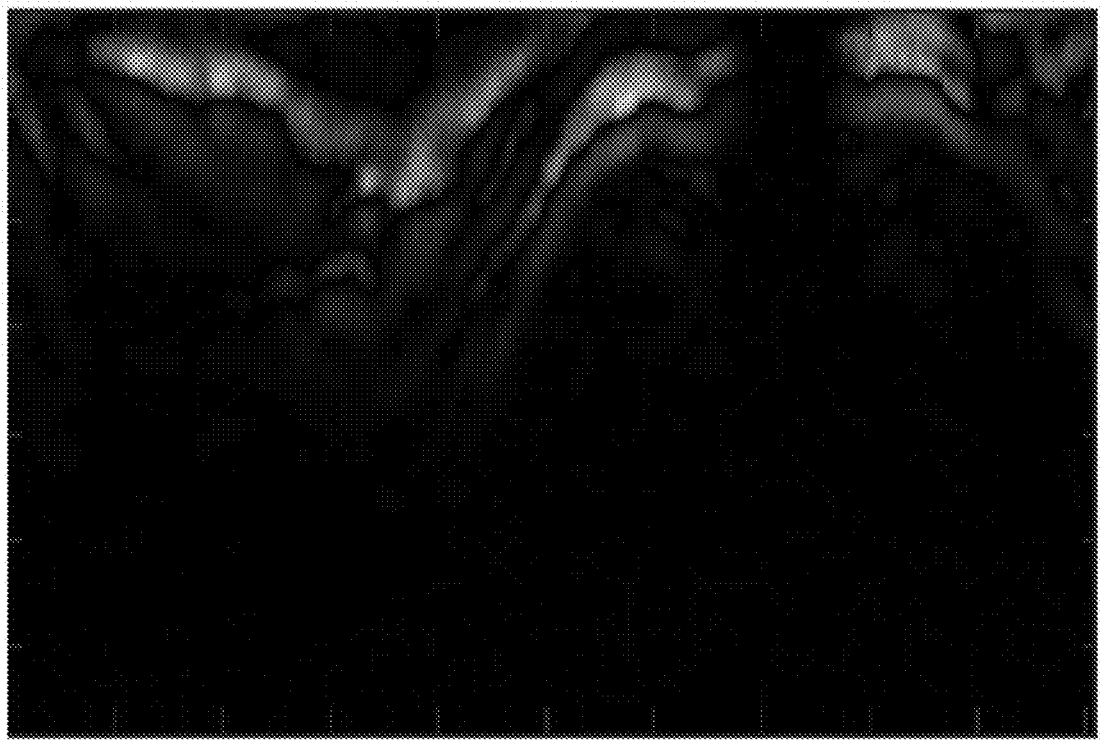
Figure 3C:
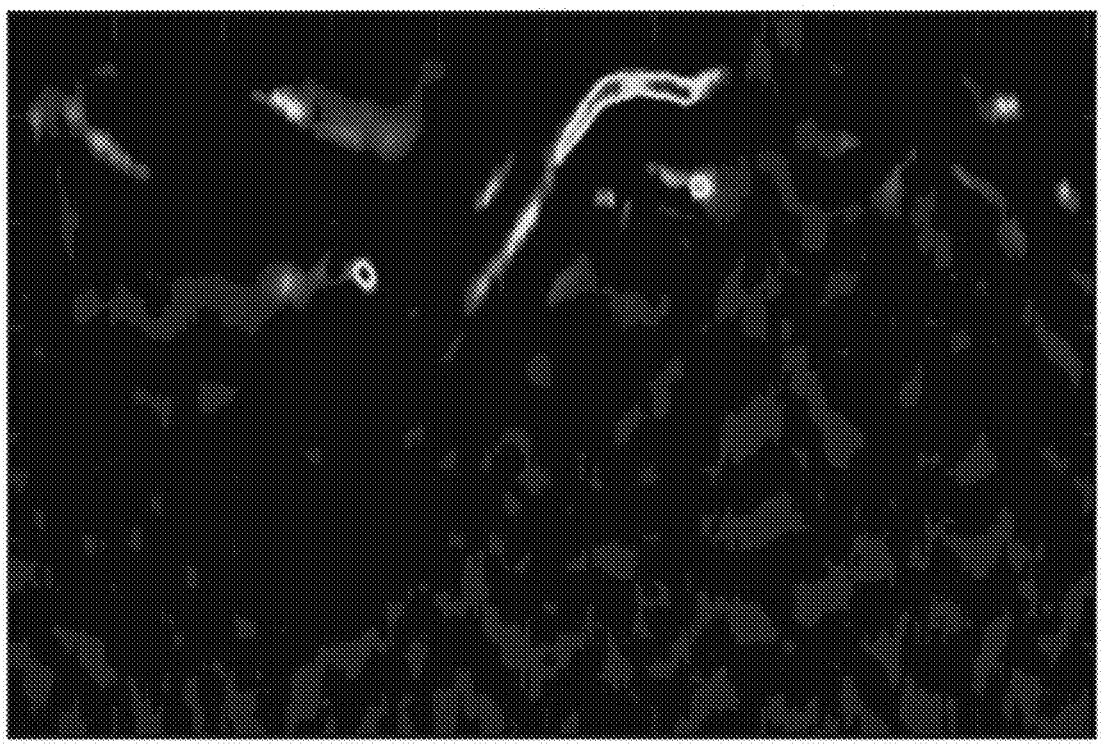
Figure 3D:

The global method is based upon a virtual anisotropic linear-elastic mesh of interconnected nodes and springs (FIG. 2). The aforementioned 3D discretized space, with an (i,j) index assigned to each distinct column, contains a single node which is constrained to that indexed column but free to translate in the $\hat{k}$-direction. This node represents the position of the fit surface at the given index, $S_{ij}$. Springs join adjacent nodes in the $\hat{i}$- and $\hat{j}$-directions. If there exists a known point $P_r$ in column (i,j)—$P_{ij}$—a position-fixed anchor may be placed at the location of $P_{ij}$. Stated otherwise, an anchor may be placed at (i,j,k), where index k is assigned the value of $P_{ij}$—$p_{ij}$. This anchor provides a set non-zero reference—a mechanical equivalent to a voltage source from ground. A base layer ($L_{ij}$) of variable height ($l_{ij}$) may also be present, and represents a nominal, average, or expected position. Springs oriented in the $\hat{k}$-direction connect the nodes either to anchors or, if not present in the given column, the base layer. Each class of springs—those adjoining nodes 1) within the plane j (i to i+1 and i−1), 2) between adjacent planes (j to j+1 and j−1), 3) to anchor points ($P_{ij}$), and 4) to the base layer ($L_{ij}$)—may be of different stiffnesses ($K_1$, $K_2$, $K_3$, and $K_4$, respectively, where K is the spring constant). It is noted here that any tolerance condition (1) is guaranteed to be met if anchored springs (class three) are infinitely stiff, i.e. $K_3 = \infty$, though this comes at a cost to smoothness as the node position is absolute and fixed to coincide with the anchor. The stiffness of each spring could also be, though was not in this implementation, assigned individually (for example, such that $K_3^{ij}$ is proportional to confidence in the anchor point position $p_{ij}$, or other approaches akin to a weighting function for smoothing weighted regression), but this would increase complexity of the system to an extent not deemed worthwhile in many cases given the additional variable features described next.

A unique force, $F_{ij}$, can be applied to each node. The magnitude and direction of this force may be calculated from original data, spatial position of the column, or any other desired source. This ability to incorporate additional information provides excellent flexibility in application. For example, in the application presented here, edges were less likely to be detected with increasing distance (displacement in $\hat{k}$-direction). Therefore, a spring mesh alone should underestimate the surface between the detected segments. However, by leveraging this a priori knowledge, forces can be applied that "inflate" the mesh outwards in regions in which no anchoring surface segments are detected.

With this structure in place, a system of linear equations can be derived that unambiguously solves for the position of each node. This system is solved for its equilibrium state, a condition described as:

$$\Sigma F = 0. \quad (2)$$

Because each node is necessarily constrained within its column:

$$\Sigma F_i = 0, \Sigma F_j = 0. \quad (3)$$

It therefore only remains to solve the balance of forces in the $\hat{k}$-direction. In this implementation, we used a common, generic Hookean linear-elastic spring model, in which restorative spring force ($F_{spring}$) is linearly proportional to its displacement (X) by a spring coefficient (K) defining its stiffness:

$$F_{spring} = -KX \quad (4)$$

With the model defined, the system of equations can be derived. Defining the initial lengths of springs to be 0, the forces exerted by the various springs on each node in the $\hat{k}$-direction are combined:

$$\sum F_k^{ij} = \\ K_1 d_{i-} \sin\theta_{i-} + K_1 d_{i+} \sin\theta_{i+} + K_2 d_{j-} \sin\theta_{j-} + K_2 d_{j+} \sin\theta_{j+} + F_{ij}^* + F_{ij} \quad (5)$$

$$\overline{F_{ij}^*} = \begin{cases} K_3(p_{ij} - S_{ij})\hat{k} & \text{if } \exists P_{ij} \\ K_4(l_{ij} - S_{ij})\hat{k} & \text{if } \not\exists P_{ij} \end{cases} \quad (6)$$

where d and θ are, respectively, the distance and angle between adjacent nodes, i and j of the subscript indicate the direction of adjacency (among or between planes, respectively), and +/−signs of the subscript indicate direction of adjacency (increasing or decreasing node number). As before, $p_{ij}$ is the height of the anchor point (tentative surface segment) in column (i,j), and $S_{ij}$ is the position of the node in the column, or alternatively, the position of the fit surface at index (i,j). Note that as the sine of angle θ is inversely proportional to the spring displacement d, $$\sin\theta_{i\pm} = \frac{S_{(i\pm 1)j} - S_{ij}}{d_{i\pm}}, \quad (7)$$

$$\sin\theta_{j\pm} = \frac{S_{i(j\pm 1)} - S_{ij}}{d_{j\pm}},$$

the above relationship (5) can be simplified to:

$$\Sigma F_k^{ij} = K_1(S_{(i+1)j} - S_{ij}) + K_1(S_{(i-1)j} - S_{ij}) + K_2(S_{i(j+1)} - S_{ij}) + K_2 \\ (S_{i(j-1)} - S_{ij}) + F_{ij}^* + F_{ij} = 0. \quad (8)$$

Rearrangement, grouping, and normalization by $K_1$ to reduce the number of parameters yields:

$$0 = -\left(2 + 2\frac{K_2}{K_1}\right)S_{ij} + S_{(i+1)j} + S_{(i-1)j} + \\ \frac{K_2}{K_1}S_{i(j+1)} + \frac{K_2}{K_1}S_{i(j-1)} + \frac{F_{ij}}{K_1} + \begin{cases} \frac{K_3}{K_1}(p_{ij} - S_{ij}) & \text{if } \exists P_{ij} \\ \frac{K_4}{K_1}(l_{ij} - S_{ij}) & \text{if } \not\exists P_{ij} \end{cases}. \quad (9)$$

If all N nodes are numbered sequentially, such that (i,j) corresponds to n and (i,j+1) corresponds to (n+p), and N is equal to p×q, the full system of equations can be expressed as Ax=b, where A is a sparse N×N square matrix:

$$A_{nn} = -2 - 2\frac{K_2}{K_1} - \begin{cases} \frac{K_3}{K_1} & \text{if } \exists P_{ij} \\ \frac{K_4}{K_1} & \text{if } \not\exists P_{ij} \end{cases}; \quad (10)$$

$$A_{n(n\pm 1)} = 1; \quad (11)$$

$$A_{n(n\pm p)} = \frac{K_2}{K_1}. \quad (12)$$

Furthermore, x is a vector of node positions:

$$x = \begin{bmatrix} s_1 \\ \vdots \\ s_N \end{bmatrix}. \tag{13}$$

Finally, b is a vector with the following entries:

$$b_n = -\frac{F_n}{K_1} - \begin{cases} \frac{K_3}{K_1} \text{ if } \exists P_{ij} \\ \frac{K_4}{K_1} l_{ij} \text{ if } \not\exists P_{ij} \end{cases}. \tag{14}$$

Multiplying both sides of the equation by the inverse of matrix A, the position of all N nodes can be solved simultaneously with a single operation with computation complexity $O(N^{1.5})$:

$$x = A^{-1} b. \tag{15}$$

This approach may be used in Cartesian coordinates for a non-folded surface or, as in the present application, a cylindrical surface expressed in cylindrical (polar) coordinates. When working in cylindrical coordinates, edge continuity is achieved by connecting nodes at the start and end of each plane j, as shown with the dashed-line springs (FIG. 2). Other boundary conditions can also be readily enforced.

As described in the following sections, this methodological approach for constructing a continuous surface from incomplete information was applied in OCT to 1) smooth a contour in which tentative locations of the entire surface are known, and 2) construct a surface when only limited fragments of the surface have been tentatively located.

OCT Wall Detection

The spring mesh surface construction method was applied to automatically and fully delineate the borders of a diseased vessel in OCT images. The approach was implemented using the MATLAB software (MATLAB R2017a, The MathWorks, Inc., Natick, Mass., USA).

Lumen Detection and Smoothing

In certain embodiments, initial detection of the lumen followed a procedure used by Athanasiou et al. ("Methodology for fully automated segmentation and plaque characterization in intracoronary optical coherence tomography images," J. Biomed. Opt., 19(2):026009 (2014), which is incorporated by reference in its entirety). In brief, image data were converted to binary format with Otsu's thresholding method, common artifacts (i.e. catheter sheath and guidewire backscattering) were purged, and the most proximal point in each column (non-zero point of lowest radial distance) was retained. Simple two-dimensional (2D) smoothing was performed on these points, and they were then connected through linear interpolation to points in laterally-adjacent columns with straight lines, resulting in a continuous contour within each frame. In various embodiments, other procedures may be used to identify and delineate the inner lumen surface, including for example the procedure disclosed below based on applying bilateral filtering and a K-means algorithm.

While minimally smoothed, the resulting lumen surface was not necessarily continuous in three dimensions (e.g. longitudinally). To further smooth the lumen as a continuous 3D surface, in some embodiments an anisotropic linear-elastic mesh was fit to the points using the approach described herein. In these embodiments, each column contained an anchor point ($P_{ij}$), which eliminated the need for parameters defining the base surface ($L_{ij}$) and the spring coefficient for connections between nodes and this surface ($K_4$). No force function was applied in this scenario, eliminating a third parameter ($F_{ij}$). The remaining parameters, $K_2/K_1$ and $K_3/K_1$, were determined by minimizing the sum of radial distance magnitudes between the node equilibrium positions and the validation annotations of the lumen:

$$\min_{\frac{K_2}{K_1}, \frac{K_3}{K_1} \geq 0} \sum_{r=1}^{N} \left\| S\left(\frac{K_2}{K_1}, \frac{K_3}{K_1}, P_r\right)_{P_r^*} - P_r^* \right\| \tag{16}$$

where P* are the validation annotation positions. (See Validation section for more information on these annotations.) Minimization was achieved by a constrained optimization nonlinear programming solver employing the interior-point algorithm. Each iteration step was calculated through factorization, and forward finite differences were used to estimate the objective gradients; the Broyden-Fletcher-Goldfarb-Shanno algorithm was employed to approximate the Hessian matrix. The iterative process terminated when changes in parameters decreased beyond $10^{-10}$.

Outer Border Segment Detection

Identification of the outer border candidate edges drew upon image enhancement and edge detection approaches specifically adapted for this application, as described further below. In brief, in certain embodiments polar images were first flattened relative to the lumen to better horizontally align layers of the same radial depth, improve filtering efficacy, and ease layer boundary identification through improved shape consistency. Contrast enhancement and image compensation were performed on the flattened image, speckle noise was reduced through 3D median filtering, Sobel-Feldman edge-detection kernels detected grayscale gradients, and skewed distribution kernels—specially designed to account for the nominal size of the media layer—were utilized in convolution to identify the radial light-dark-light intensity transition indicative of the media layer, the inner surface of which was considered in this embodiment as the outer border of the vessel.

Visible outer border segment detection followed lumen detection. Using the detected lumen contour, in various embodiments polar images were flattened using techniques developed for retinal OCT layer segmentation. A compensation and contrast enhancement algorithm employing exponentiation was next applied to the flattened polar images using methods proposed by Girard et al. ("Shadow removal and contrast enhancement in optical coherence tomography images of the human optic nerve head," Invest. Ophthalmol. Vis. Sci., 52(10):7738 (2011), incorporated by reference herein in its entirety). To enhance the image, a transformation was used in which contrast enhancement through exponentiation precedes image compensation:

$$HD\{I^n(z)\} = \frac{I^n(z)}{2 \int_z^\infty I^n(u) du} \tag{24}$$

where HD is a compensating transformation operator for a given exponentiated column of the image, I is pixel intensity, n is the exponential factor, and z is (propagating beam) depth, in this application equivalent to radial depth r. As in the referenced study, an exponential factor of 2 was used. The discretized implementation of the algorithm described by Girard et al. was utilized.

Speckle noise was enhanced during the transformation, so simple median filtering was performed to de-noise the resulting compensated and unattenuated form of the images. As the flattened polar images were arranged consecutively in three-dimensional (3D) space, with pixels functioning as voxels, filtering was performed with a 3D kernel to leverage information from adjacent frames and minimize the impact of local artifacts.

To provide appropriate boundaries for filtering around the ends of the image, frames were concatenated on each side with their adjacent frames. Because OCT data is acquired in a continuous helical sweep, rather than at discrete incremental positions as suggested by its normal display, these adjacent edges truly represent the boundaries of the frames and provide a continuation of the image data along the frame edges. Symmetric boundaries were implemented for the leading and trailing edges of the first and last frames, respectively.

The process of detecting edges associated with the outer, border began with the generation and convolution of a 3×3×3 Sobel-Feldman kernel in the radial (vertical) direction with the image volume. The vessel outer border is characterized by radial light-dark-light intensity (grayscale value) transitions. To identify these transitions in the image, convolutions with vertical, 1-dimensional (1D) kernels oriented in the radial direction were performed to calculate the difference between the Sobel-Feldman convolution results above and below each pixel. However, the thickness of the characteristic dark band of the media layer—the distance between the light-to-dark and dark-to-light transitions—varies. Therefore, in certain embodiments the kernels were designed as a normalized combination of two Gaussian distributions with peaks separated by the nominal 200 μm (average thickness of normal wall). Combining two Gaussian distributions with different standard deviations allowed for a skewed resultant distribution—reflecting the skewed distribution of media thicknesses—with more spatial control than alternative asymmetric distribution functions, such as "chi-squared" or "log normal" distributions. If the proximal convolution yielded a positive result (indicative of a characteristic light-to-dark transition above) and the distal convolution yielded a negative result (indicative of a characteristic dark-to-light transition below), the pixel was considered a candidate media location and the product of the two convolution outputs for that pixel was calculated (FIGS. 3A-3D).

Segments of the outer border were then identified from the matrix of convolution products through a 3D region-growing scheme that extracted segments including values of particularly high magnitude, indicative of prominent, well-defined transition patterns. The 2D properties of resulting regions' intersections with each given plane are calculated to help eliminate non-feasible boundaries—regions with small major-to-minor axis length ratios or orientations beyond −30° to 30° were removed.

As the standard Sobel-Feldman and Gaussian distribution kernels do not capture edges oriented at an angle as well as those that are horizontal, off-axis angles were substantially disadvantaged in the global region-growing. To overcome this shortcoming and capture those angled border segments, the same edge identification procedures described above were repeated with Sobel-Feldman kernels and Gaussian distribution kernels oriented at both 45° and −45°. Subsequent feasibility criteria were modified to accept regions with orientations between 15° and 75°, and −15° and −75°, respectively. Edges detected with the standard and off-axis procedures were combined (through a logic "OR" operation) to form a 3D binary representation of the detected segments of the outer border in the flattened 3D image volume.

The entire boundary-identification procedure was performed in the concatenated volume to avoid erroneously penalizing or disadvantaging segments along the edge of a frame, as criteria (i.e. size/area, major-to-minor axis length ratio, and orientation) could be skewed for sub-segments of boundaries that may, in fact, wrap to the opposite side of the polar image. Only after these procedures were complete was the concatenated volume reduced back to the central, original volume.

Surface Fitting

Figure 4:
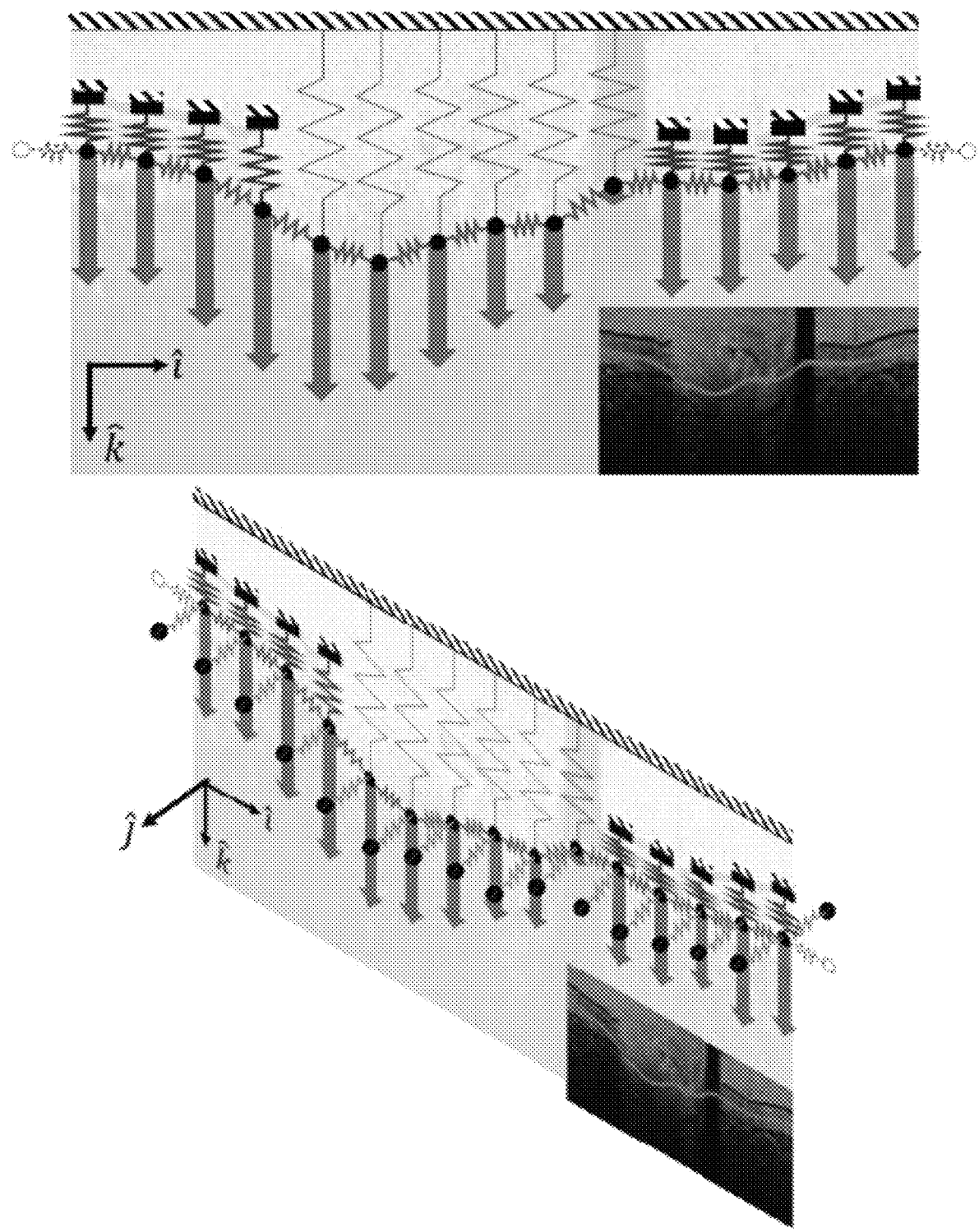
FIG. 4 shows a diagram illustrating implementation of the surface fitting method in this application within each frame (top panel) and between frames (bottom panel); for the diagrams in each of the top and bottom panels, the outer wall of the vessel is on the bottom and the inner wall of the vessel (the lumen) is on the top. The detected (candidate) edges served as anchor points, while the proximal side of the flattened image (i.e. the lumen) acted as the base layer. Each uniformly-spaced node was constrained to displacement in the radial (k) direction, and was acted upon by an outward force proportional to the sum of column intensity values. Each node was connected to the nearest nodes in each direction, and the nodes on either end of a frame were connected to ensure continuity in cylindrical coordinates. Note that, while 15 nodes are illustrated here for clarity, each of the 504 columns in every frame contained a node. Schematic representation and color correspondence as in FIG. 2.

Given border segments detected in 3D space, it was necessary to fill gaps between detected segments and ensure continuity from frame to frame. Continuity and smoothness are inherently observed in nature, and cross-sectional area does not vary considerably in adjacent frames. It was therefore necessary to fit a smoothed surface with the available information of tentative partial surface location. This was accomplished using the novel anisotropic linear-elastic mesh surface fitting method disclosed herein (e.g. see FIG. 4).

In this application, only columns in which border segments were detected include an anchor point ($P_{ij}$). It was observed that base surface position could be uniformly set to 0 ($I_{ij}=0$) with minimal impact on performance, so this was used to decrease complexity and reduce arbitrary offsets. Here, a force function was selected to apply a unique force to each node that incorporated information from the original imaging information:

$$F_{ij} = \alpha \Sigma I(i,j) \tag{17}$$

where $\alpha$ is a scaling coefficient, I is the pixel intensity of the original image, and as before, $F_{ij}$ is node-specific force applied to the mesh. Sum of pixel intensity was utilized because thick, high-intensity regions often indicate the presence of a thick, diseased intima, which corresponds to greater outer border depth. This scheme also prescribes near-zero force in regions obscured by the guidewire shadow, a desirable feature resulting in smooth interpolation-like continuity with adjacent regions.

While multiple force functions were tested, including those proportional to lumen cross-sectional area or simply a constant, the sum of intensities in each column yielded the best result. The non-fixed parameters for this system, $K_2/K_1$, $K_3/K_1$, $K_4/K_1$, and $\alpha/K_1$, were determined using the aforementioned constrained optimization nonlinear programming solver by minimizing the sum of radial distance magnitudes between the node equilibrium positions and the validation annotations of the outer border:

$$\min_{\frac{K_2}{K_1}, \frac{K_3}{K_1}, \frac{K_4}{K_1}, \frac{\alpha}{K_1} \geq 0} \sum_{r=1}^{N} \left\| S\left(\frac{K_2}{K_1}, \frac{K_3}{K_1}, \frac{K_4}{K_1}, \frac{\alpha}{K_1}, I, P_r\right)_{P_r^*} - P_r^* \right\| \tag{18}$$

where P* are the validation annotation positions. (See Validation section below for more information on these annotations.)

Interpolation and surface-fitting to the detected surface segments were also conducted with existing methods for performance comparison.

Surface Reconstitution and Coordinate Conversion

After the equilibrium node positions were calculated, the resulting surface was reconstituted to the non-flattened state by shifting each column distally by the radial distance of the lumen in the original image (reversing the original flattening process; see the Outer Border Segment Detection section). The reconstituted surface was finally converted from the cylindrical to Cartesian coordinate system—transforming the open surface into a wrapped cylindrical surface—using the standard transformation.

Validation

The autonomous border detection method was validated through direct comparison to the manual annotations made by expert interventional cardiologists in the same OCT clinical dataset. An average border annotation of two experts was determined by taking the mean radial distance of both annotations from the center of the image around the perimeter in each frame (as disclosed in Athanasiou et al., see above). Annotations were compared in 724 frames from 7 unique pullbacks (series of images) acquired from the same number of unique patients.

The detected borders achieved with the presented methodology were then overlaid on the average OCT border annotations (considered ground truth), and the following parameters were calculated:

$$\text{Sensitivity} = \frac{TP}{TP+FN} \times 100 = R_{over} \times 100; \quad (19)$$

$$\text{Specificity} = \frac{TN}{FP+TN} \times 100; \quad (20)$$

$$\text{Jaccard Index} = \frac{TP}{TP+FP+FN} \times 100; \quad (21)$$

$$\text{Dice Index} = \frac{2TP}{2TP+FP+FN} \times 100; \quad (22)$$

$$R_{nonover} = \frac{FN+FP}{TP+FN} \quad (23)$$

where TP are true positives, TN are true negatives, FP are false positives, and FN are false negatives. Here, TP are considered those pixels enclosed by both the algorithm results and expert annotations, TN are those pixels of the full 500×500 pixel image enclosed by neither annotation, FP are those pixels enclosed by only the algorithm result, and FN are those pixels enclosed by only the expert annotation. The ratios of overlapping ($R_{over}$) and non-overlapping ($R_{nonover}$) areas between the algorithm results and expert annotations (eqns. (19) and (23), respectively) were defined similar to Athanasiou et al. (see above) to represent sensitivity and specificity of automated image segmentation in a way that is not skewed and inflated by the image size, particularly when the region of interest is only a subset of the actual image (as in OCT). The distribution of the absolute radial distance between the expert annotations and algorithm results was also determined, the coefficient of determination ($R^2$) was calculated for the resulting cross-sectional areas, and Bland-Altman analysis of the delineated cross-sectional areas was performed.

The autonomous border detection method was further validated through indirect comparison to the manual annotations made by an expert interventional cardiologist in a corresponding intravascular ultrasound (IVUS) clinical dataset. IVUS, which has lower resolution but greater penetration depth than OCT and is well validated for identification of vessel outer wall, was treated as the gold standard. However, evaluation criteria for validating between modalities is limited—only differences between areas enclosed by the annotation results and expert tracings and their $R^2$ could be calculated, and Bland-Altman analysis of the areas was performed.

Dataset

Seven patients who underwent invasive angiography and had one or more coronary stenoses of at least intermediate severity were included in the study. The study was approved by the Ethics Committee of the institution and all patients gave informed consent.

Angiography was performed following a standard protocol, using radial or femoral access. After the diagnostic angiography, 200 µg of intracoronary nitroglycerin and 5,000 IU of unfractionated heparin were infused. Investigators used the C7-XR FD-OCT optical frequency domain intravascular imaging system and the DragonFly catheter (St. Jude Medical, Lightlab Imaging Inc., Westford, Mass., USA). This imaging system offers a maximum frame rate of 100 frames per second, 500 lines per frame, a scan diameter of 10 mm, and axial resolution of 15 µm. The monorail imaging catheter was advanced distal to the target lesion. The automated pullback was performed at 20 mm/s (system nominal pullback speed) while the blood was removed by a short injection of iso-osmolar contrast at 37° C. through the guiding catheter. The optimal volume/time intracoronary infusion of contrast was tested to achieve a complete blood clearance in the vessel lumen.

Per protocol, IVUS imaging of the coronary segments imaged with OCT was also conducted. The IVUS catheter, a Revolution 45 MHz rotational IVUS imaging catheter (Volcano Inc., Rancho Cordova, Calif., USA) was placed at the same distal position as the OCT catheter, using as reference a fiduciary anatomical point such as a bifurcation or a calcification spot. An angiographic acquisition was obtained with the imaging catheter in the distal position to confirm matching points for the IVUS and OCT starting runs. An automated motorized pullback at 0.5 mm/s was performed.

Images were digitally stored for off-line analysis, and all imaging data sets were completely anonymized and transferred to the core lab for analysis. For the purposes of this study, OCT datasets in which blood removal was found post hoc to be grossly insufficient were not utilized. Delimiting segments of useable pullbacks captured prior to or following injection of contrast were similarly excluded. To ensure the same vessel segments were analyzed with both techniques, matching of the OCT and IVUS pullbacks was performed using landmarks such as side branches and other anatomical features, thereby providing frame-by-frame correspondence. Experts were thereafter blinded to the correspondence of imaging files.

General Performance

As the method is 3D and global for a given pullback, run time was positively, but non-linearly, related to the number of frames in each analyzed pullback. Average execution times for the major steps—executed in certain embodiments on a machine running Intel Xeon processors with 12 cores (2.80 GHz) and 12 GB RAM—are reported in Table I. Execution time is dominated by initial lumen and visible outer border segment detection, while the lumen smoothing and surface fitting steps are exceptionally fast (2.74±0.28 ms and 40.2±7.5 ms per frame, respectively). Conversion from polar to Cartesian coordinates is also a significant contributor to the run time (not shown). The one-time optimization of the inner and outer border surface fit parameters took 7.8 and 10.1 minutes, respectively, to execute.

TABLE I

RUN TIMES FOR MAJOR STEPS

| Step | Average Time per Frame (±SD) |
|---|---|
| Initial Lumen Detection | 4.2 ± 1.5 |
| Lumen Smoothing | 0.00274 ± 0.00028 |
| Image Flattening | 0.0064 ± 0.0013 |
| Edge Detection | 5.35 ± 0.85 |
| Surface Fitting* | 0.0402 ± 0.0075 |
| *Setup* | *0.0363 ± 0.0070* |
| *Solve* | *0.0039 ± 0.0013* |

Times are expressed in seconds as average and standard deviation (SD) across pullbacks.
*The "Surface Fitting" step total is presented along with its two contributing sub-steps (i.e. the italicized times do not represent additional run time)

As a consequence of the patient inclusion criteria that sought high plaque burden vessels, the outer wall was often poorly visualized. While the experts were able to identify sufficient segments of the outer border to confidently estimate the full border in most frames, the edge detection process described here identified segments of the outer border in only 57% of columns (A-lines). It is noteworthy that these sparse detected edges are the anchor points ($P_r$) for the subsequent surface fit.

Figure 5A:
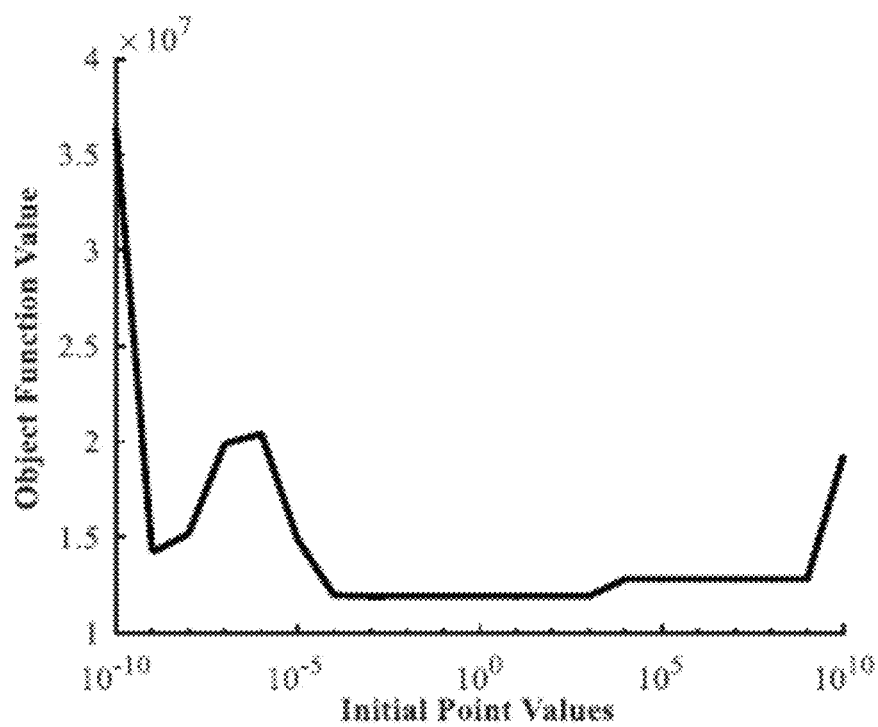
FIGS. 5A-5C show tests of (outer border) optimization stability as the initial value of the parameters was varied. Outputs were stable over a range of values from $10^4$ to $10^3$.
Figure 5B:
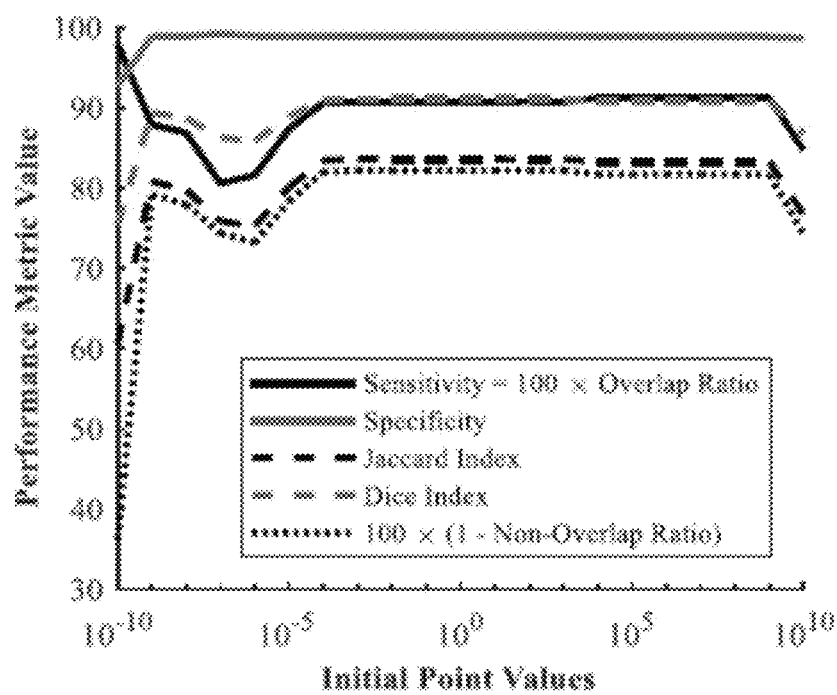
Figure 5C:
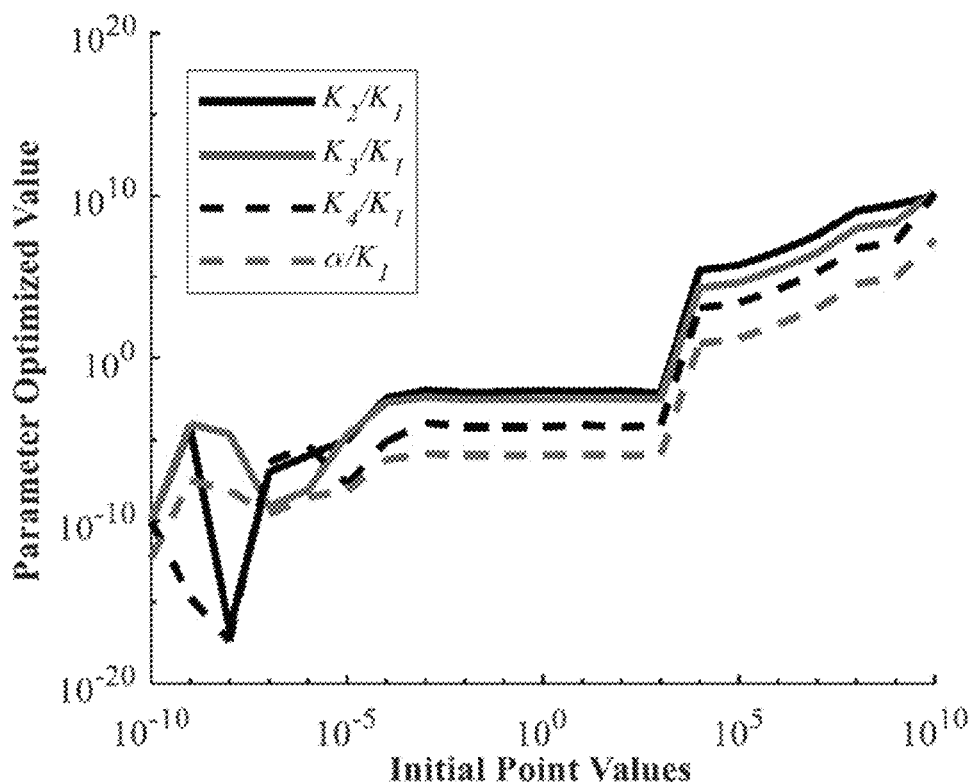
Figure 6:
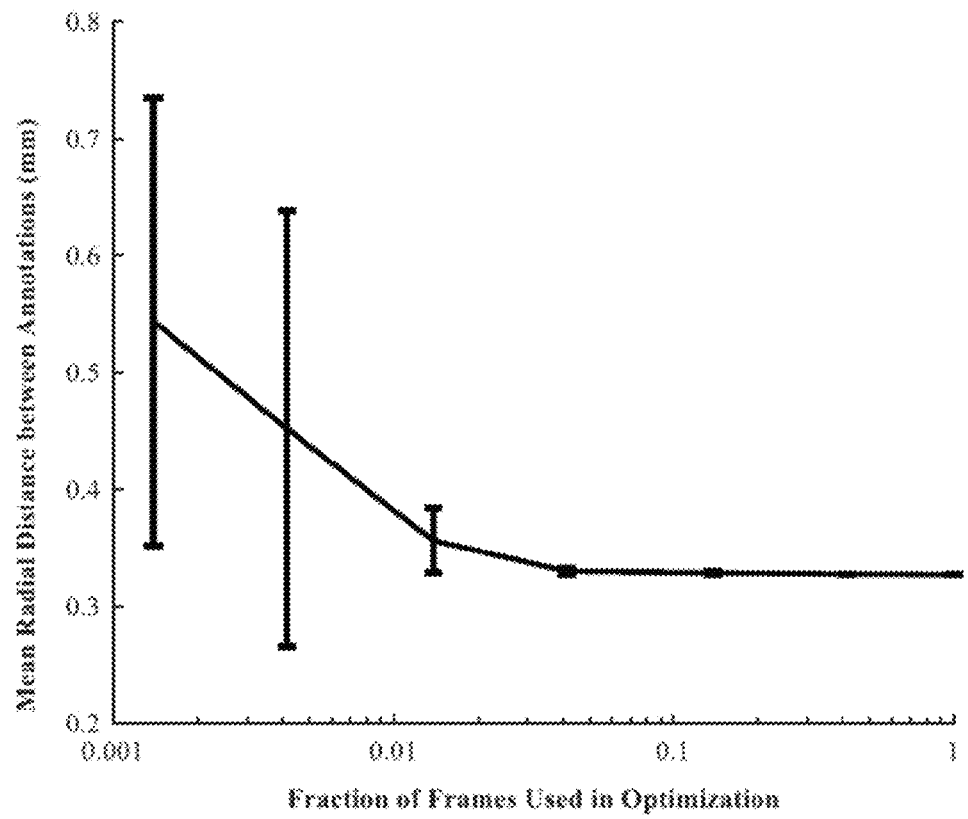
FIG. 6 shows tests of outer border optimization convergence as the number of frames used in the optimization was increased. Performance metric: mean radial distance between algorithm and expert annotations.
Figure 7A:
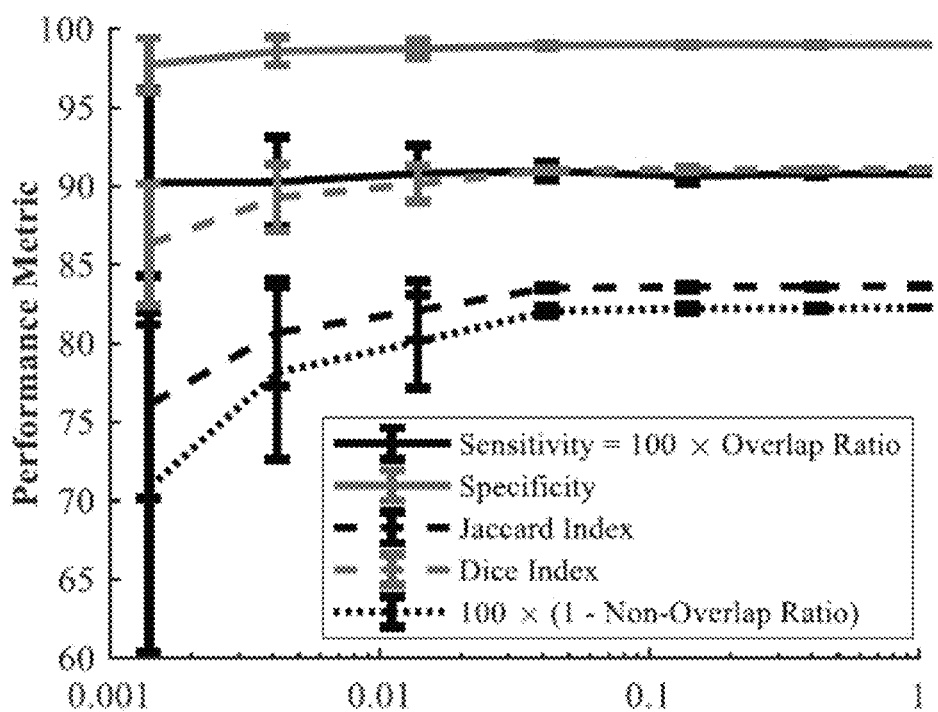
FIGS. 7A and 7B show a test of (outer border) optimization convergence as the number of frames used in the optimization was increased.
Figure 7B:
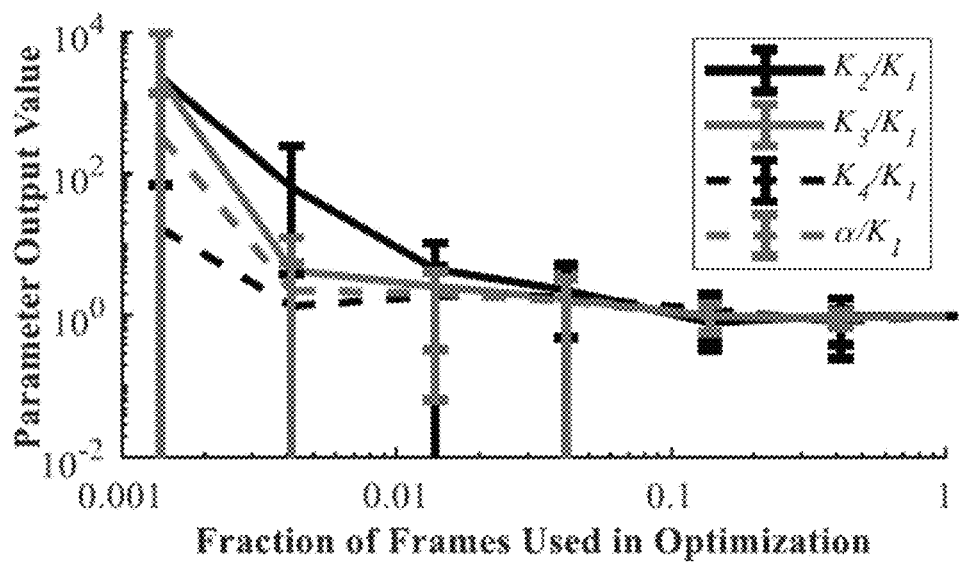

Optimization was tested for stability with respect to the initial value to ensure robustness and identification of global minimum. For the more challenging outer border, the optimization was stable over 7 orders of magnitude in the range of initial conditions, and the optimal output identified over 20 orders of magnitude of initial value was produced within this stable range (FIGS. 5A-5C). The process was also tested for convergence with respect to the number of frames used in the optimization. As seen in the performance curves (FIGS. 6 and 7A), all performance metrics improved with increasing numbers of frames included in the optimization, stabilizing around 30 frames (meaning that performance improved only slightly when the number of frames used for optimization was increased from 30 to the full 724). Output parameter values largely converged in the same manner (FIG. 7B). Again noteworthy are not only convergence as frame numbers increase, but profound reduction in error and variability (which on the logarithmic scale of FIG. 7B appear to extend infinitely in the negative direction at high values). When provided with the same inputs, the optimization algorithm consistently arrived at the same results. Similar testing was performed for the less complex lumen smoothing operation optimization, which demonstrated even greater stability (results not shown). Having shown method stability and convergence, all frames were used in the optimization with initial values for all parameters set to $10^{-3}$, which produced optimal results during the initial condition sensitivity testing. Final optimal parameters for the inner (lumen) border surface fit were: $K_2/K_1=6.74\times10^{-3}$; and $K_3/K_1=2.02\times10^{-2}$. For the outer border surface fit, the final optimal parameters were: $K_2/K_1=1.09\times10^{-2}$; $K_3/K_1=3.92\times10^{-3}$; $K_4/K_1=1.10\times10^{-4}$; and $\alpha/K_1=1.36\times10^{-6}$.

Optimization Stability

Optimization was tested for stability with respect to initial value to ensure robustness and identification of global minimum. For each test, all parameters were identically set to the same initial value ("initial point value") prior to object function minimization. Optimization of the surface fit system for the outer border was stable as the initial values were varied over 7 orders of magnitude (FIGS. 5A-5C). The most optimal output (resulting in the lowest object function value over the 20 orders of magnitude tested) resulted from an initial value ($10^{-3}$) within this stable range.

Optimization Convergence

Optimization was tested for convergence with respect to the number of frames used to determine the influence of the data used in the optimization on the outcome (optimal parameter values). Ten sets of randomly-selected frames were tested for each number of frames evaluated (FIGS. 6, 7A, and 7B). FIGS. 7A and 7B illustrate the trends of the various individual performance metrics and parameters as increasing numbers of randomly selected frames are used in the evaluation of the objection function. The object function value—normalized by number of frames evaluated in its calculation—achieved a downward trend as the number of frames increased (FIG. 6). As hoped, both performance metrics and system parameter values converged as the number of frames used in the optimization increases to around 30 (around 4%, or $4\times10^{-2}$, of the 724 total frames available; FIGS. 6, 7A, and 7B). Also of note is the absence of variability when optimization was performed multiple (10) times with all frames, demonstrating stability of the underlying optimization framework.

Lumen Detection

Figure 8A:
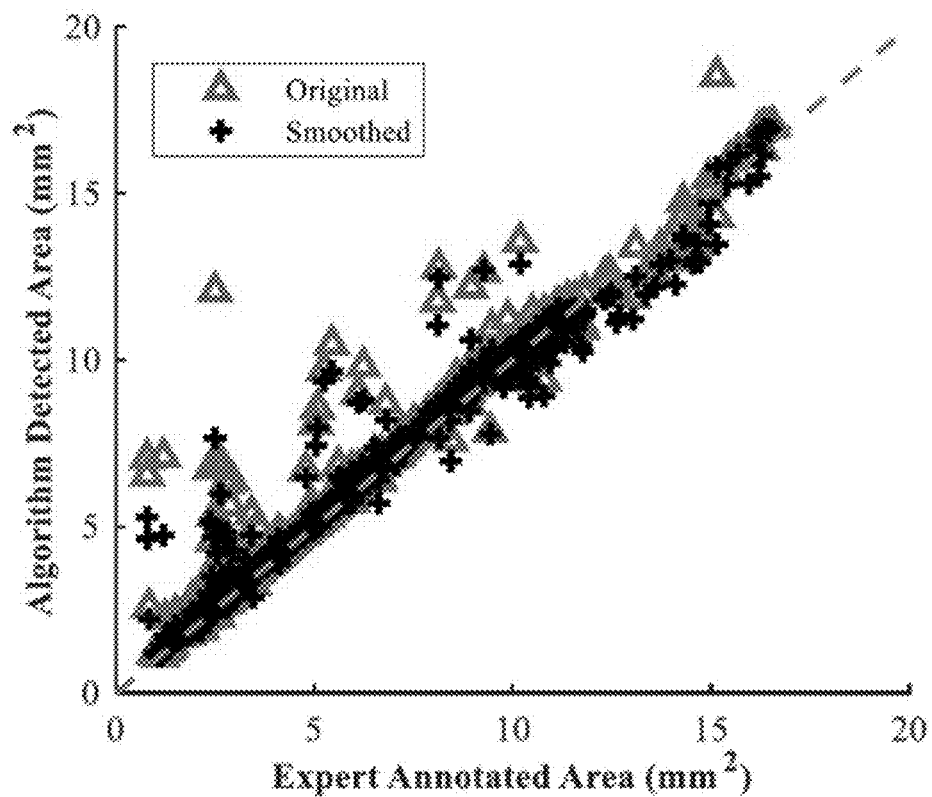
FIGS. 8A and 8B show a comparison of algorithm detection and human expert annotation of the lumen.
Figure 8B:
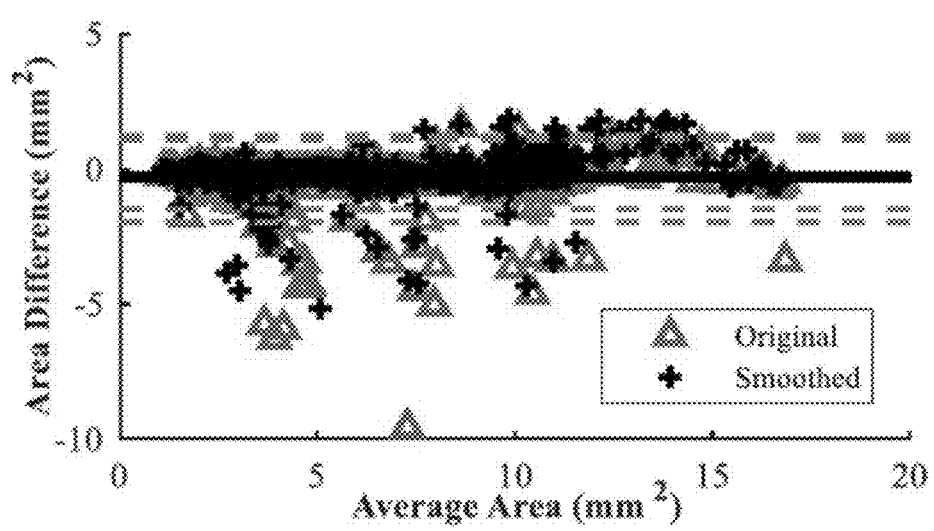

The areas delineated by the inner (lumen) border results were first assessed. Here, the initial position of the lumen was determined for each column, and the surface-fitting approach presented above was used just for its smoothing capability. FIGS. 8A and 8B show the error (FIG. 8A) and Bland-Altman (FIG. 8B) plots comparing the algorithm to the average expert annotations. Direct comparison of overlapping regions delineated by the human expert annotations and algorithm results in OCT were made as outlined in the Validation section. The original lumen trace differed from that of the human expert by 0.12±0.43 mm (average±standard deviation; 0.01±0.44 mm overall, i.e. not absolute distance); the smoothed lumen trace differed by 0.11±0.35 mm, on average (0.00±0.36 mm overall). Sensitivity, specificity, Jaccard index, Dice index, $R_{over}$, and $R_{nonover}$ parameters are provided for the lumen before and after the smoothing surface-fit operation (Table II). The mean and median percent change in frame-to-frame lumen area of the final smoothed lumen contours (7.5% and 4.4%, respectively) were between that of the human experts (6.0% and 3.8%, respectively) and that of the original lumen contours (9.3% and 5.0%, respectively).

TABLE II

PERFORMANCE METRICS COMPARING REGIONS DELINEATED BY INNER BORDER AS ORIGINALLY DETECTED AND AFTER SMOOTHING SURFACE FIT

| Metric | Original | Smoothed (Surface Fit) |
|---|---|---|
| Sensitivity | 98.46 | 97.54 |
| Specificity | 99.47 | 99.59 |
| Jaccard Index | 91.51 | 92.16 |
| Dice Index | 95.57 | 95.92 |
| $R_{over}$ | 0.9846 | 0.9754 |
| $R_{nonover}$ | 0.0914 | 0.0830 |

Inner Border = Lumen Border

Outer Border Detection

Figure 9:
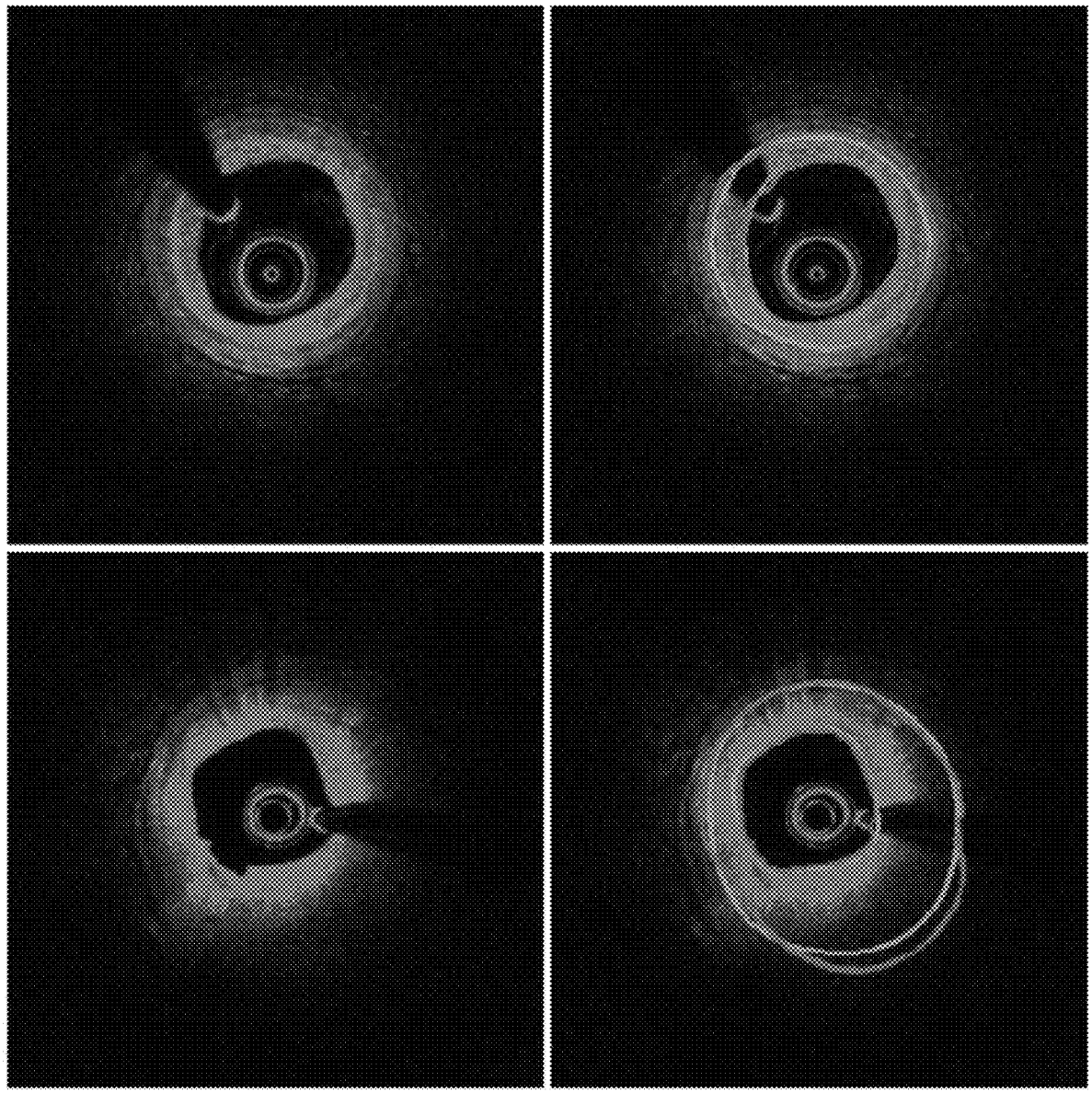
FIG. 9 shows two examples of fully delineated frames (top panels and bottom panels). Green tracings (top right and bottom right panels) represent the expert annotation, while magenta tracings (top right and bottom right panels) depict the algorithm result. Note that the majority of the outer border is not visible in the second frame (bottom panels).
Figure 10:
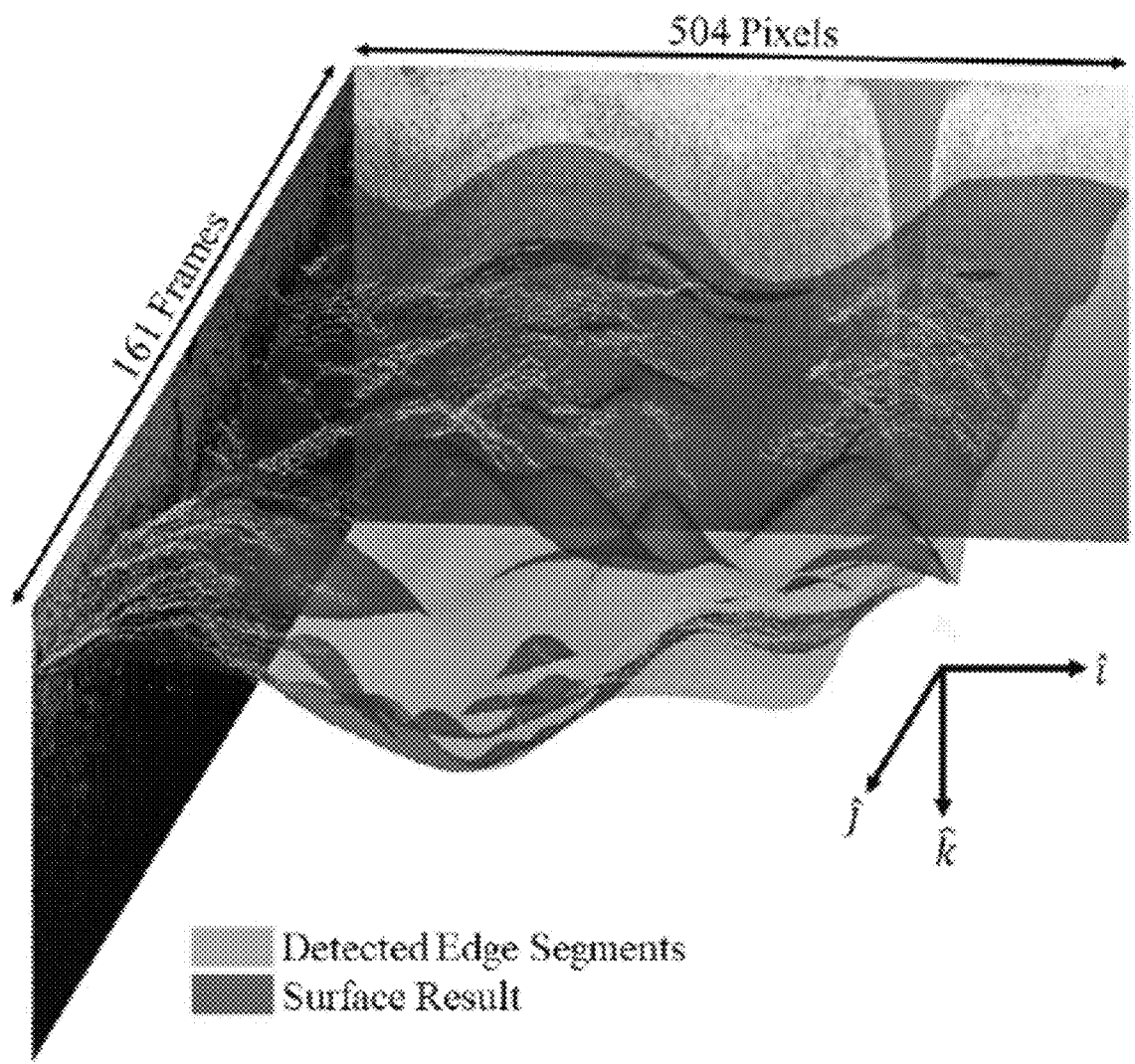
FIG. 10 shows the outer border surface as detected by the algorithm in one patient. Images illustrate bounding slices of the flattened image volume. The magenta surface represents the algorithm result; cyan segments represent the detected outer border edge segments, which were used to calculate the surface. Note that the segments tend to appear closer to the lumen surface, where penetration depth has less of an impact on visibility, but the surface contour is not limited to this superficial region.
Figure 13:
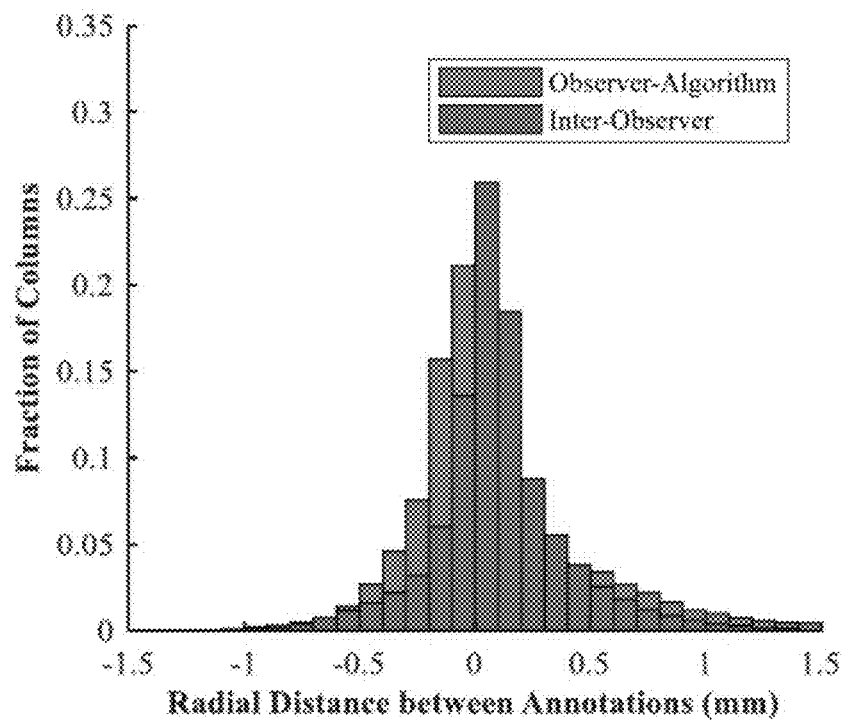
FIG. 13 shows a comparison of outer borders through measurement of difference in radial depth of tracings. Mean difference between the tracing radial depth of the average expert and algorithm was 0.09±0.53 mm (mean±standard deviation; 0.33±0.43 mm absolute distance). Mean difference between the tracing radial depth of the two experts was 0.10±0.30 mm (0.21±0.23 mm absolute distance).

The full area delineated by the outer border as determined by experts and the algorithm (FIG. 9) was also assessed. The outer border was determined with the surface-fitting method presented here using only partial detected contour segments (FIG. 10). In directly comparing the tracing of the outer border made by the algorithm to that of the human experts (FIG. 13), the mean difference between the tracing radial depths was 0.09 mm with a standard deviation (SD) of 0.53 mm (0.33 mm with a SD of 0.43 mm for the absolute difference/distance).

Figure 12A:
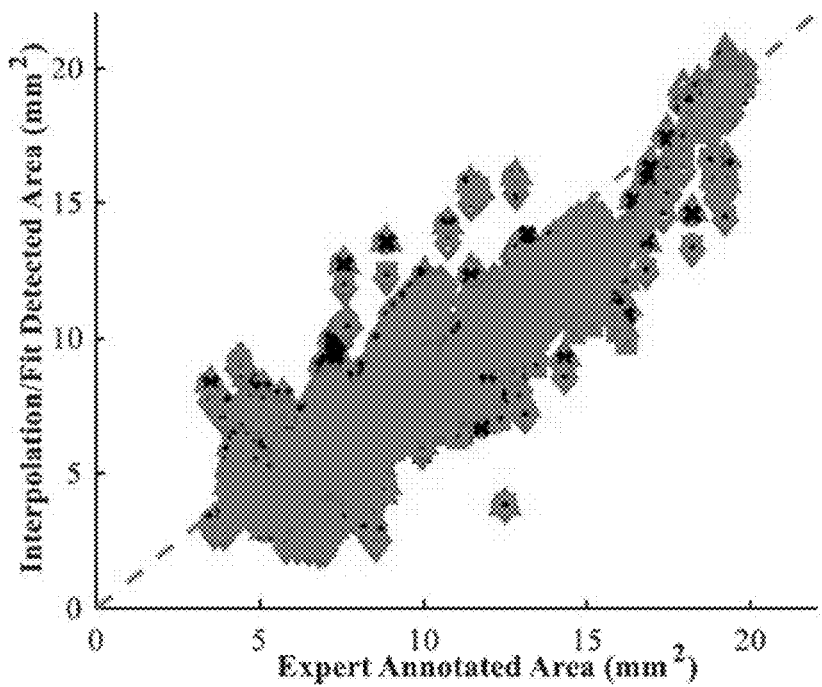
FIGS. 12A and 12B show a comparison of areas resulting from existing interpolation and surface fit methods and human expert annotations of the outer border.
Figure 12B:
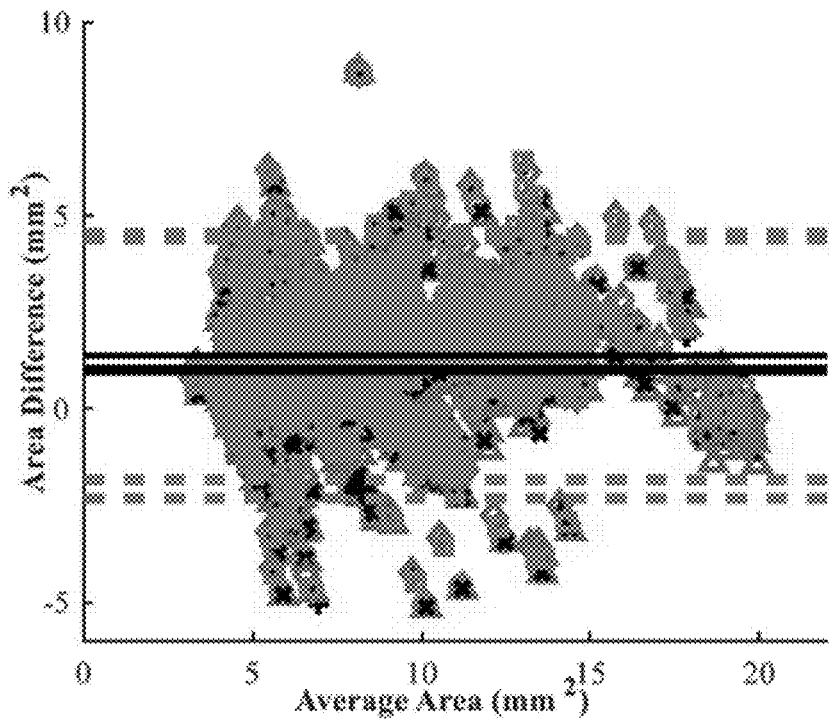

The average absolute (net) difference area between the algorithm results and human annotations in each frame was annotations which systematically underestimated the vessel area (Table III and FIGS. 12A and 12B).

TABLE III

PERFORMANCE METRICS COMPARING REGONS DELINEATED BY OUTER BORDER AS DETECTED BY VARIOUS INTERPOLATION & SURFACE FITTING TECHNIQUES

| Metric | Anisotropic Linear-Elastic Mesh | INTERPOLATION METHODS | | | SURFACE FITTING METHODS | | |
|---|---|---|---|---|---|---|---|
| | | Linear Interpolation | Nearest Neighbor Interpolation | Cubic Spine Interpolation | Polynomial Surface Model ($5^b$ Degree) | Local Linear Regression | Local Quadratic Regression |
| Sensitivity | 90.79 | 81.89 | 82.35 | 81.94 | 80.74 | 81.11 | 80.96 |
| Specificity | 99.00 | 99.19 | 99.10 | 99.18 | 99.42 | 99.47 | 99.46 |
| Jaccard Index | 83.67 | 76.61 | 76.48 | 76.56 | 76.90 | 77.62 | 77.39 |
| Dice Index | 91.11 | 86.75 | 86.67 | 86.73 | 86.94 | 87.40 | 87.25 |
| $R_{over}$ | 0.9079 | 0.8189 | 0.6235 | 0.8194 | 0.8074 | 0.8111 | 0.8096 |
| $R_{nonover}$ | 0.1773 | 0.2501 | 0.2533 | 0.2508 | 0.2426 | 0.2339 | 0.2366 |

Figure 11A:
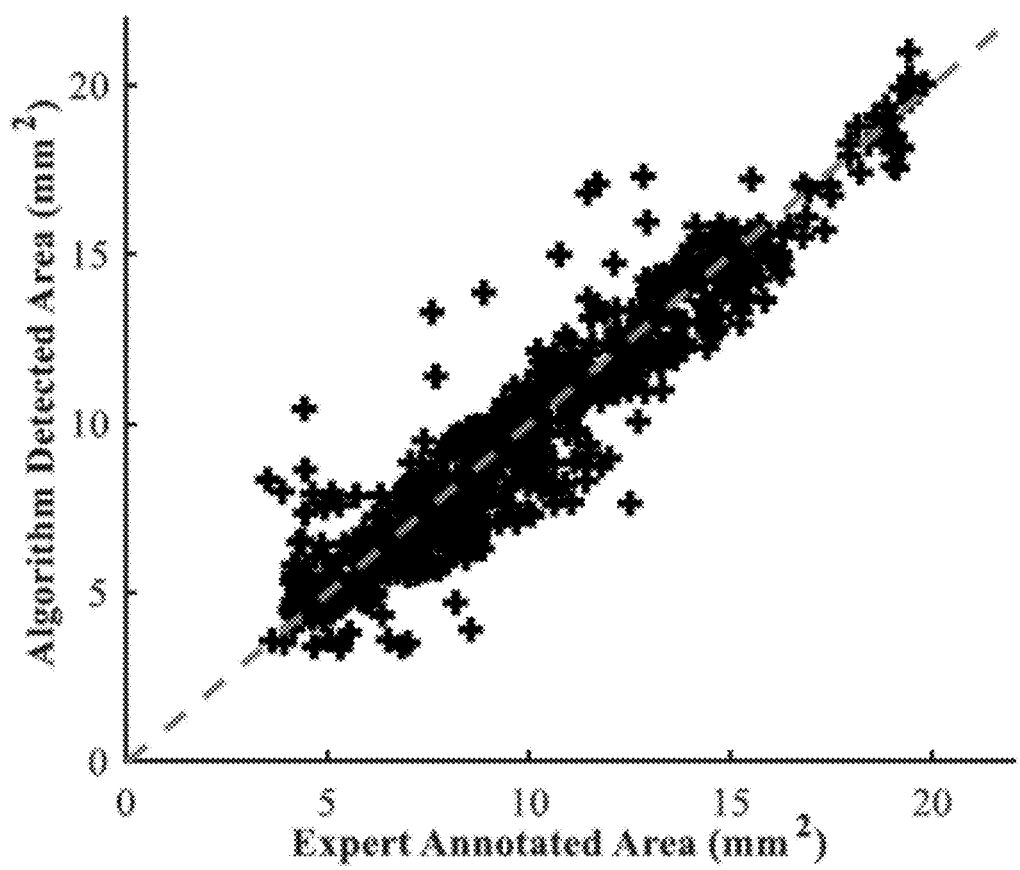
FIGS. 11A and 11B show a comparison of algorithm results and human expert annotations of the outer border.
Figure 11B:
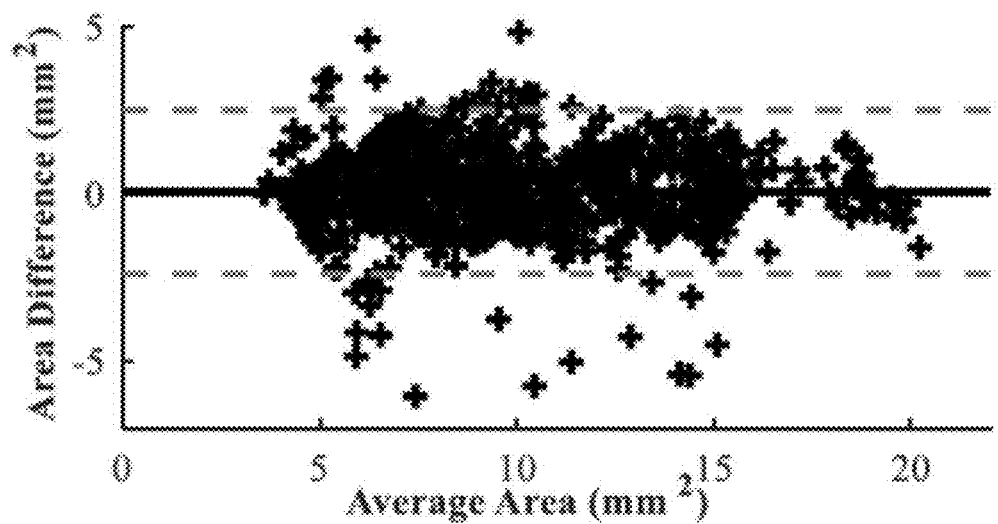

$^b z = p00 + p10 \times x + p01 \times y + \ldots + p14 \times xy^4 + p05 \times y^8$ 0.93 mm$^2$ (10.9%; overall mean of 0.07 mm$^2$) with a SD of 0.84 mm$^2$ (11.0%; 1.25 mm$^2$ for overall difference); the algorithm provided a very slight overestimation of the cross sectional area. FIGS. 11A and 11B show the error (FIG. 11A) and Bland-Altman (FIG. 11B) plots comparing the areas determined by the algorithm to those delineated by the average expert annotations. Direct comparison of overlapping regions enclosed by the annotated outer border is quantified in Table III.

A comparison between results obtained for the outer border with alternative interpolation and surface fitting methods is also included in Table III. As expected, performance of the existing interpolation and surface fit methods was mediocre and substantially underestimated vessel area (FIGS. 12A and 12B).

Algorithm Performance: Direct Comparison and Smoothness

The mean difference between the radial depths of the algorithm results and expert annotations of the outer border was 0.33±0.43 mm. The distribution of differences is centered around 0.09 mm, and has a standard deviation of 0.53 mm (FIG. 13); it largely reflects the distribution of differences between the annotations of the two experts, shown in the same figure.

Figure 14:
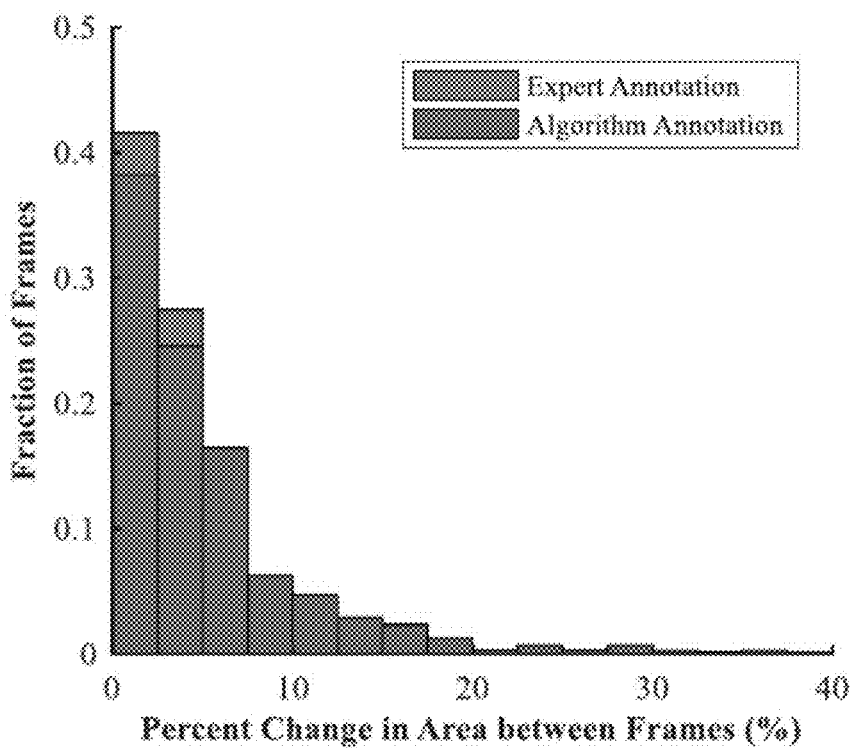
FIG. 14 shows a histogram showing frame-to-frame area change for both the expert annotations and algorithm delineations of the vessel outer border. The average area change from frame to frame for experts was 4.5%, while that for the algorithm was 5.5%.

The delineated outer border was relatively smooth and continuous in 3D. Frame-to-frame area change for both the expert annotations and algorithm delineations of the vessel outer border was negatively correlated with frequency of occurrence (FIG. 14). The average area change from frame to frame for experts was 4.5%, while that for the algorithm was 5.5%; physiological area change over the corresponding distance should theoretically be around 1-2% or less. The median percent change in frame-to-frame vessel area of the outer border annotations was also within 1% (percentage point) of that of the human experts (3.5% vs. 3.0%).

Alternative Interpolation and Surface Fitting Method Performance

Figure 15A:
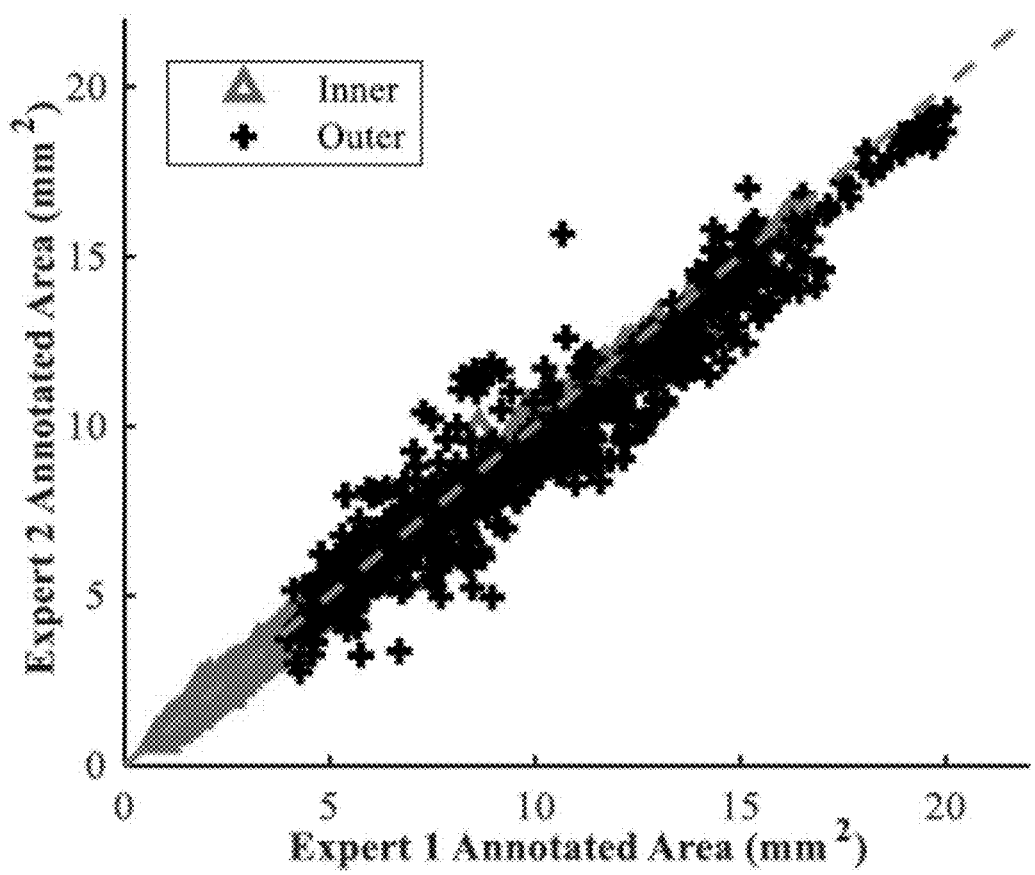
FIGS. 15A and 15B show a comparison of two expert annotations of the inner and outer borders.
Figure 15B:
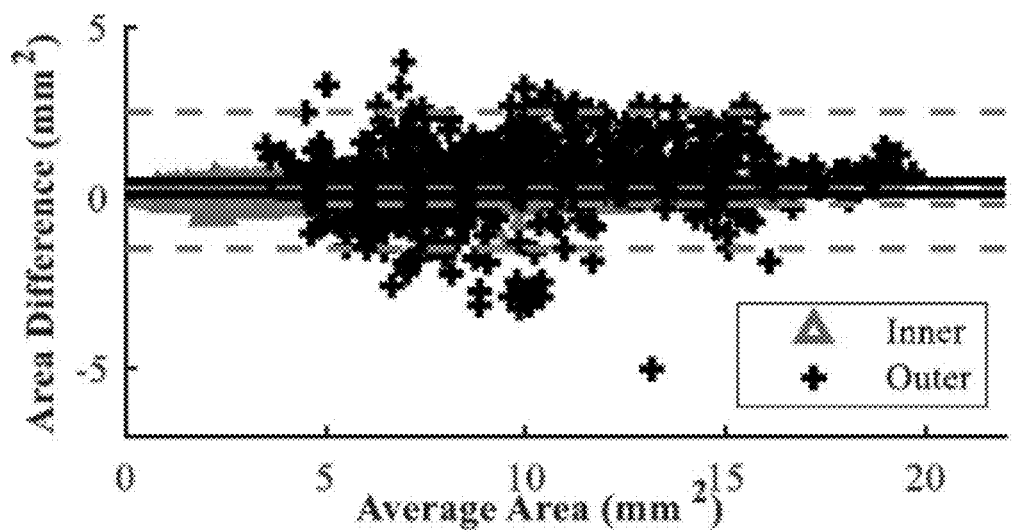

To demonstrate the value and impressive performance of the new method presented here, various alternative interpolation and surface fitting techniques were employed on the same set of detected outer border segments (and with the same automatically-delineated lumen contours). The existing interpolation and surface fit methods performed inferior to the presented method, and—as expected—produced Inter-Observer Variability In affirmation of multiple previous studies showing excellent inter-observer variability in OCT, variability between expert annotations in this study was low. Error (FIG. 15A) and Bland-Altman (FIG. 15B) plots compare the two experts to each other. The average absolute difference between the areas of their annotations was just 0.13±0.11 mm$^2$ (2.5±2.3%) and 0.88±0.75 mm$^2$ (9.7±8.6%) for the inner and outer border tracings, respectively; coefficients of determination between the two were greater than 0.99 and 0.93, respectively. Additionally, the average absolute radial distance between their inner and outer border annotations was just 0.07±0.07 mm and 0.21±0.23 mm, respectively. The distribution of radial distance between inner border tracings is centered around 0.02 mm with a standard deviation of 0.09 mm, while the distance between outer border tracings is nearly perfectly centered at 0.10 mm, and the standard deviation is 0.30 mm (FIG. 13), further confirming the observation of strong agreement.

OCT-IVUS Comparison

Figure 16A:
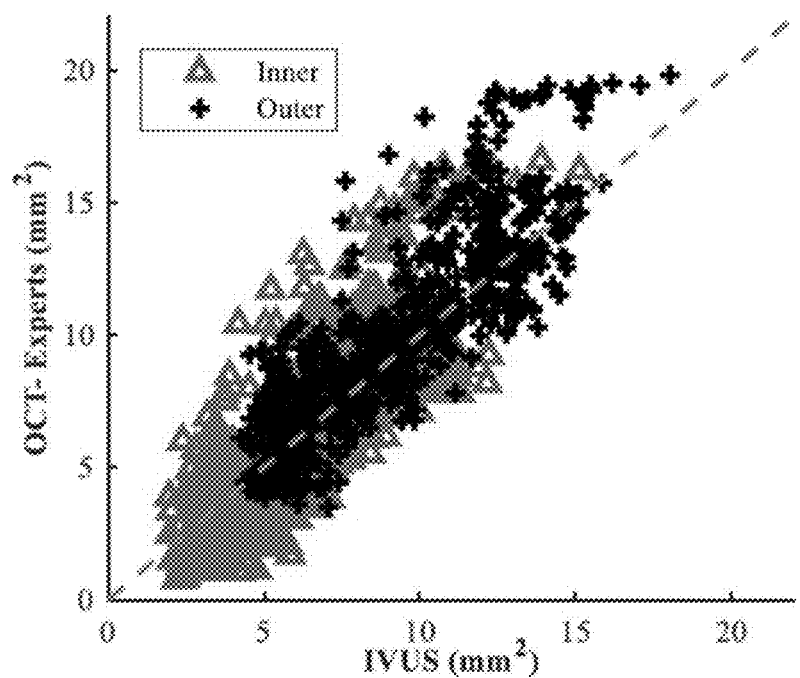
FIGS. 16A-16D show a comparison of the inner and outer borders delineated in OCT and intravascular ultrasound (IVUS).
Figure 16B:
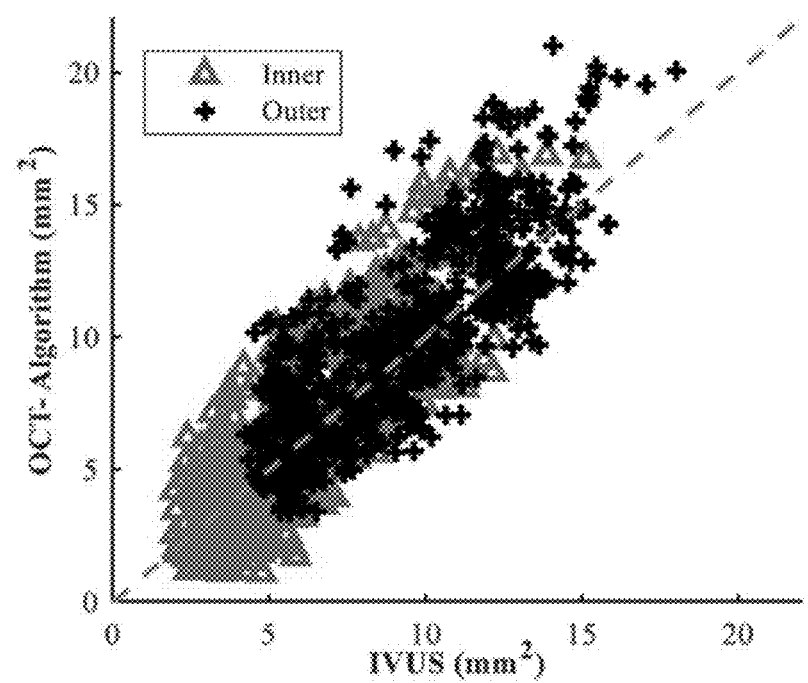
Figure 16C:
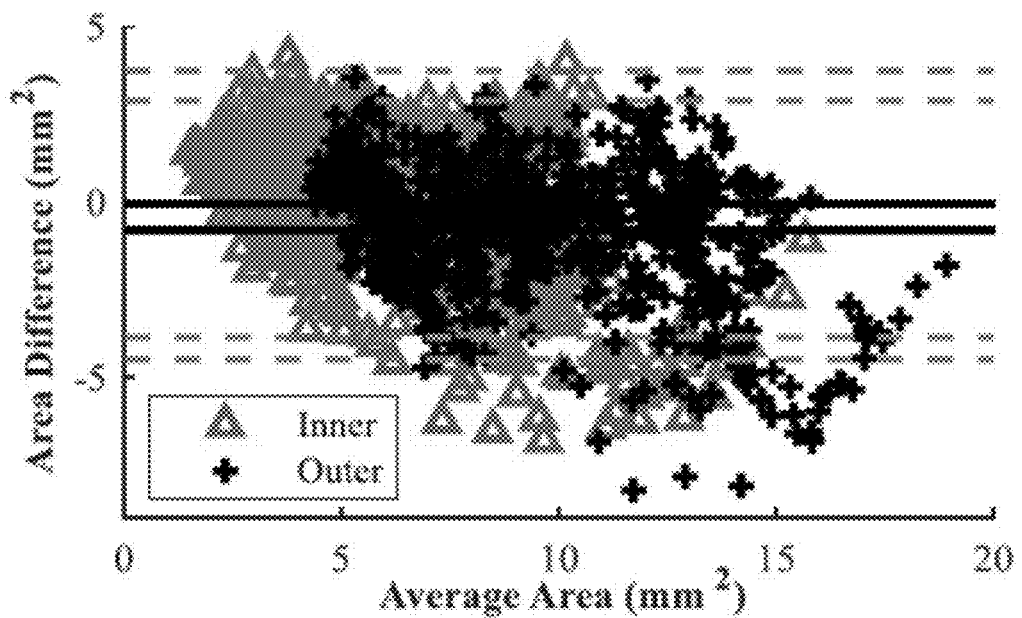
Figure 16D:
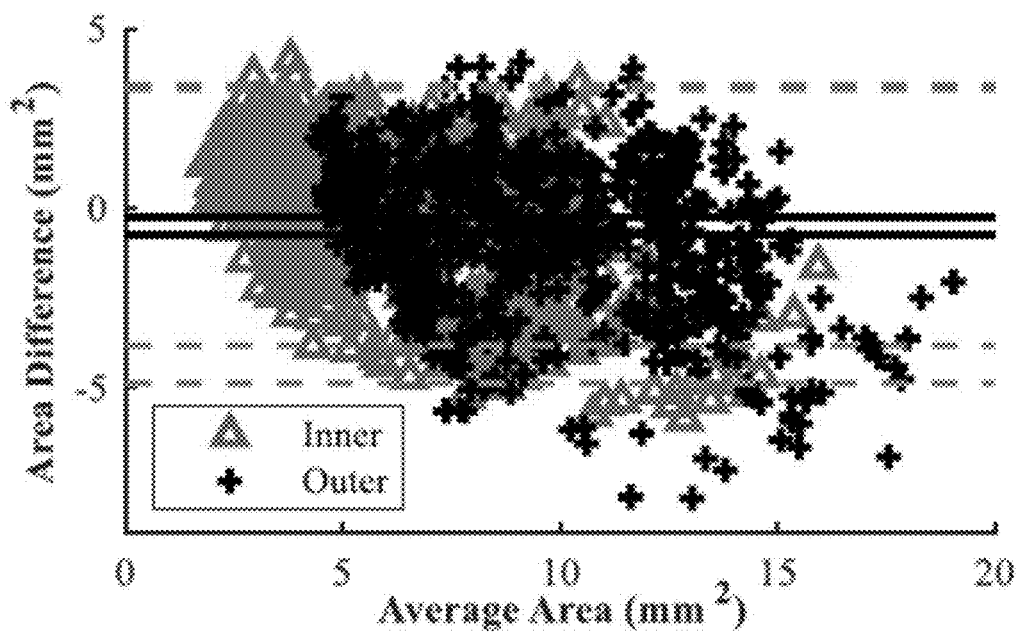

Agreement between cross-sectional areas delineated in corresponding OCT and IVUS frames show strong but imperfect agreement, as expected. Error (FIGS. 16A, 16B) and Bland-Altman (FIGS. 16C, 16D) plots compare areas delineated by an expert in IVUS to those delineated by both experts and the described algorithm in OCT. The average absolute difference between the areas of expert annotations for the inner and outer border tracings was 1.48±1.26 mm$^2$ (26.9±21.3%) and 1.49±1.39 mm$^2$ (16.4±13.4%), respectively. Comparing the algorithm results in OCT to the expert annotations in IVUS, the average absolute difference between the inner and outer border tracing areas was 1.41±1.17 mm$^2$ (25.0±20.1%) and 1.72±1.43 mm$^2$ (19.2±15.0%), respectively.

Accordingly, a surface fitting approach inspired by Newtonian physics was highly effective in fitting variably-sparse and questionably-reliable data. Intuitively applying an anisotropic linear elastic mesh with a force function helped autonomously delineate the outer border of a diseased vessel in OCT images. This capability has exciting implications, as it allows for the construction of 3D models of patient-specific vessel geometry from high-resolution OCT data for research and future clinical applications. Such models have been used to quantify and/or visualize 3D vessel properties, simulate interventions and their consequences through finite element and computational fluid dynamics analyses, and identify some cases of vulnerable plaques. However, previous coronary artery anatomic reconstructions have been subject to limitations in application and/or fidelity arising from methodological approaches. Many modeling approaches have utilized either idealized geometries or relatively low-resolution image sources, such as IVUS, angiography, magnetic resonance imaging, or computed tomography, resulting in necessarily simplified models. Others have relied on histology of excised tissue, which precludes predictive studies, serial monitoring, or application to current patients. Modeling approaches to date utilizing high-resolution OCT have been limited by assumptions made during the reconstruction of the arterial wall; some use only the inner (lumen) border obtained from OCT (e.g. for computational fluid dynamics without fluid-structure coupling), others have extrapolated radially from the inner border by a fixed distance to approximate the outer border, while some have lofted circumferential cross-sections of indirectly-calculated diameters, defined only in plaque-free regions, to create external arterial wall surfaces. The spring contour detection approach described allows for the construction of models from in vivo geometry, without the limitations of idealization or unrealistic geometric assumptions, and with the benefit of the high resolution of OCT. This method can also be used in conjunction with existing reconstruction techniques that presuppose knowledge of the outer border location.

The method presented here is flexible, and may be applied to various other applications within and beyond image processing. In situations where gaps exist in the interior of data, where no or limited information is available, data points are noisy, or data are unevenly-distributed, the surface fitting technique can be used where others may struggle, providing estimates for the missing information and smoothed assessments of the known data. Moreover, as shown in the smoothing of the lumen, which was nominally detected using the procedure of Athanasiou et al. (see above), the presently-disclosed procedure can also be used to smooth complete sets of noisy, yet reliable, data. Furthermore, while optimization using curated datasets improves fit performance, parameters may be selected intuitively or heuristically to achieve reasonable fits. This feature sets the approach apart from others, such as polynomial fits, which provide drastically-varying results with slight modifications of input parameters. Finally, the intriguing ability to specify a force function provides a unique opportunity to incorporate complex features of all available data to improve the fit and resulting evaluation of underlying information. This is particularly useful in image analysis, where features may not be readily detected but hints about the likely position of such features may be extracted from the rich set of information embedded within the image. Thereby, insights from other studies, including machine learning, pattern recognition, and other analyses, may be incorporated.

Opportunities exist to enhance and improve the performance of the fitting technique in this application. Accuracy of the current approach is primarily limited by two factors: inner and candidate outer border segment detection. Error in lumen border detection generally arises in the presence of image acquisition artifact, such as insufficient blood flush or irregular catheter rotation, as well as side-branches. Lumen detection is important to the outer border detection process, as it is used to flatten the image prior to detection of the contours that are likely segments of the outer border—errors in lumen detection thus skew or distort the flattened image. However, because the outer surface fitting is performed in the flattened state (to avoid arbitrary penalization of contours arising due to catheter position within the lumen), any error in detecting the lumen is directly introduced to the outer border when the fit surface is reconstituted to the non-flattened state. Therefore, improved techniques to detect the lumen, particularly those robust to artifact presence, will have a direct positive impact on the performance of this technique.

Detection of visible segments of the outer border is also a process step primed for improvement. While segments were identified by the presented approach in just over half of all radial projections, some segments visible to the trained eye were not identified. Of greater concern are the candidate segments identified that did not correspond to the actual outer border. These segments usually arose at the adventitia-periadventitia transition or, more problematically, within heterogeneous plaques where the selected grayscale pattern occurred by happenstance (e.g. when thin bands of calcified tissue were present). In this latter case of false segment detection, the existence of the falsely-identified outer border segments skewed the surface in a way that led to underestimation and misrepresentation of some regions with high plaque burden. However, the fitting approach tempered these negative effects, especially when the false detected segments were small relative to the correctly-identified segments (as they frequently were). Nevertheless, improved approaches will be useful. One possible alternative detection method of note has been recently reported for segmentation of healthy wall regions, and other methods similarly derived from earlier segmentation techniques developed for retinal OCT imaging are sure to follow. Additional strategies for segment detection improvement could include explicit incorporation of penetration depth, the external limit of which is not currently considered by the algorithm. Inclusion of this factor could be used to delimit a region of interest within a proximal subset of the image, thereby eliminating opportunities for false detection beyond this region and reducing computational operations in regions of the image in which no viable information is likely to be present.

Finally, an additional opportunity for improving performance is implementation of a more sophisticated force function ($F_{ij}$) and/or base layer ($L_{ij}$). Such functions could leverage additional a priori knowledge and insights gained through previous studies of typical plaque and vessel wall morphology (akin to the approach of developing a plaque-specific generalized estimation equation model of necrotic core thickness), perhaps incorporating plaque tissue characterization studies.

Figure 17:
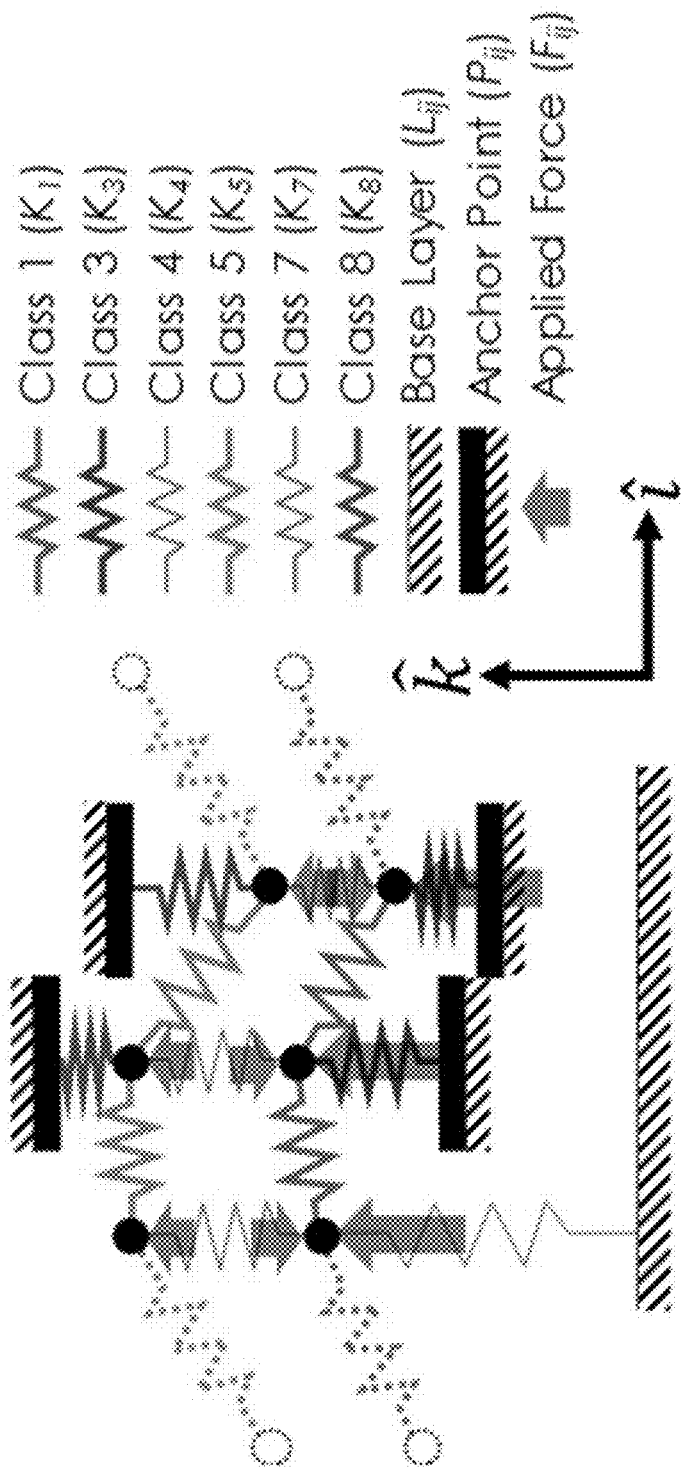
FIG. 17 shows a schematic of an exemplary embodiment of coupled anisotropic linear-elastic meshes for fitting multiple layered surfaces. Note that classes of springs not shown (2 and 6) are out of plane (oriented in the j-direction) in this view.

There are certain limits to the applicability of the technique, as well as the results of this study. As described here, this surface fitting technique does not allow for folds in the surface, which would be represented as non-singularities in the contour map with multiple nodes in a single column. Similarly, the surface must intersect each column, such that intentional gaps cannot be achieved. Modification of the presented approach using the same underlying physical concepts could allow for application in either scenario. Indeed, this approach has been extended to fit multiple layered surfaces simultaneously by placing multiple nodes in each column and coupling surfaces with springs connecting nodes of the same column (FIG. 17). Another limitation pertains to parameter selection and generalizability. While the dataset included 7 distinct image datasets (pullbacks), convergence testing using information from increasing numbers of randomly-selected image frames (FIGS. 7A, 7B)

showed that optimal parameters—and subsequent overall performance—did vary significantly depending on the number and subset of frames used. Yet the strong convergent trend, which is generally stabilized when at least 30 (of the 724) frames were used, suggests that the final parameters should be close to optimal for all OCT datasets for this application. Parameters for other applications may differ and may require training datasets of their own to determine. Furthermore, optimization for other criteria may be preferable for this and other applications. For example, rather than minimizing summed radial distance between the surface and the expert annotation of the training set, it could be argued that smoothness or an overlap comparison metric (e.g. sensitivity, specificity, $R_{over}$, $R_{nonover}$, etc.) are more important and relevant metrics. Such changes would result in different minimization functions and subsequently different fit parameters ($K_2/K_1$, $K_3/K_1$, $K_4/K_1$, and $\alpha/K_1$).

Finally, regarding the validation of this method, expert annotations were used as the primary reference, but are not considered the clinical gold standard for identifying the outer border of the vessel. Due to the limited penetration depth of OCT, IVUS is considered the clinical gold standard for measurements involving the outer border, as the border is almost universally visible, regardless of plaque burden. In contrast, and as noted earlier, the outer border is often not visible in OCT within regions with substantial lipid plaque. However, evidence in literature indicates that outer border estimations by expert interventional cardiologists are generally quite accurate compared to annotations made with clinical gold standard IVUS. Because only annotations made within the same OCT images could be used in directly validating the automatic detection (i.e. through annotation distance and overlap metrics), these were considered the primary validation reference for this purpose. Nevertheless, annotated cross-sectional areas in co-registered IVUS images were included for comparison to incorporate the clinical gold standard in validation and to test for viability in clinical scenarios. As expected, agreement between the algorithm results and IVUS expert annotations was not as good as agreement with OCT expert annotations, though this largely reflected the difference between IVUS and OCT expert annotations (FIGS. 16A-16D). Differences between measurements made in the two modalities have been reported elsewhere, even in well-controlled phantom models, and compounding errors arising from physiological state disparities between non-concurrent acquisitions and imperfect co-registration amplify these differences. To avoid these magnifying errors, other work in the field has leveraged phantom models of known, directly measureable dimensions for validation purposes. While exceedingly useful for validating imaging technology and evaluating measurements of inner surfaces and their contents (e.g. stents), measurement of the outer border does not offer a useful validation mechanism due to the lack of physiologically-relevant optic properties and feature patterns.

Thus, the smooth surface fitting method disclosed herein which implements an anisotropic linear-elastic mesh and force function overcomes challenges and shortcomings of existing interpolation and surface fitting techniques. Use of equilibrated mechanical lumped elements helps reconstruct and smooth surfaces in the face of partial, imperfect, or incomplete information. With this efficient, flexible, and intuitive approach, the capability to autonomously delineate the entire outer border of diseased vessels in OCT images has been successfully demonstrated. The method is even more intriguing given that extension of this work could assign values and attributes to physical parameters that are extracted from the architecture and morphology of a blood vessel wall. In addition, fit parameters derived from the data might well offer deeper meaning and allow inferences about vessel state and function.

Convolutional Neural Network

In various embodiments, the above-described wall area (WAR) delineation procedures may be used in conjunction with a trained classification model based on deep learning or other artificial intelligence methods (e.g., a neural network, a CNN, a support vector machine, a random forest, etc.) to identify and classify the composition of the material within the identified arterial walls based on data obtained from an interferometric method such as OCT. OCT produces high-resolution tomographic images of artery lumen and vessel wall morphology. Manual analysis of the diseased arterial wall is time consuming and may be sensitive to inter-observer variability; therefore, machine-learning methods have been developed to automatically detect and classify mural composition of atherosclerotic vessels. However, none of the tissue classification methods include in their analysis the outer border of the OCT vessel; instead, previous methods have considered the whole arterial wall to be pathological, and these methods do not consider the OCT imaging limitations, e.g. shadowed areas, in their analysis.

Accordingly, disclosed herein are embodiments of a deep learning method that subdivides the whole arterial wall into one or more of six different classes: calcium, lipid tissue, fibrous tissue, mixed tissue, non-pathological tissue or media, and no visible tissue. In various embodiments, the method steps may include (1) defining wall area (WAR) using lumen and outer border detection methods such as those disclosed herein, followed by (2) automatic characterization of the WAR using deep learning methods such as a convolutional neural network (CNN) algorithm. In one particular embodiment to validate this approach, 700 images of diseased coronary arteries from 28 patients were manually annotated by two medical experts, while the non-pathological wall and media was automatically detected based on the Euclidian distance of the lumen to the outer border of the WAR. Using embodiments of the disclosed method, an overall classification accuracy of 98.9% has been attained, indicating its usefulness in clinical settings.

The limitations of OCT technology have led to various implementations of automated analysis methodologies. However, these other methodologies have detected only the inner lumen border of the vessel or have detected the inner lumen border along with an estimate of the plaque area of the vessel. Since manual plaque characterization is time consuming and requires well-trained readers, several studies have attempted to automatically detect the various plaque components using OCT images, in one instance attempting to correlate the backscattering and attenuation coefficients with C, LT, and FT, and in another instance attempting to correlate the attenuation coefficients with healthy vessel wall, intimal thickening, lipid pool, and macrophage infiltration. Nevertheless, these other studies failed to define any clear threshold values between the different tissue types. Going one step further and using machine learning, another study presented a fully-automated OCT plaque characterization method which classified plaque as C, LT, FT, or MT, with 83% accuracy. More recently, deep learning approaches using convolutional neural networks (CNNs) have been conducted, achieving an overall accuracy of up to 91.7%.

Although prior implementations of CNN-based methods have outperformed machine learning methods, they failed to characterize the whole arterial wall, resulting in methods which cannot compete with widely-used virtual histology IVUS (VH-IVUS), limiting the imaging detail superiority benefits of OCT when compared to IVUS. The primary drawbacks hampering automated OCT plaque characterization include the lack of large amounts of annotated images and the non-realistic tissue (area of interest) segmentation caused by the difficulty of automatically detecting the outer border. The approach disclosed herein combines one or both of lumen and outer border detection algorithms with an automated tissue identification method to characterize the whole arterial wall to produce results that are comparable to those obtained using VH-IVUS.

In various embodiments, the tissue characterization method may include one or more of the following innovative aspects:

1. use of CNNs trained with a large amount of annotated data to detect atherosclerosis;
2. detection of normal tissue and shadowed areas within the OCT images; and
3. detection and classification of the whole arterial wall using OCT images in a similar way as VH-IVUS performs its analysis, enabling the wide use of OCT in atherosclerotic tissue detection.

Figure 18:
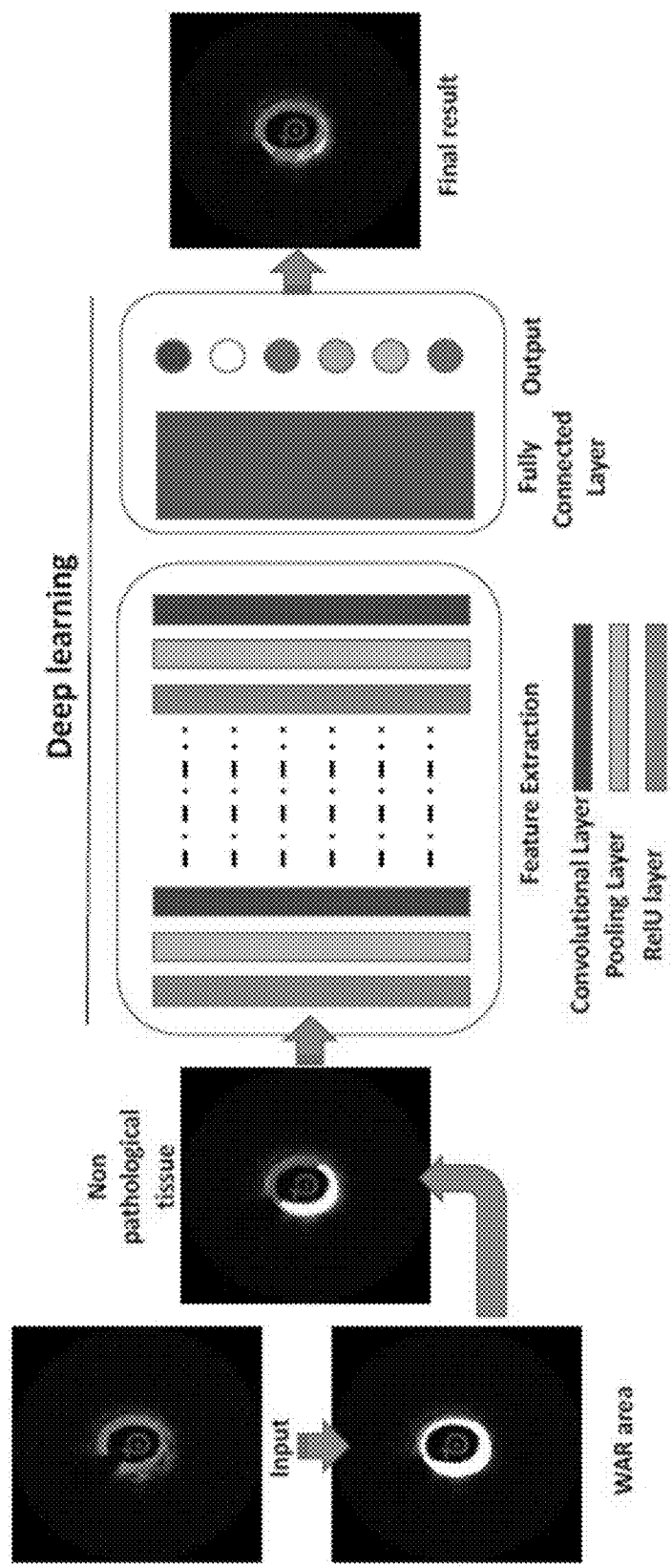
FIG. 18 shows a schematic presentation of an exemplary version of the proposed methodology.

In certain embodiments, the disclosed tissue classification method (FIG. 18) may include one or more of the following:

1. wall area (WAR) detection using lumen and outer border detection methods (e.g. as disclosed herein);
2. definition of the non-pathologic intima-media area; and
3. automatic characterization of the pathologic WAR using a CNN algorithm.

As disclosed above, WAR is defined as the area between the lumen and outer border (FIG. 19), i.e. the media-adventitia transition. The lumen detection method uses as input 2D cross-sectional OCT images, produces longitudinal cross-sectional images (sagittal cuts) which more accurately represent the sequential area of the OCT pullback, detects the lumen by applying bilateral filtering and a K-means algorithm, and translates the detected lumen to the 2D OCT images, although other procedures may be used to identify the lumen. The outer border detection method detects the outer vessel border within segments of the OCT pullback that are visible and then, by using a unique 3D surface-fitting method, such as that disclosed herein, fills the non-visible parts.

Non-Pathologic Intima-Media Area Detection

Once the lumen and media-adventitia borders have been detected, the non-pathological tissue and media layer (M) of the WAR are defined. The concept is based on the VH-IVUS histology method in which the normal vessel wall has intimal thickening of <300 µm. To measure the distance of the two borders, for each pixel of the WAR, p∈WAR, the combined distance of the pixel from the lumen and media-adventitia borders was calculated:

$$D_{L-MA} = D_1 + D_2, \quad (25)$$

and the distance of the pixel from the media-adventitia border: D1.

Figure 19:
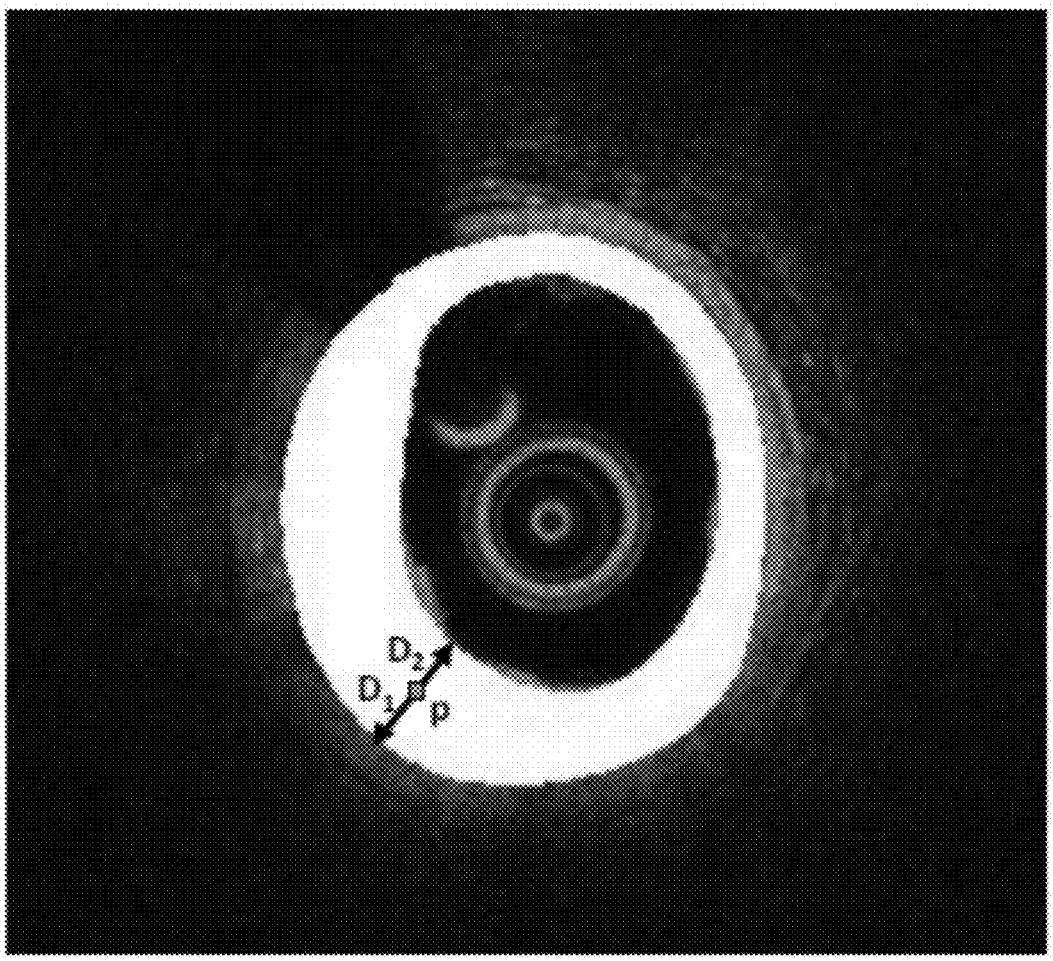
FIG. 19 shows a schematic presentation of the two Euclidean distances calculated for defining the non-pathologic intima-media area (M) within the WAR (white).

Here, $D_1$ is the Euclidean distance of the pixel p from the media-adventitia border and $D_2$ is the Euclidean distance of the pixel p from the lumen border; if $D_1$<100 µm (i.e. the pixel is close to the outer edge of the vessel) or $D_{L-MA}$<300 µm (i.e. the pixel is in a relatively thin portion of the vessel) the pixel belongs to M. A schematic presentation of the two distances is shown in FIG. 19. As shown in the panel labeled "Non pathological tissue" in FIG. 18, the pixels in the relatively thin portion of the vessel (in the upper right hand portion of the cross section) as well as those at the outer perimeter of the vessel are flagged as being non-pathological, whereas the pixels in the relatively thicker portion in the lower left of the cross-section away from the edge are white (unclassified) and are subject to further analysis and classification by the deep learning procedure. In various embodiments, the particular values used for these determinations, e.g. $D_1$<100 µm and $D_{L-MA}$<300 µm, may be adjusted based on knowledge of a particular tissue type, for example knowledge regarding the thicknesses of normal and diseased vessel wall tissue.

CNN-Based Classification

After detecting the pixels that belong to the non-pathological tissue and media (M) area, the remaining WAR pixels are automatically classified into one of five categories including four plaque types: calcium (C), lipid tissue (LT), fibrous tissue (FT), or mixed tissue (MT), and no visible tissue (catheter artifact; N), using a CNN network.

CNN Algorithm

CNNs belong to the family of deep learning networks, and may be used to analyze and classify images. CNNs generally include an input layer and an output layer with multiple hidden layers between the input and output layers. The hidden layers may include several convolutional layers which automatically extract the complex features of the images.

A CNN may be represented by a non-linear function:

$$p_i = P(I; \theta) \quad (26)$$

which maps an image $I \in R^{H \times H}$ having H×H size, to a vector $p_i = (p_1, p_2, \ldots p_c)^T$, where $p_i \in [0,1]$ and denotes the probability of the image I to belong to one of c classes: i=1 ... c. $\theta = \{\theta_1, \theta_2, \ldots \theta_K\}$ are the number of K parameters used to map the input image I to the vector $p_i$.

The training of the CNN can be considered as a non-linear optimization problem:

$$\arg_\theta \min L_{\{I^{(1)}, I^{(2)}, \ldots, I^{(N)}\}}(\theta) \quad (27)$$

Here, N is the number of images used to train the CNN, and $$L_{\{I^{(1)}, I^{(2)}, \ldots, I^{(N)}\}}(\theta) = -\frac{1}{N} \sum_{j=1}^{N} w_j y C^{(i)T} \log P(I^{(i)}; \theta) \quad (28)$$

is the cross-entropy loss (log loss) measuring the classification performance (having values between 0 and 1) for the $C^{(i)T}$ labeled vector of the e classes and w weights:

$$w_i = \frac{\frac{1}{M_i}}{\sum_{i=1}^{c} \frac{1}{M_i}} \quad (29)$$

for the M training data.

To minimize the training time of the CNN, in certain embodiments the Stochastic Gradient Descent (SGD) iterative method may be used. SGD approximates the dataset with a batch of random samples, using the stochastic gradient computed from the batch to update the model with each iteration. SGD might oscillate along the path of steepest descent (gradient descent) towards the optimum, instead of along the path toward the optimal, since the gradient always points towards the opposite side of this optimum from the current position. A solution to that problem is adding a momentum term to the parameter update to reduce oscillation:

$$\theta_{\lambda+1} = \theta_\lambda - \Delta \nabla L(\theta_\lambda) + \gamma(\theta_l - \theta_{\lambda-1}) \quad (30)$$

where $\lambda$ is the iteration number, $\alpha>0$ is the learning rate, and the momentum term $\gamma$ determines the contribution of the previous gradient step to the current iteration.

The SGD algorithm uses a subset of the training set called a mini-batch, evaluates the gradient, and then updates the parameters. Each evaluation is an iteration, and at each iteration the loss function is minimized further. The full pass of the training process over the whole training set using mini-batches forms an epoch.

CNN Architecture

Figure 20:
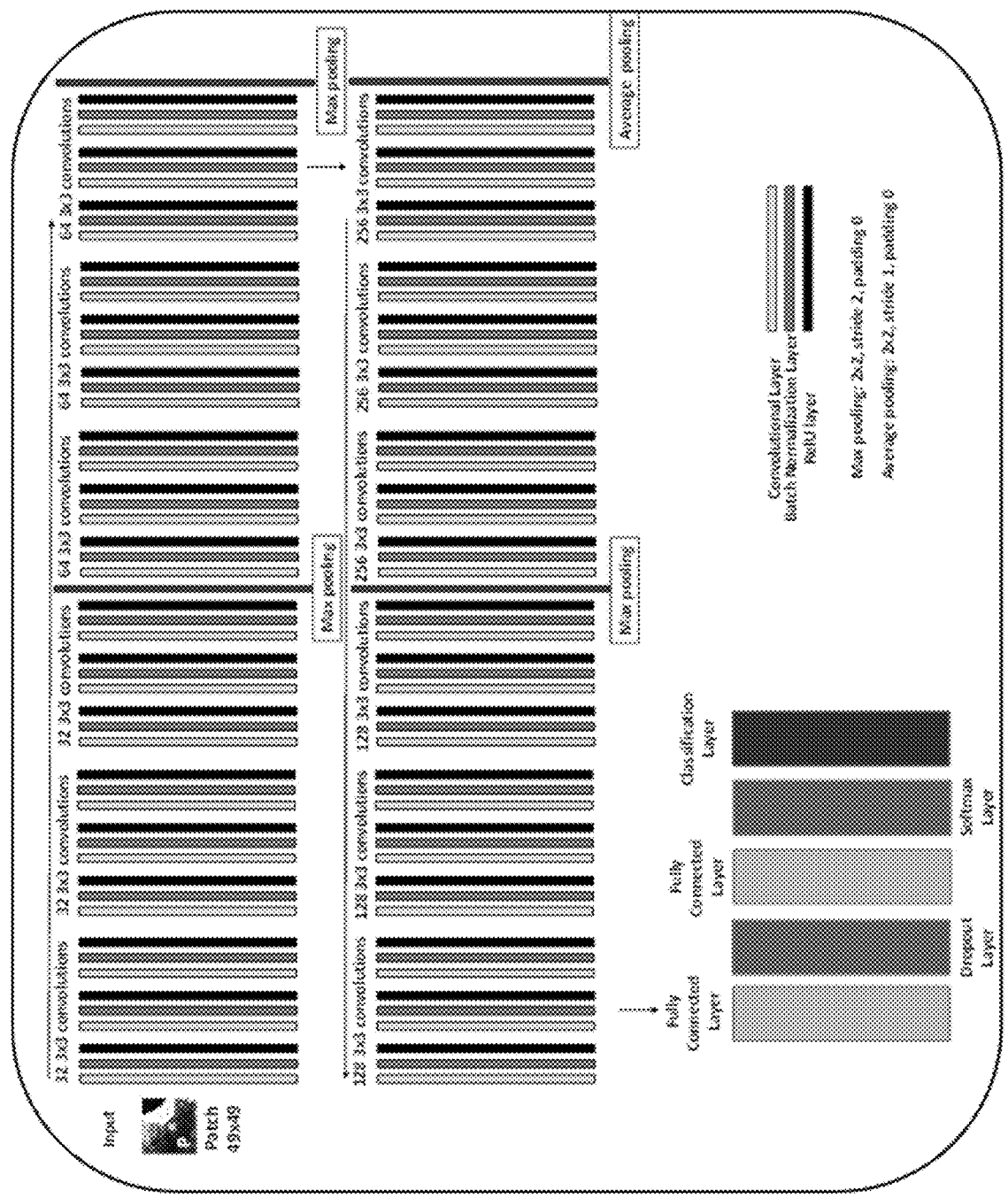
FIG. 20 shows an architecture of the CNN used to classify the WAR pixels.

To classify the pixels of the WAR, a sequence of convolutions was used. To achieve the best classification results, different patch sizes, numbers of input patch convolution sequences, filters, and filter sizes were tested. The best results were acquired when having 46 layers in the network (FIG. 20). Other variations that may be used include (instead of applying Max pooling every three convolution blocks): applying Max pooling after each convolution, applying average pooling instead of max, using fewer filters from the first convolution block, or using more convolution blocks. In addition, patch sizes in a range of 21×21 to 51×51 are possible, with a patch size of 49×49 being used for the present studies in part due to being suitable for use with the 500 line frame size of the data.

Dataset

Twenty-eight (28) patients who underwent OCT examinations gave their informed consent for the study, and the study was approved by the Ethics Committee of the institution. Medical experts used the optical frequency domain imaging FD-OCT C7XR system and the DragonFly catheter (St. Jude Medical, Lightlab Imaging Inc., Westford, Mass., USA), which offers a maximum frame rate of 100 frames per second, 500 lines per frame, a scan diameter of 10 mm, and axial resolution of 15 µm, to image 28 coronary vessels. All images were digitally stored in raw format for off-line analysis, and all imaging data sets were anonymized and transferred to the lab for further analysis.

Data from 22 of the patients was manually scored to generate a training data set to train the CNN and data from the remaining 6 patients was manually scored to use as a test data set for the trained CNN.

Wall Area Detection

Figure 21A:
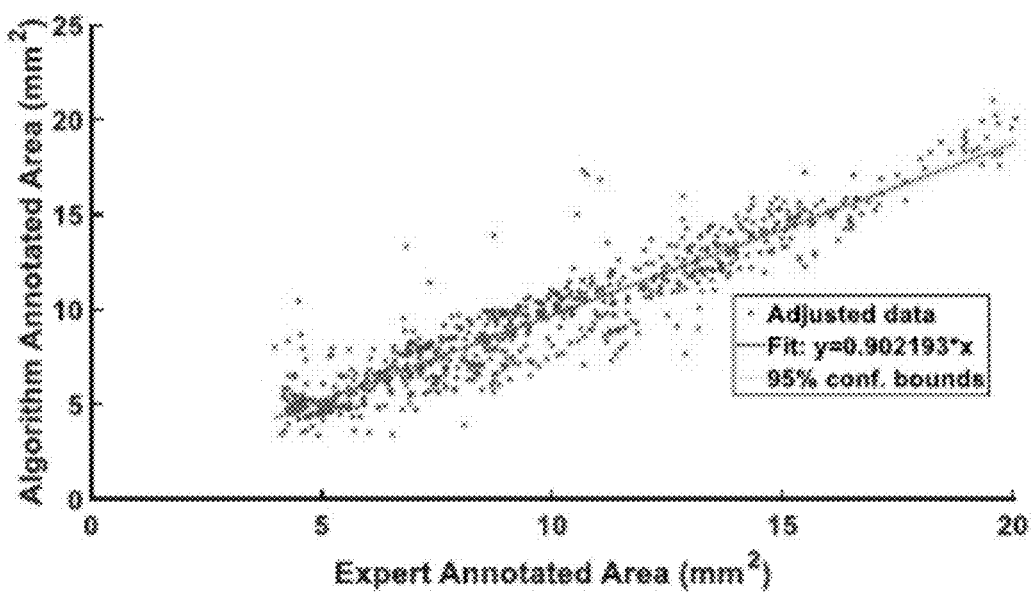
FIG. 21A shows a regression analysis plot between the WAR detected by the disclosed method and annotated by the experts.
Figure 21B:
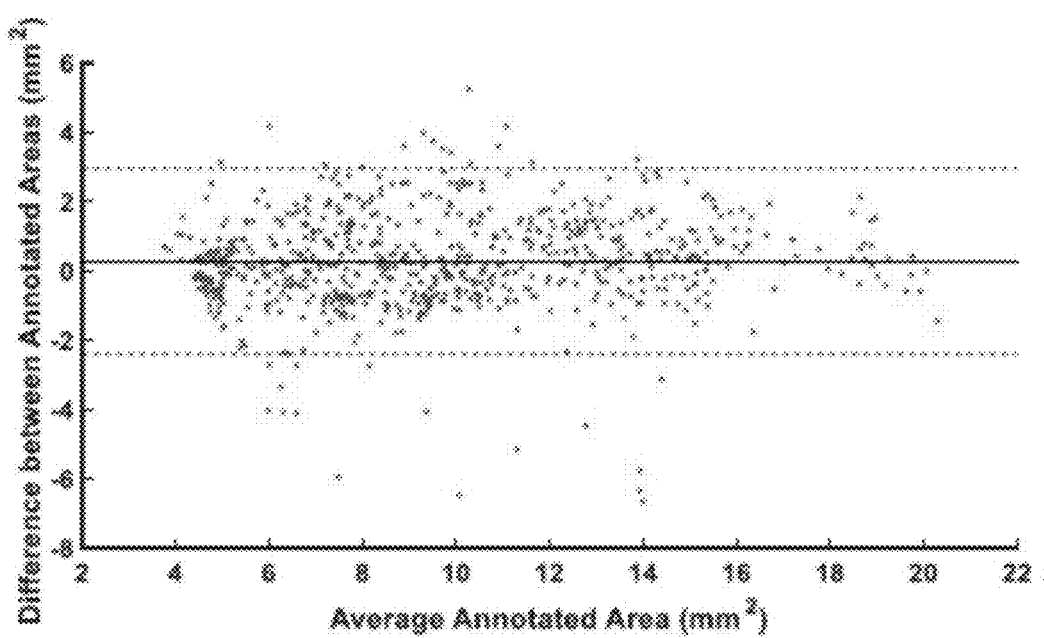
FIG. 21B shows a Bland-Altman analysis plot for the WAR detected by the disclosed method and annotated by the experts.

Two medical experts examined the OCT frames in 22 of the patients and selected 700 images which corresponded to diseased coronary segments. Afterwards, the experts independently marked the contours of the lumen border, the intima-media border, and regions of calcium (C), lipid tissue (LT), fibrous tissue (FT), mixed (C+LT) plaque (MT), and the area of the catheter shadow (no visible tissue; N); any disagreements in their annotations were resolved by consensus. The areas detected by the algorithm and annotated by the experts were calculated and compared (FIGS. 21A, 21B).

Plaque Characterization

Figure 22:
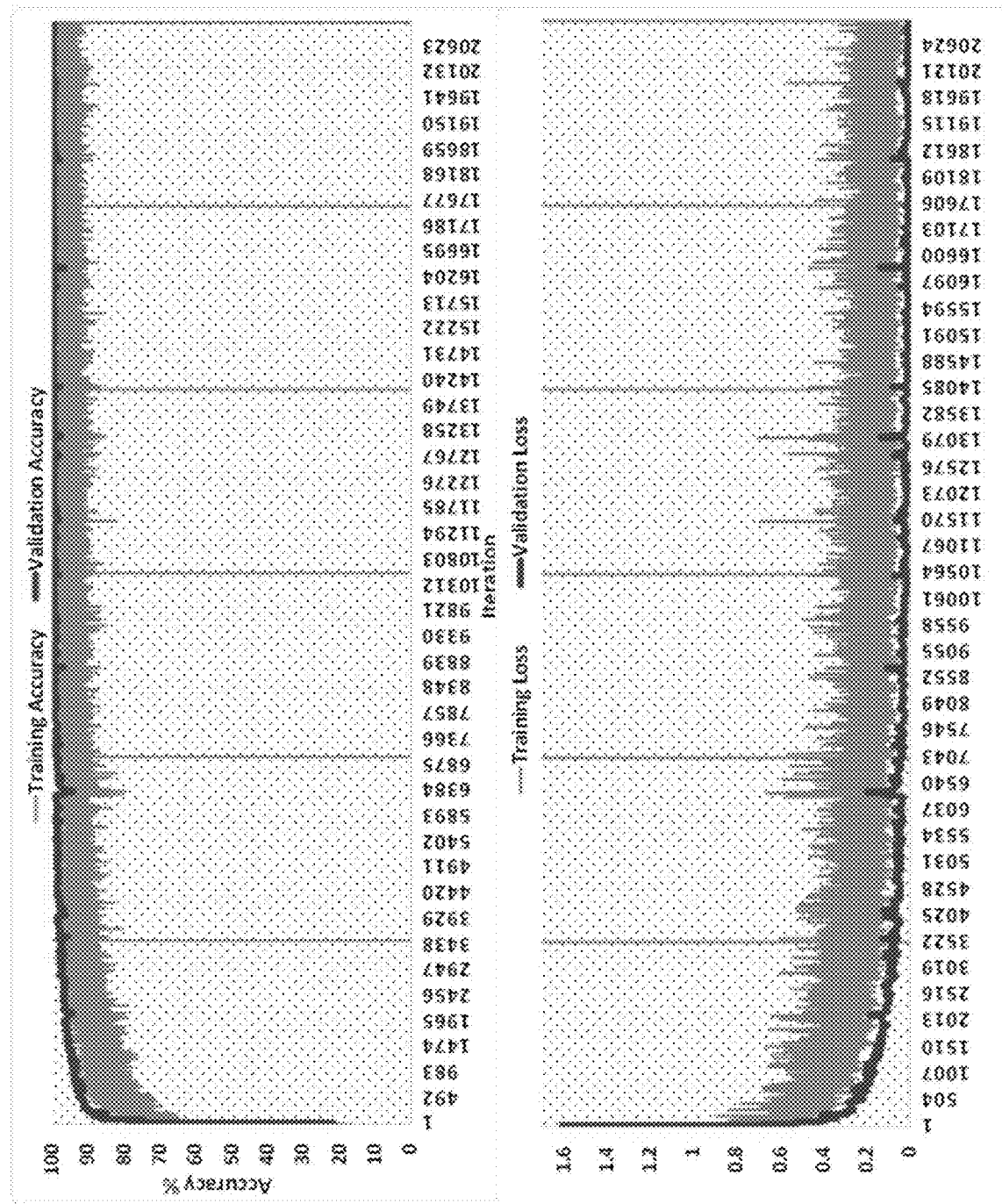
FIG. 22 shows training results of the CNN algorithm: Classification accuracies (top) and loss (bottom) for the training and testing data using the proposed CNN network over 6 epochs (3515 iterations each).
Figure 23:
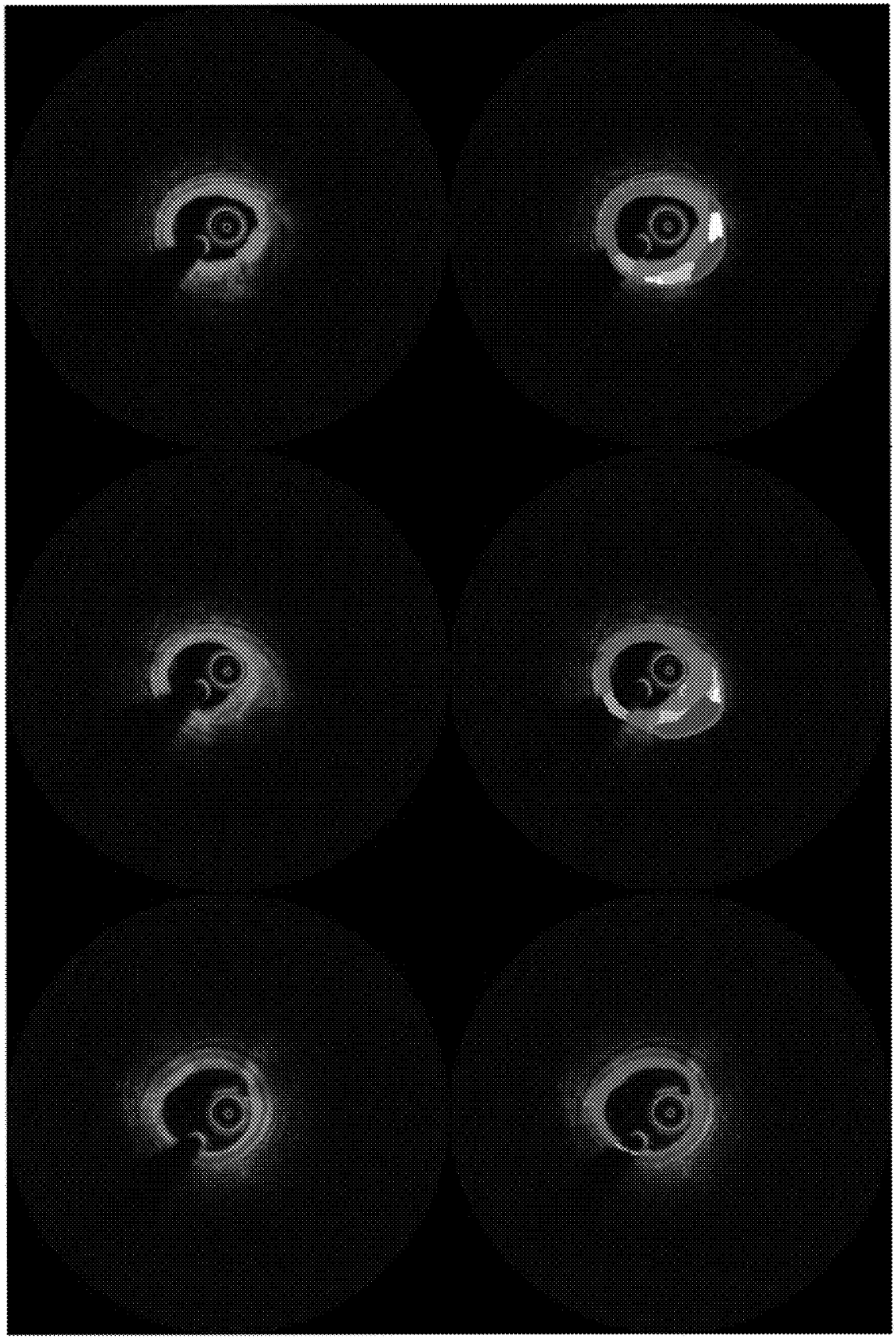
FIG. 23 shows application examples of the proposed integrated OCT plaque characterization method: initial images (top panels) and their corresponding color-coded images (bottom panels). Calcium (C): white, lipid tissue (LT): red, fibrous tissue (FT): green, mixed tissue (MT): light green, no visible tissue (catheter artifact; N): light gray and non-pathological tissue and media (M): dark gray.

The medical experts developed a training database by completely annotating at least 300 different plaque regions for 22 of the patients, from which 32 K patches were randomly selected for each class and augmented (each patch rotated 90° and 180°), resulting in 480 K patches (96 K for each of the five classes). The patches were used to train (450 K) and validate (30 K) the CNN parameters. The CNN algorithm reached a validation accuracy of 99.88% (FIG. 22). In some embodiments, 350 plaque regions were annotated from the 28 patients and were used to produce 1,149,330 individual patches (of which 669,330 were used for testing and the remainder for training), which is a substantially larger amount of data than has been used for any comparable study.

One expert developed a test database by annotating 50 areas in the remaining 6 patients as C (9450 patches), LT (174448 patches), FT (216336 patches), MT (35301 patches), or N (408243 patches) regions to test the classification accuracy of the proposed method. The CNN network was trained and validated using the MATLAB Deep Learning Toolbox and a NVIDIA Titan Xp GPU (PG611) with 12 GB RAM using the training database developed with the data from the first set of 22 patients, although in other embodiments other CNNs such as U-Net or a system based on a framework such as TensorFlow may be used. In certain embodiments, the overall accuracy of the proposed algorithm is 98.9% (Table IV); the ability of the method to produce an integrated plaque characterization map using OCT is presented in FIG. 21

TABLE IV

Confusion matrix of the tested patches.

| Confusion Matrix | C | LT | FT | MT | N | Accuracy |
|---|---|---|---|---|---|---|
| C | 8373 | 584 | 320 | 171 | 2 | 88.6% |
| LT | 416 | 171182 | 1744 | 1073 | 33 | 98.1% |
| FT | 113 | 370 | 215484 | 218 | 151 | 99.6% |
| MT | 67 | 705 | 2943 | 31534 | 52 | 89.33% |
| N | 5 | 61 | 207 | 10 | 407960 | 99.9% |
| Accuracy | 88.6% | 98.1% | 99.6% | 89.33% | 99.9% | 98.9% |

Figure 24:
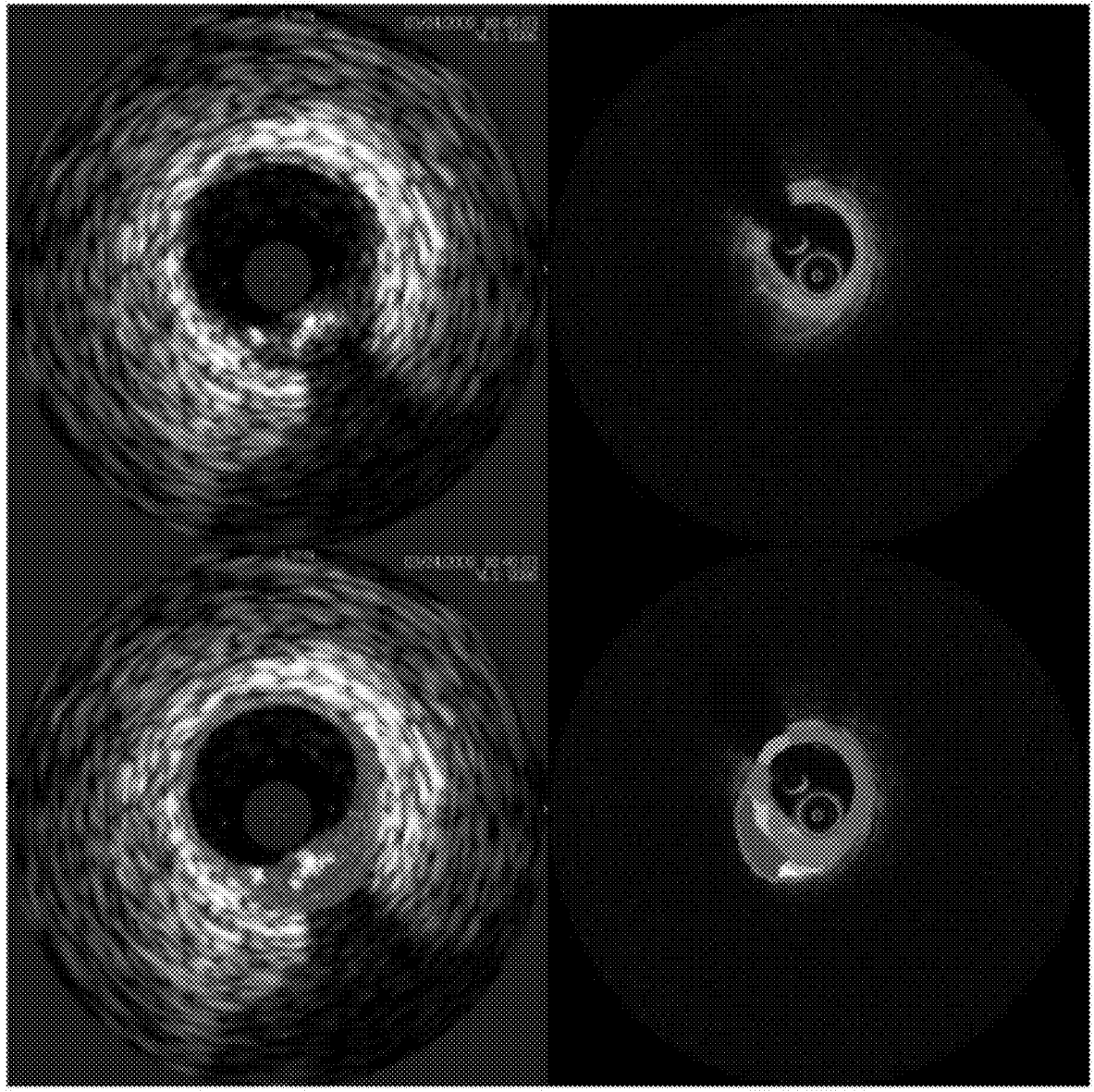
FIG. 24 shows an application example of data obtained and classified using a VH-IVUS system (left panels) and of data obtained using OCT and classified using the procedures disclosed herein (right panels).

Few methods have been presented during the last decade for detecting and characterizing atherosclerotic plaque using OCT images. These methods were primarily based on machine learning algorithms and more recently on deep learning approaches using convolutional neural networks (CNN). These methods can sufficiently detect a large percentage of the atherosclerotic tissue within the arterial wall. However, while CNN-based methods outperformed the machine learning methods, the methods produced by others could not characterize the whole arterial wall to produce results that are similar to those obtained using VH-IVUS (FIG. 24).

Accordingly, presented herein are embodiments of an automated method that automatically detects atherosclerosis and classifies the plaque image to 5 different classes: calcium (C), lipid tissue (LT), fibrous tissue (FT), mixed tissue (MT), no visible tissue (guidewire shadow artifact; N), and detects the non-pathological tissue or media (M). The method is based on the combination of WAR detection algorithms and CNN, and has been validated using the estimations of expert observers as a reference ("gold") standard in a large, clinically-relevant dataset. The experimental results demonstrate reliable tissue detection and characterization, even in images having artifacts.

The method is more accurate and realistic than the methods presented previously by others, which makes it notably qualified for use in the clinical and research arenas. There is still room for improvements to be made, as the method has lower accuracy when detecting calcific tissue (Table IV). Without being limited by theory, this limitation may be due to the nature of mixed tissue which includes calcium and lipid, and which shares image characteristics of both C and LT. Increasing the clinical dataset and incorporating histological findings in the training/testing phase of the proposed method is expected to solve the former limitation, enable its use in the clinical/research arena, and enhance the field of computational cardiology.

Figure 25:
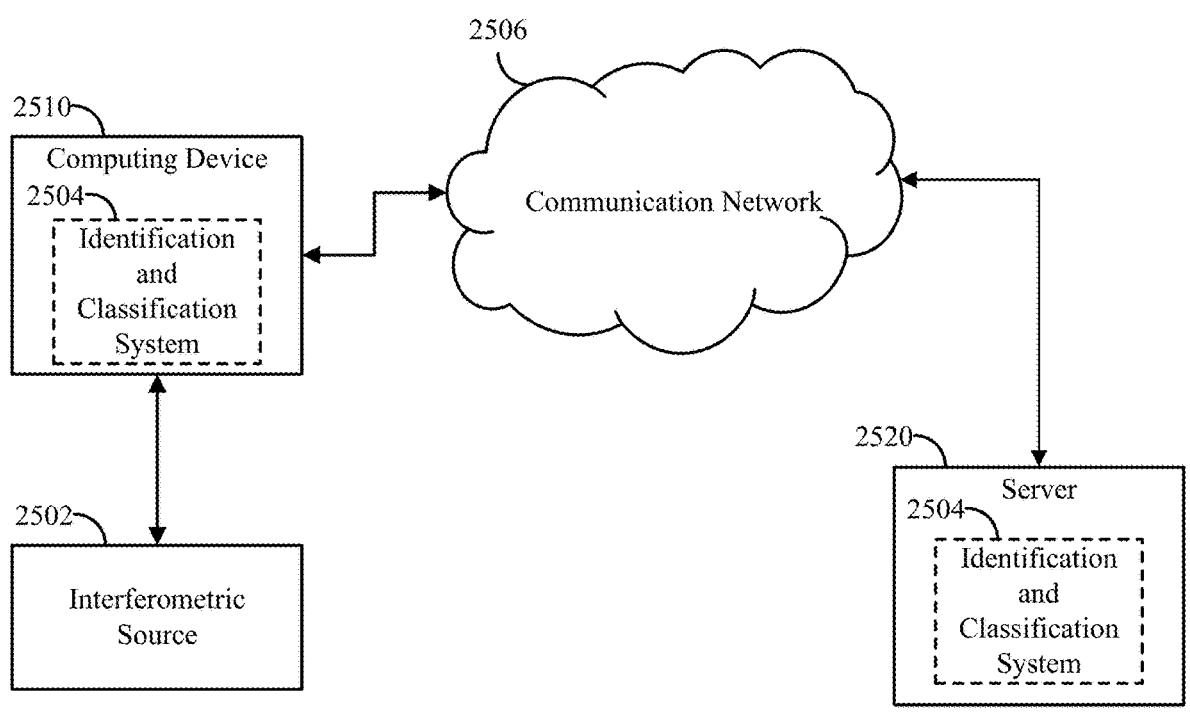
FIG. 25 shows an example of a system for automated identification and classification of atherosclerotic plaques in accordance with some embodiments of the disclosed subject matter.

Turning to FIG. 25, an example 2500 of a system for automated identification and classification of atherosclerotic plaques in intravascular interferometric (e.g. OCT) image data is shown in accordance with some embodiments of the disclosed subject matter. Although the examples shown in FIGS. 25 and 26 and described below are given in the context of an interferometric imaging system, in various embodiments imaging data from other types of imaging systems can be used instead of or in addition to data obtained from an interferometric imaging system. These data types could include sonographic (such as ultrasound imaging), radiographic (such as computed tomography imaging, X-ray microtomography imaging, and angiography), optic (such as endomicroscopy imaging), and nuclear magnetic (such as magnetic resonance imaging) imaging data, among others (including as-yet undeveloped modalities); enhanced imaging like those types and systems utilizing injected dyes may also be used. Imaging systems generating tomographic data are most amenable, but not required. As shown in FIG. 25, a computing device 2510 can receive interferometric data (e.g. tomographic information such as a series of cross-sectional images) from an interferometric source 2502 such as an OCT system. In some embodiments, computing device 2510 can execute at least a portion of an identification and classification system 2504 to identify and/or classify wall area tissue based on tomographic information received from interferometric source 2502. Additionally or alternatively, in some embodiments, computing device 2510 can communicate information about the tomographic information received from interferometric source 2502 to a server 2520 over a communication network 2506, which can execute at least a portion of identification and classification system 2504 to identify and/or classify wall area tissue based on the tomographic information. In some such embodiments, server 2520 can return information to computing device 2510 (and/or any other suitable computing device) indicative of an output of identification and classification system 2504, such as the wall area (WAR) as well as one or more tissue types that have been identified in the tomographic information. This information may be transmitted and/or presented to a user (e.g. an operator, a clinician, etc.) and/or may be stored (e.g. as part of a medical record associated with the subject).

In some embodiments, computing device 2510 and/or server 2520 can be any suitable computing device or combination of devices, such as a desktop computer, a laptop computer, a smartphone, a tablet computer, a wearable computer, a server computer, a virtual machine being executed by a physical computing device, etc. As described herein, identification and classification system 2504 can use one or more trained convolution neural networks (CNNs) to identify one or more types of tissue contained within the WAR and can present information about the WAR and/or the identified tissue type(s) to a user (e.g., a physician).

In some embodiments, interferometric source 2502 can be any suitable source of tomographic interferometry information, such as a system for performing optical coherence tomography (OCT) or related optical tomography modalities such as time domain OCT and Fourier domain OCT modalities. In some embodiments, interferometric source 2502 can be local to computing device 2510. For example, interferometric source 2502 may be incorporated with computing device 2510 (e.g., computing device 2510 can be configured as part of a device for capturing and/or storing tomographic information). As another example, interferometric source 2502 may be connected to computing device 2510 by a cable, a direct wireless link, etc. Additionally or alternatively, in some embodiments, interferometric source 2502 can be located locally and/or remotely from computing device 2510, and can communicate tomographic information to computing device 2510 (and/or server 2520) via a communication network (e.g., communication network 2506).

In some embodiments, communication network 2506 can be any suitable communication network or combination of communication networks. For example, communication network 2506 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 2506 can be a local area network, a wide area network, a public network (e.g., the Internet), a private or semi-private network (e.g., a corporate or university intranet), any other suitable type of network, or any suitable combination of networks. Communications links shown in FIG. 25 can each be any suitable communications link or combination of communications links, such as wired links, fiber optic links, Wi-Fi links, Bluetooth links, cellular links, etc.

Figure 26:
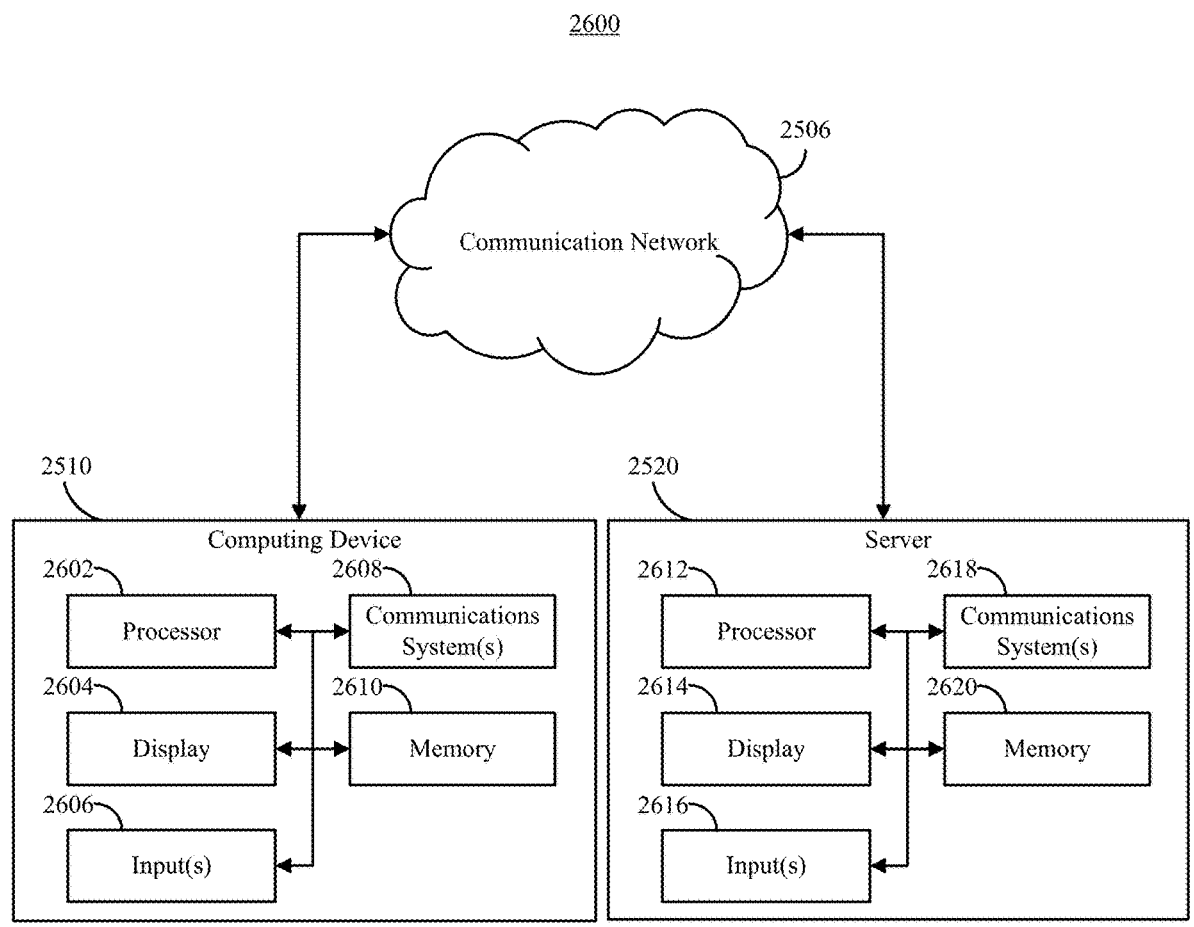
FIG. 26 shows an example of hardware that can be used to implement computing device and server in accordance with some embodiments of the disclosed subject matter.

FIG. 26 shows an example 2600 of hardware that can be used to implement computing device 2510 and server 2520 in accordance with some embodiments of the disclosed subject matter. As shown in FIG. 26, in some embodiments, computing device 2510 can include a processor 2602, a display 2604, one or more inputs 2606, one or more communication systems 2608, and/or memory 2610. In some embodiments, processor 2602 can be any suitable hardware processor or combination of processors, such as a central processing unit, a graphics processing unit, etc. In some embodiments, display 2604 can include any suitable display devices, such as a computer monitor, a touchscreen, a television, etc. In some embodiments, inputs 2606 can include any suitable input devices and/or sensors that can be used to receive user input, such as a keyboard, a mouse, a touchscreen, a microphone, etc.

In some embodiments, communications systems 2608 can include any suitable hardware, firmware, and/or software for communicating information over communication network 2506 and/or any other suitable communication networks. For example, communications systems 2608 can include one or more transceivers, one or more communication chips and/or chip sets, etc. In a more particular example, communications systems 2608 can include hardware, firmware and/or software that can be used to establish a Wi-Fi connection, a Bluetooth connection, a cellular connection, an Ethernet connection, etc.

In some embodiments, memory 2610 can include any suitable storage device or devices that can be used to store instructions, values, etc., that can be used, for example, by processor 2602 to present content using display 2604, to communicate with server 2520 via communications system(s) 2608, etc. Memory 2610 can include any suitable volatile memory, non-volatile memory, storage, or any suitable combination thereof. For example, memory 2610 can include RAM, ROM, EEPROM, one or more flash drives, one or more hard disks, one or more solid state drives, one or more optical drives, etc. In some embodiments, memory 2610 can have encoded thereon a computer program for controlling operation of computing device 2510. In such embodiments, processor 2602 can execute at least a portion of the computer program to present content (e.g., images, user interfaces, graphics, tables, etc.), receive content from server 2520, transmit information to server 2520, etc.

In some embodiments, server 2520 can include a processor 2612, a display 2614, one or more inputs 2616, one or more communications systems 2618, and/or memory 2620. In some embodiments, processor 2612 can be any suitable hardware processor or combination of processors, such as a central processing unit, a graphics processing unit, etc. In some embodiments, display 2614 can include any suitable display devices, such as a computer monitor, a touchscreen, a television, etc. In some embodiments, inputs 2616 can include any suitable input devices and/or sensors that can be used to receive user input, such as a keyboard, a mouse, a touchscreen, a microphone, etc.

In some embodiments, communications systems 2618 can include any suitable hardware, firmware, and/or software for communicating information over communication network 2506 and/or any other suitable communication networks. For example, communications systems 2618 can include one or more transceivers, one or more communication chips and/or chip sets, etc. In a more particular example, communications systems 2618 can include hardware, firmware and/or software that can be used to establish a Wi-Fi connection, a Bluetooth connection, a cellular connection, an Ethernet connection, etc.

In some embodiments, memory 2620 can include any suitable storage device or devices that can be used to store instructions, values, etc., that can be used, for example, by processor 2612 to present content using display 2614, to communicate with one or more computing devices 2510, etc. Memory 2620 can include any suitable volatile memory, non-volatile memory, storage, or any suitable combination thereof. For example, memory 2620 can include RAM, ROM, EEPROM, one or more flash drives, one or more hard disks, one or more solid state drives, one or more optical drives, etc. In some embodiments, memory 2620 can have encoded thereon a server program for controlling operation of server 2520. In such embodiments, processor 2612 can execute at least a portion of the server program to transmit information and/or content (e.g., results of a tissue identification and/or classification, a user interface, etc.) to one or more computing devices 2510, receive information and/or content from one or more computing devices 2510, receive instructions from one or more devices (e.g., a personal computer, a laptop computer, a tablet computer, a smartphone, etc.), etc.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

It should be noted that, as used herein, the term mechanism can encompass hardware, software, firmware, or any suitable combination thereof.

Figure 27:
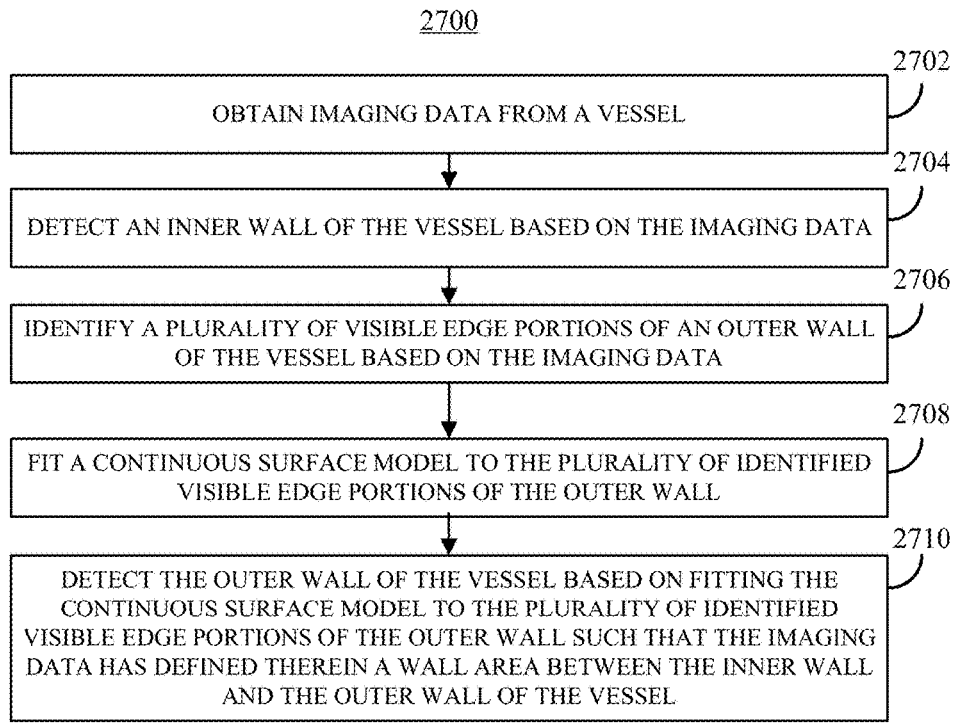
FIG. 27 shows an example of a process for automated identification and/or classification of atherosclerotic plaques in intravascular interferometric image data in accordance with some embodiments of the disclosed subject matter.

FIG. 27 shows an example 2700 of a process for automated identification and/or classification of atherosclerotic plaques in intravascular image data in accordance with some embodiments of the disclosed subject matter. As shown in FIG. 27, at 2702, process 2700 can obtain imaging data from a vessel. At 2704, process 2700 can detect an inner wall of the vessel based on the imaging data. At 2706, process 2700 can identify a plurality of visible edge portions of an outer wall of the vessel based on the imaging data. At 2708, process 2700 can fit a continuous surface model to the plurality of identified visible edge portions of the outer wall. Finally, at 2710, process 2700 can detect the outer wall of the vessel based on fitting the continuous surface model to the plurality of identified visible edge portions of the outer wall such that the imaging data has defined therein a wall area between the inner wall and the outer wall of the vessel.

Figure 28:
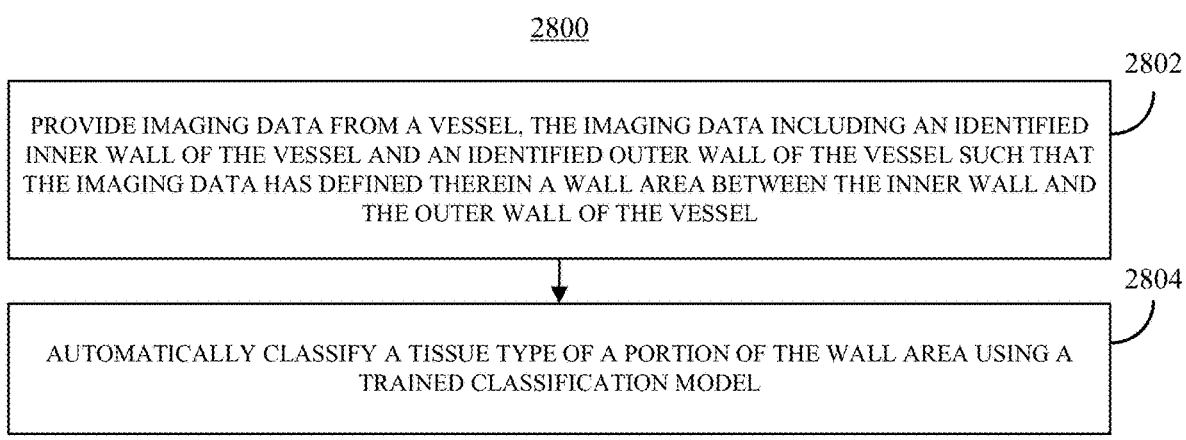
FIG. 28 shows an example of a process for automated identification and/or classification of atherosclerotic plaques in intravascular interferometric image data in accordance with some embodiments of the disclosed subject matter.

FIG. 28 shows an example 2800 of a process for automated identification and/or classification of atherosclerotic plaques in intravascular image data in accordance with some embodiments of the disclosed subject matter. As shown in FIG. 28, at 2802, process 2800 can provide imaging data from a vessel, the imaging data including an identified inner wall of the vessel and an identified outer wall of the vessel such that the imaging data has defined therein a wall area between the inner wall and the outer wall of the vessel. Finally, at 2804, process 2800 can automatically classify a tissue type of a portion of the wall area using a trained classification model.

It should be understood that the above described steps of the processes of FIGS. 27 and 28 can be executed or performed in any order or sequence not limited to the order and sequence shown and described in the figures. Also, some of the above steps of the processes of FIGS. 27 and 28 can be executed or performed substantially simultaneously where appropriate or in parallel to reduce latency and processing times.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

What is claimed is:

1. A method, comprising:
   obtaining, by a processor, imaging data from a vessel;
   detecting, using the processor, an inner wall of the vessel based on the imaging data;
   identifying, using the processor, a plurality of visible edge portions of an outer wall of the vessel based on the imaging data;
   fitting, using the processor, a continuous three-dimensional surface model to the plurality of identified visible edge portions of the outer wall,
   the continuous three-dimensional surface model comprising a linear-elastic mesh model; and
   detecting, using the processor, the outer wall of the vessel based on fitting the continuous three-dimensional surface model to the plurality of identified visible edge portions of the outer wall such that the imaging data has defined therein a wall area between the inner wall and the outer wall of the vessel.

2. The method of claim 1, further comprising:
automatically classifying a tissue type of a portion of the wall area using a trained classification model.

3. The method of claim 2, wherein the tissue type includes at least one of: calcium, lipid tissue, fibrous tissue, mixed tissue, or no visible tissue.

4. The method of claim 2, wherein the trained classification model comprises a trained convolutional neural network (CNN).

5. The method of claim 4, wherein the trained CNN is trained using a database of manually scored images.

6. The method of claim 1, wherein the linear-elastic mesh model comprises an anisotropic linear-elastic mesh including a plurality of interconnected nodes and springs.

7. The method of claim 6, wherein each of the plurality of interconnected nodes and springs is associated with a respective location of the vessel, and
wherein each of the nodes has a respective force value associated therewith.

8. The method of claim 1, further comprising:
determining one or more physical parameters of the vessel based on the continuous three-dimensional surface model.

9. The method of claim 1, further comprising:
classifying a portion of the wall area as non-pathological tissue based on a distance of the portion to at least one of the inner wall or the outer wall of the vessel.

10. The method of claim 1, wherein the imaging data comprises interferometric data, and
wherein obtaining the imaging data from the vessel further comprises:
obtaining the interferometric data from an OCT probe.

11. The method of claim 1, wherein detecting the inner wall of the vessel further comprises:
generating a longitudinal cross-sectional image of the vessel based on the imaging data, and
identifying the inner wall of the vessel by applying bilateral filtering and a K-means algorithm to the longitudinal cross-sectional image.

12. The method of claim 1, wherein detecting the inner wall of the vessel further comprises:
thresholding the imaging data,
identifying, in the imaging data, a plurality of nonzero points closest to a center of the vessel for each of a respective plurality of radial positions, and
fitting lines or a surface to the plurality of nonzero points for each of the plurality of cross-sectional images to identify the inner wall of the vessel.

13. The method of claim 1, further comprising:
transmitting information regarding the wall area to a user.

14. A system, comprising:
at least one hardware processor that is programmed to:
obtain imaging data from a vessel;
detect an inner wall of the vessel based on the imaging data;
identify a plurality of visible edge portions of an outer wall of the vessel based on the imaging data;
fit a continuous three-dimensional surface model to the plurality of identified visible edge portions of the outer wall,
the continuous three-dimensional surface model comprising a linear-elastic mesh model; and
detect the outer wall of the vessel based on fitting the continuous three-dimensional surface model to the plurality of identified visible edge portions of the outer wall such that the imaging data has defined therein a wall area between the inner wall and the outer wall of the vessel.

15. The system of claim 14, wherein the processor is further to:
automatically classify a tissue type of a portion of the wall area using a trained classification model.

16. The system of claim 15, wherein the tissue type includes at least one of: calcium, lipid tissue, fibrous tissue, mixed tissue, or no visible tissue.

17. The system of claim 15, wherein the trained classification model comprises a trained convolutional neural network (CNN).

18. The system of claim 17, wherein the trained CNN is trained using a database of manually scored images.

19. The system of claim 14, wherein the linear-elastic mesh model comprises an anisotropic linear-elastic mesh including a plurality of interconnected nodes and springs.

20. The system of claim 19, wherein each of the plurality of interconnected nodes and springs is associated with a respective location of the vessel, and
wherein each of the nodes has a respective force value associated therewith.

21. The system of claim 14, further comprising:
determining one or more physical parameters of the vessel based on the continuous three-dimensional surface model.

22. The system of claim 14, wherein the processor is further to:
classify a portion of the wall area as non-pathological tissue based on a distance of the portion to at least one of the inner wall or the outer wall of the vessel.

23. The system of claim 14, wherein the imaging data comprises interferometric data, and
wherein the processor, when obtaining the imaging data from the vessel, is further to:
obtain the interferometric data from an OCT probe.

24. The system of claim 14, wherein the processor, when detecting the inner wall of the vessel, is further to:
generate a longitudinal cross-sectional image of the vessel based on the imaging data, and
identify the inner wall of the vessel by applying bilateral filtering and a K-means algorithm to the longitudinal cross-sectional image.

25. The system of claim 14, wherein the processor, when detecting the inner wall of the vessel, is further to:
threshold the imaging data,
identify, in the imaging data, a plurality of nonzero points closest to a center of the vessel for each of a respective plurality of radial positions, and
fit lines or a surface to the plurality of nonzero points for each of the plurality of cross-sectional images to identify the inner wall of the vessel.

26. The system of claim 14, wherein the processor is further to:
transmit information regarding the wall area to a user.

* * * * *

UNITED STATES PATENT AND TRADEMARK OFFICE
CERTIFICATE OF CORRECTION

PATENT NO. : 11,122,981 B2
APPLICATION NO. : 16/415430
DATED : September 21, 2021
INVENTOR(S) : Max Louis Olender et al.

It is certified that error appears in the above-identified patent and that said Letters Patent is hereby corrected as shown below:

In the Specification

Column 10, Line 60, "$P_r \in R^3$" should be -- $P_r \in \mathbb{R}^3$ --.

Column 10, Line 60, "$\in_r \in R_+$" should be -- $\in_r \in \mathbb{R}_+$ --.

Column 10, Line 61, "$S \subset R^3$" should be -- $S \subset \mathbb{R}^3$ --.

Column 28, Line 29, "$I \in R^{H \times H}$" should be -- $I \in \mathbb{R}^{H \times H}$ --.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*